US010377782B2

(12) United States Patent
Hostetler et al.

(10) Patent No.: US 10,377,782 B2
(45) Date of Patent: Aug. 13, 2019

(54) NUCLEOTIDE ANALOGS

(71) Applicant: The Regents of the University of California, Oakland, CA (US)

(72) Inventors: Karl Y. Hostetler, Del Mar, CA (US); James R. Beadle, San Diego, CA (US); Nadejda Valiaeva, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/758,328

(22) PCT Filed: Sep. 15, 2016

(86) PCT No.: PCT/US2016/051942
§ 371 (c)(1),
(2) Date: Mar. 7, 2018

(87) PCT Pub. No.: WO2017/048956
PCT Pub. Date: Mar. 23, 2017

(65) Prior Publication Data
US 2018/0362561 A1 Dec. 20, 2018

Related U.S. Application Data

(60) Provisional application No. 62/218,807, filed on Sep. 15, 2015.

(51) Int. Cl.
C07F 9/6561 (2006.01)
A61P 31/20 (2006.01)
A61K 9/00 (2006.01)
A61K 9/06 (2006.01)
C07F 9/6571 (2006.01)
C07F 9/6512 (2006.01)

(52) U.S. Cl.
CPC ........ *C07F 9/65616* (2013.01); *A61K 9/0014* (2013.01); *A61K 9/06* (2013.01); *A61P 31/20* (2018.01); *C07F 9/6512* (2013.01); *C07F 9/657181* (2013.01)

(58) Field of Classification Search
CPC ............... C07F 9/65616; C07F 9/6512; C07F 9/657181; A61P 31/20; A61K 9/0014; A61K 9/06
USPC .......................................................... 514/81
See application file for complete search history.

(56) References Cited

U.S. PATENT DOCUMENTS

| 4,659,825 A | 4/1987 | Holy et al. |
| 4,724,233 A | 2/1988 | De Clercq et al. |
| 4,808,716 A | 2/1989 | Holy et al. |
| 4,921,951 A | 5/1990 | Shuto et al. |
| 5,484,809 A | 1/1996 | Hostetler et al. |
| 5,532,225 A | 7/1996 | Reist et al. |
| 5,641,763 A | 6/1997 | Holy et al. |
| 5,650,510 A | 7/1997 | Webb, II et al. |
| 5,656,745 A | 8/1997 | Bischofberoer et al. |
| 5,663,159 A | 9/1997 | Starrett, Jr. et al. |
| 5,696,277 A | 12/1997 | Hostetler et al. |
| 5,717,095 A | 2/1998 | Arimilli et al. |
| 5,726,174 A | 3/1998 | Kim et al. |
| 5,733,896 A | 3/1998 | Holy et al. |
| 5,798,340 A | 8/1998 | Bischofberger et al. |
| 5,817,647 A | 10/1998 | Casara et al. |
| 5,840,716 A | 11/1998 | Ubasawa et al. |
| 5,877,166 A | 3/1999 | Reist et al. |
| 5,886,179 A | 3/1999 | Arimilli et al. |
| 5,955,610 A | 9/1999 | Nguyen-Ba et al. |
| 5,977,061 A | 11/1999 | Holy et al. |
| 6,005,107 A | 12/1999 | Nguyen-Ba et al. |
| 6,037,335 A | 3/2000 | Takashima et al. |
| 6,057,305 A | 5/2000 | Holy et al. |
| 6,127,540 A | 10/2000 | Nguyen-Ba et al. |
| 6,197,775 B1 | 3/2001 | Ubasawa et al. |
| 6,225,460 B1 | 5/2001 | Bischofberger et al. |
| 6,448,392 B1 | 9/2002 | Hostetler et al. |
| 6,653,296 B1 | 11/2003 | Holy et al. |
| 6,686,462 B2 | 2/2004 | Rosowsky et al. |
| 6,716,825 B2 | 4/2004 | Hostetler et al. |
| 6,767,900 B2 | 7/2004 | Ubasawa et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,452,898 B2 | 11/2008 | Hostetler et al. |
| 7,452,901 B2 | 11/2008 | Boojamra et al. |
| 7,517,858 B1 | 4/2009 | Hostetler et al. |

(Continued)

FOREIGN PATENT DOCUMENTS

| CN | 101089004 A | 12/2007 |
| CN | 103435672 A | 12/2013 |

(Continued)

OTHER PUBLICATIONS

Aldern et al., "Update and Metabolism of Cidofovir and Oleyloxyethyl-cidofovir in Human Papillomavirus Positive ME-180 Human Cervical Cancer Cells" Abstract 173 *Antiviral Research* (2007) 74(3):A83.
Alexander et al., J. Med. Chem. 46, 4205-4208, 2003.
American Chemical Society. STN Database. RN 123156-16-1, Oct. 13, 1989.
American Chemical Society. STN Database. RN 123155-83-9, Oct. 13, 1989.
American Chemical Society. STN Database. RN 183107-05-3, Nov. 14, 1996, 1 page.
American Chemical Society. STN Database. RN 278611-52-2, Jul. 19, 2000, 1 page.
American Chemical Society. STN Database. RN 1022982-83-7, May 27, 2008, 1 page.
American Chemical Society. STN Database. RN 913356-63-5, Nov. 16, 2006, 1 page.

(Continued)

*Primary Examiner* — Kristin A Vajda
(74) *Attorney, Agent, or Firm* — Eversheds Sutherland (US) LLP

(57) ABSTRACT

Disclosed herein, inter alia, are acyclic nucleotide analogs and methods of using an acyclic nucleotide analog for treating and/or ameliorating a papillomavirus infection.

25 Claims, No Drawings

(56) References Cited

U.S. PATENT DOCUMENTS

| | | |
|---|---|---|
| 7,652,001 B2 | 1/2010 | Hostetler et al. |
| 7,687,480 B2 | 3/2010 | Hostetler et al. |
| 7,749,983 B2 | 7/2010 | Hostetler et al. |
| 7,790,703 B2 | 9/2010 | Hostetler et al. |
| 8,008,308 B2 | 8/2011 | Hostetler et al. |
| 8,088,754 B2 | 1/2012 | Cheng et al. |
| 8,101,745 B2 | 1/2012 | Hostetler et al. |
| 8,163,718 B2 | 4/2012 | Birkus et al. |
| 8,193,167 B2 | 6/2012 | Hostetler et al. |
| 8,309,565 B2 | 11/2012 | Hostetler et al. |
| 8,318,700 B2 | 11/2012 | Hostetler et al. |
| 8,569,321 B2 | 10/2013 | Ware et al. |
| 8,609,627 B2 | 12/2013 | Cho et al. |
| 8,614,200 B2 | 12/2013 | Painter et al. |
| 8,710,030 B2 | 4/2014 | Hostetler et al. |
| 8,835,630 B1 | 9/2014 | Hostetler et al. |
| 8,846,643 B2 | 9/2014 | Hostetler et al. |
| 8,889,658 B2 | 11/2014 | Hostetler et al. |
| 8,962,829 B1 | 2/2015 | Ware et al. |
| 8,993,542 B2 | 3/2015 | Lanier et al. |
| 9,006,218 B2 | 4/2015 | Almond et al. |
| 9,095,599 B2 | 8/2015 | Chang et al. |
| 9,156,867 B2 | 10/2015 | Hostetler et al. |
| 9,156,874 B2 | 10/2015 | Chang et al. |
| 9,206,208 B2 | 12/2015 | Hostetler et al. |
| 9,387,217 B2 | 7/2016 | Hostetler et al. |
| 9,475,832 B2 | 10/2016 | Hostetler et al. |
| 9,493,493 B2 | 11/2016 | Hostetler et al. |
| 9,629,860 B2 | 4/2017 | Hostetler et al. |
| 9,775,852 B2 | 10/2017 | Hostetler et al. |
| 9,801,884 B2 | 10/2017 | Hostetler et al. |
| 2003/0109498 A1 | 6/2003 | Yuasa et al. |
| 2004/0019232 A1 | 1/2004 | Hostetler et al. |
| 2004/0023921 A1 | 2/2004 | Hong et al. |
| 2004/0023928 A1 | 2/2004 | Colacino |
| 2004/0127735 A1 | 7/2004 | Hostetler et al. |
| 2005/0176673 A1 | 8/2005 | Hostetler et al. |
| 2005/0182019 A1 | 8/2005 | Hostetler et al. |
| 2005/0192246 A1 | 9/2005 | Hostetler et al. |
| 2006/0281706 A1 | 12/2006 | Hostetler et al. |
| 2007/0161602 A1 | 7/2007 | Hostetler et al. |
| 2008/0103115 A1 | 5/2008 | Hostetler et al. |
| 2009/0291922 A1 | 11/2009 | Cheng et al. |
| 2010/0173870 A1 | 7/2010 | Hostetler et al. |
| 2010/0273742 A1 | 10/2010 | Hostetler et al. |
| 2012/0058975 A1 | 3/2012 | Hostetler et al. |
| 2012/0116067 A1 | 5/2012 | Meier et al. |
| 2012/0164104 A1 | 6/2012 | Lanier et al. |
| 2013/0029940 A1* | 1/2013 | Hostetler ............... A61K 31/52 514/81 |
| 2013/0045950 A1 | 2/2013 | Hostetler et al. |
| 2014/0045794 A1 | 2/2014 | Hostetler et al. |
| 2015/0011488 A1 | 1/2015 | Preston et al. |
| 2015/0051174 A1 | 2/2015 | Hostetler et al. |
| 2015/0141375 A1 | 5/2015 | Painter et al. |
| 2016/0303147 A1 | 10/2016 | Painter et al. |
| 2017/0096441 A1 | 4/2017 | Hostetler et al. |
| 2017/0189430 A1 | 7/2017 | Hostetler et al. |
| 2017/0304330 A1 | 10/2017 | Hostetler et al. |
| 2018/0015095 A1 | 1/2018 | Hostetler et al. |
| 2018/0064737 A1 | 3/2018 | Hostetler et al. |
| 2018/0071323 A1 | 3/2018 | Hostetler et al. |

FOREIGN PATENT DOCUMENTS

| | | |
|---|---|---|
| CN | 106188192 A | 12/2016 |
| CS | 263953 B1 | 5/1989 |
| CS | 263955 B1 | 5/1989 |
| CS | 263956 B1 | 5/1989 |
| CZ | 292199 | 8/2003 |
| RU | 2187509 C1 | 8/2002 |
| WO | WO 1991/19726 A1 | 12/1991 |
| WO | WO 1992/03462 A1 | 3/1992 |
| WO | WO 1993/19075 A1 | 9/1993 |
| WO | WO 1995/32984 A1 | 9/1993 |
| WO | WO 1998/42351 A1 | 12/1995 |
| WO | WO 1999/62921 A1 | 12/1999 |
| WO | WO 2000/029414 A1 | 5/2000 |
| WO | WO 2001/39724 A2 | 6/2001 |
| WO | WO 2002/057288 A1 | 7/2002 |
| WO | WO 2002/087465 A2 | 11/2002 |
| WO | WO 2003/002580 A1 | 1/2003 |
| WO | WO 2003/050129 A1 | 6/2003 |
| WO | WO 2003/090690 A2 | 11/2003 |
| WO | WO 2003/090691 A2 | 11/2003 |
| WO | WO 2003/099294 A1 | 12/2003 |
| WO | WO 2004/096235 A2 | 11/2004 |
| WO | WO 2004/096286 A2 | 11/2004 |
| WO | WO 2004/111064 A1 | 12/2004 |
| WO | WO 2005/066189 A1 | 7/2005 |
| WO | WO 2005/087788 A2 | 9/2005 |
| WO | WO 2006/066074 A2 | 6/2006 |
| WO | WO 2006/076015 A2 | 7/2006 |
| WO | WO 2006/114064 A2 | 11/2006 |
| WO | WO 2006/114065 A2 | 11/2006 |
| WO | WO 2007/002912 A2 | 1/2007 |
| WO | WO 2007/130783 A2 | 11/2007 |
| WO | WO 2008/104408 A2 | 9/2008 |
| WO | WO 2009/094190 A2 | 7/2009 |
| WO | WO 2010/135520 A1 | 11/2010 |
| WO | WO 2011/011519 A1 | 1/2011 |
| WO | WO 2011/011710 A1 | 1/2011 |
| WO | WO 2011/130557 A2 | 10/2011 |
| WO | WO 2014/143643 A1 | 9/2014 |
| WO | WO 2016/044281 A1 | 3/2016 |
| WO | WO 2016/195522 A2 | 12/2016 |

OTHER PUBLICATIONS

American Chemical Society. STN Database. RN 1204478-93-2, Feb. 3, 2010, 1 page.

American Chemical Society. STN Database. RN 1204478-95-4, Feb. 3, 2010, 1 page.

Balzarini, J., et al. "9-[(2R5)-3-Fluoro-2-phosphonylmethoxypropyl] derivatives of purines: A class of highly selective antiretroviral agents in vitro and in vivo." Proc. Natl. Acad. Sci. (1991), vol. 88, pp. 4961-4965.

Baker et al., Antiviral Res. 57: 13-23, 2003.

Beadle, J.R. et al. (Aug. 2002). "Alkoxyalkyl esters of cidofovir and cyclic cidofovir exhibit multiple-log enhancement of antiviral activity against cytomegalovirus and herpesvirus replication in vitro," Antimicrob Agents Chemother 46(8):2381-2386.

Beadle et al., "Synthesis and Antiviral Evaluation of Alkoxyalkyl Derivatives of 9-(S)-(3-Hydroxy-2-phosphonomethoxypropyl)adenine against Cytomegalovirus", *Journal of Medicinal Chemistry*, 2006, 49:2010-2015.

Benzaria, S. et al. (Dec. 6, 1996). "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability.," J. Med. Chem. 39(25):4958-4965.

Bronson et al., J. Med. Chem., 1989, 32, P. 1457-1463.

Bronson et al., Nucleotide Analogues as Antiviral Agents, Chapter 5, p. 72-87, ACS Symposium Series, 1989, vol. 401.

Brown, N.A. (2009). "Progress towards improving antiviral therapy for hepatitis C with hepatitis C virus polymerase inhibitors. Part 1: Nucleoside analogues," *Expert Opinion on investigational Drugs* 18(6):709-725.

Buchwald et al. (1980). Surgery 88:507-516.

Buller et al. (2004). Virology, 318:474-481.

Campagne et al., "Synthesis of Mixed Phosphonate Diester Analogues of Dipeptides using BOP or PyBOP Reagents", *Tetrahedron Letters*, 1993, 34(42):6743-6744.

CAS RN:278611-19-1, Registry. Jul. 19, 2000, 1 page.

CAS RN:278611-52-2, Registry. Jul. 19, 2000, 1 page.

Chand, P., Expert Opinion on Therapeutic Patents, 15 (8):1009-1025, 2005.

Cundy, K.C., Clinical Pharmacokinetics, 36:127-143, 1999.

(56) References Cited

OTHER PUBLICATIONS

Database Caplus [Online] Chemical Abstracts Service, Columbus, Ohio, US; Otmar, Miroslav et al: "An alternative synthesis of HPMPC and HPMPA diphosphoryl derivatives", retrieved from STN Database accession No. 2000:234286; & Otmar, Miroslav et al: "An alternative synthesis of HPMPC and HPMPA diphosphoryl derivatives", Collection Symposium Series, 2(Chemistry of Nucleic Acid Components), 252-254 CODEN: CSYSFN, 1999, 2 pages.

Database Caplus [Online] Chemical Abstracts Service, Columbus, Ohio, US; Votruba, Ivan et al: "Inhibition of human purine nucleoside phosphorylase by tenofovir phosphate congeners", retrieved from STN Database accession No. 2010:1628491 ; & Votruba, Ivan et al: "Inhibition of human purine nucleoside phosphorylase by tenofovir phosphate congeners", Collection of Czechoslovak Chemical Communications, 75(12), 1249-1257 CODEN: CCCCAK; ISSN: 0010-0765, 2010, 1 page.

DeClercq, Clinical Microbiology Reviews, 14:382-297, 2001.

De Clercq, E. (2007). "Acyclic nucleoside phosphonates: Past, present and future Bridging chemistry to HIV, HBV, HCV, HPV, adeno-, herpes-, and poxvirus infections : The phosphonate bridge", Biochemical Pharmacology, 73:911-922.

Figlerowicz, M., et al. (2003). "Genetic Variability: The Key Problem in the Prevention and Therapy of RNA-Based Virus Infections." Medicinal Research Reviews 23(4):488-518.

Franchetti, P. et al. (Sep. 1994). "8-Aza-analogues of PMEA and PMEG: Synthesis and In Vitro Anti-HIV Activity," Nucleosides & Nucleotides 13(8):1707-1719.

Haynes, U.J. et al. (Aug. 1993)." Syntheses of 9-(2'-monoethylphosphonomethoxyethyl)- 8-[14C]guanine ([14C]-EPMG) and 9-(2'-phosphonomethoxyethyl)-8-[14C]guanine ([14C]-PMEG)," Journal of Labelled Compounds and Radiopharmaceuticals 33(8):795-799.

Heijtink, R.A. et al. (Sep. 1994). "Inhibitory effects of acyclic nucleoside phosphonates on human hepatitis B virus and duck hepatitis B virus infections in tissue culture," Antimicrob Agents Chemother 38(9):2180-2182.

Holy, A. et al. (1987). "Synthesis of 9-(2-Phosphonylmethoxyethyl) Adenine and Related Compounds," Collection Czechoslovak Chem Commun (52):2801-2809.

Holy et al., "Structure-Antiviral Activity Relationship in the Series of Pyrimidine and Purine N- [2-(2-Phosphonomethyoxy)ethyl] Nucleotide Analogues. 1. Derivatives Substituted at the Carbon Atoms of the base" J. Med. Chem. (1999) 42(12):2064-2086.

Holy, A. (2006). "'Antiviral acyclic nucleoside phosphonates structure activity studies," Antiviral Research 71:248-253.

Hostetler et al., Antiviral Research, 31:59-67, 1996.

Hostetler et al., "Enhanced antiproliferative effects of alkoxyalkyl esters of cidofovir in human cervical cancer cells in vitro" Mo/ Cancer Ther (2006) 51(1):156-158.

Hostetler et al., "Alkoxyalkyl Esters of (S)-9-[3-Hydroxy-2-(Phosphonomethoxy)propyl]Adenine Are Potent Inhibitors of the Replication of Wild-Type and Drug-Resistant Human Immunodeficiency Virus Type 1 in Vitro", Antimicrobial Agents and Chemotherapy, American Society for Microbiology, 50(8):2857-2859 (2006).

Hostetler et al., Antiviral Research, 2007, 73(3), p. 212-218.

Huggins, J.W. et al., (2002). "Orally Active Ether Lipid Prodrugs of Cidofovir for the Treatment of Smallpox," Antiviral Research, 53:A66 (104).

International Search Report dated Jul. 19, 2006 for International PCT Application No. PCT/US2005/045579, 4 pages.

International Preliminary Report on Patentability and Written Opinion dated Jun. 19, 2007 for International PCT Application No. PCT/US2005/045579, 8 pages.

International Preliminary Report on Patentability and Written Opinion dated Oct. 16, 2012 for International Application No. PCT/US2011/032558, 11 pages.

International Search report dated Jan. 18, 2012 for International Application No. PCT/US2011/032558, 5 pages.

International Search Report and Written Opinion dated May 29, 2014 for International Application No. PCT/US2014/027005, 9 pages.

International Search Report dated Dec. 4, 2015, for PCT Application No. PCT/US2015/050202, filed Sep. 15, 2015, 3 pages.

International Search Report dated Dec. 7, 2016, for PCT Application No. PCT/US2016/51942, filed Sep. 15, 2016, 4 pages.

Iyer et al., "Phosphorothioate Di- and Trinucleotides as a Novel Class of Anti-Hepatitis B Virus Agents", Antimicrobial Agents and Chemotherapy, 2004, 48(6):2199-2205.

Jansa, P. et al. (Sep. 2011, e-published May 23, 2011). "A novel and efficient one-pot synthesis of symmetrical diamide (bis-amidate) prodrugs of acyclic nucleoside phosphonates and evaluation of their biological activities," European Journal of Medicinal Chemistry, 46(9):3748-3754.

Jansa et al., "Microwave-assisted hydrolysis of phosphonate diesters: an efficient protocol for the preparation of phosphonic acids" Green Chem. (2012) 14:2282-88.

Jindrich et al., "Synthesis of N-(3-Fluoro-2-Phosphonomethoxypropyl) (FPMP) Derivatives of Heterocyclic Bases", Collect. Czech. Chem. Commun., 1993, 58:1645-1667.

Keith et al., Antimicrobial Agents and Chemotherapy, 48:5, p. 1869-1871, May 2004.

Keough, D.T. et al. (Jul. 23, 2009). "Inhibition of hypoxanthine-guanine phosphoribosyltransferase by acyclic nucleoside phosphonates: a new class of antimalarial therapeutics," J Med Chem 52(14):4391-4399.

Kern et al., "Enhanced Inhibition of Orthopoxvirus Replication in Vitro by Alkoxyalkyl Esters of Cidofovir and Cyclic Cidofovir", Antimicrobial Agents and Chemotherapy, 46(4):991-995 (2002).

Koh, Y-H. et al., (2005). "Design, Synthesis and Antiviral Activity of Adenosine 5'-Phosphonate Analogues as Chain Terminators against Hepatitis C Virus", Journal of Medicinal Chemistry 48(8):2867-2875.

Kramata, P. et al. (Jun. 1996). "Different inhibitory potencies of acyclic phosphonomethoxyalkyl nucleotide analogs toward DNA polymerases alpha, delta and epsilon," Mol Pharmacol. 49(6):1005-1011.

Kramata, P. et al (Aug. 21, 1998). "Incorporation and excision of 9-(2-phosphonylmethoxyethyl)guanine (PMEG) by DNA polymerase delta and epsilon in vitro," 273(34):21966-21971.

Magee et al., "Mechanism of Inhibition of Vaccinia Virus DNA Polymerase by Cidofovir Diphosphate", Antimicrobial Agents and Chemotherapy, American Society for Microbiology, 49(8):3153-3162 (2005).

Maloisel et al., Antiviral Chemistry and Chemotherapy I, 10:333-345, 1999.

McKimm-Breschkin et al. (2003). Angew Chem 115:3226-3229.

Meier, C. et al. (Dec. 15, 2005). "cycloSal-PMEA and cycloAmb-PMEA: potentially new phosphonate prodrugs based on the cycloSal-pronucleotide approach," J. Med. Chem. 48(25):8079-8086.

Merta et al., "Phosphorylation of 9-(2-phosphonomethoxyethyl) adenine and 9(S)-(3-hydroxy-2-phosphonomethoxypropyl)adenine by AMP (dAMP) kinase from L1210 cells", Biochemical Pharmacology, Elsevier, 44(10):2067-2077 (1992).

Naesens, L. et al. (1995, published online Feb. 16, 2007). "In vivo Antiretroviral Efficacy of Oral bis(POM)-PMEA, the bis(Pivaloyloxymethyl)prodrug of 9-(2-Phosphonylmethoxyethyl) adenine (PMEA)," Nucleosides & Nucleotides 14(3-5):767-770.

Painter et al., "Evaluation of Hexadecyloxypropyl-9-R-[2-(Phosphomethoxy)Proply]-Adenine, CMX157, as a Potential Treatment for Human Immunodeficiency Virus Type 1 and Hepatitis B Virus Infections." Antimicrobial Agents and Chemotherapy , 2007, 51:3505-3509.

Pertusati, F. et al. "Medicinal chemistry of nucleoside phosphonate prodrugs for antiviral therapy." Antiviral Chemistry & Chemotherapy. (2012), vol. 22, pp. 181-203.

Pomeisl et al., "Pyrimidine Acyclic Nucleoside Phosphonates and Phosphorylated Analogs (Part 2): Syntheses and Investigation of Their Inhibitory Effects Towards Human Thymidine Phosphorylase", Nucleic Acids Symposium Series, 52(1): 657-658 (2008).

(56) References Cited

OTHER PUBLICATIONS

Pradere, U. et al. (Sep. 24, 2014, e-published Aug. 21, 2014). "Synthesis of Nucleoside and Phosphonate Prodrugs," Chemical Reviews 114(18):9154-9218.

Prichard et al., "Inhibition of Herpesvirus Replication by Hexadecyloxypropyl Esters of Purine- and Pyrimidine-Based Phosphonomethoxyethyl Nucleoside Phosphonates", Antimicrobial Agents and Chemotherapy, 52:4326-4330 (2008).

Puech, F. et al. (Oct. 1993). "Intracellular delivery of nucleoside monophosphates through a reductase-mediated activation process," Antiviral Research 22:155-174.

Quenelle, Antimicrobial Agents Chemotherapy, 48:404-412, 2004.

Reddy, K.R. et al. (Feb. 14, 2008, e-published Jan. 4, 2008). "Pradefovir: a prodrug that targets adefovir to the liver for the treatment of hepatitis B," J. Med. Chem. 51(3):666-676.

Rosenberg, I. et al. (1988). "Phosphonylmethoxyalkyl and Phosphonylalkyl Derivatives of Adenine*," Collection Czechoslovak Chem. Commun., 53:2753-2777.

Saudek et al. (1989). N. Engl. J. Med. 321(9):574-579.

Sefton, M.V. (1987). CRC Crit. Ref. Biomed. Eng. 14(3):201-240.

Sheng, X.C. et al. (2009). "Discovery of novel phosphonate derivatives as hepatitis C virus NS3 protease inhibitors", Bioorganic & Medicinal Chemistry Letters 19:3453-3457.

Srivasta, D.N. et al. (1984). "Bioreversible Phosphate Protective Groups: Synthesis and Stability of Model Acyloxymethyl Phosphates," Bioorg. Chem 12:118-129.

Starrett, J.E. Jr. et al. (Jun. 10, 1994). "Synthesis, oral bioavailability determination, and in vitro evaluation of prodrugs of the antiviral agent 9-[2(phosphonomethoxy)ethyl]adenine (PMEA).," J. Med. Chem. 37:1857-1864.

Tichy, T. et al. (Jun. 1, 2011, e-published Apr. 22, 2011). "New prodrugs of Adefovir and Cidofovir," Bioorg. & Med. Chem. 19(11):3527-3539.

Tobias, S. C. et al.,(Mar.-Apr. 2004). "Synthesis and biological evaluation of a cytarabine phosphoramidate prodruq," Mol. Pharmaceutics 1(2):112-116.

Trahan et al., "Antiproliferative Effects of Octadecyloxyethyl-Phosphonomethoxyethylguanine (ODE-PMEG) on the Growth of Human Papilloma Virus Positive Cervical Carcinoma (ME-180) Cells in Vitro and Solid Tumors in Athymic Nude Mice" Abstract 85 *Antiviral Research* (2009) 82(2):A42.

Valiaeva et al., "Synthesis and antiviral evaluation of alkoxyalkyl esters of acyclic purine and pyrimidine nucleoside phosphonates against HIV-1 in vitro", *Antiviral Research*, 2006, 72:10-19.

Valiaeva Nadejda et al., "Antiviral evaluation of octadecyloxyethyl esters of (S)3-hydroxy-2-(-(phosphonomethoxy)propyl nucleosides against herpesviruses and orthopoxviruses", Antiviral Research, 2009, vol. 84, DD 254-259.

Valiaeva et al., "Antiproliferative Effects of Octadecyloxyethyl 9-[2-(Phosphonomethoxy)Ethyl] Guanine against Me-180 Human Cervical Cancer Cells in vitro and in vivo", *Chemotherapy*, 2010, 56(1):54-59.

Valiaeva et al. "Synthesis and antiviral evaluation of 9-(S)-[3-alkoxy-2-(phosphonomethoxy)-proply] nucleoside alkoxyalkyl esters: Inhibitors of hepatitis C virus and HIV-1 replication", *Bioorganic & Medicinal Chemistry*, 2011, 19:4616-4625.

Vrbkova et al., "Synthesis of phosphonomethyoxyethyl or 1,3-bis(phosphonomethyoxy)propan-2-yl lipophilic esters of acyclic nucleoside phosphonates" *Tetrahedron* (2007) 63:11391-11398.

Webb, R.R., "The Bis-Trityl Route to (S)-HPMPA", *Nucleosides & Nucleotides*, 1989, 8(4):619-624.

Written Opinion dated Dec. 4, 2015, for PCT Application No. PCT/US2015/050202, filed Sep. 15, 2015, 4 pages.

Written Opinion dated Dec. 7, 2016, for PCT Application No. PCT/US2016/51942, filed Sep. 15, 2016, 12 pages.

Wyles et al., "The Octadecyloxyethyl Ester of (S)-9-[3-Hydroxy-2-(Phosphonomethoxy)Propyl]Adenine Is a Potent and Selective Inhibitor of Hepatitus C Virus Replication in Genotype 1A, 1B, and 2A Replicons", Antimicrobial Agents and Chemotherapy, American Society for Microbioloav, 53:2660-2662 (2009).

Yokota et al., "Inhibitory effects of acyclic nucleoside phosphonate analogs on hepatitis B virus DNA synthesis in HB611 cells", Antiviral Chemistry and Chemotherapy, 5(2):57-63 (1994).

Yu, K.L. et al. (Aug. 1992). "Synthesis and antiviral activity of methyl derivatives of 9-[2-(phosphonomethoxy)ethyl]guanine," *J Med Chem* 35(16):2958-2969.

European Search Report for EP Application No. 16847300.7 dated Feb. 14, 2019 (7 pages).

\* cited by examiner

NUCLEOTIDE ANALOGS

STATEMENT OF RELATED APPLICATIONS

This application claims the benefit of U.S. Provisional Patent Application No. 62/380,205 filed Sep. 15, 2015, which is hereby incorporated by reference in its entirety and for all purposes.

FIELD

The present application is directed to nucleotide analogs, pharmaceutical compositions that include a disclosed nucleotide analog, and processes for their synthesis. The invention also includes methods of treating diseases and/or conditions with the disclosed nucleotide analog, alone or in combination therapy with one or more other agents, including in particular for the treatment of a viral infection in a host such as that caused by a papillomavirus.

BACKGROUND OF THE INVENTION

Viruses are infectious particles that can replicate their DNA or RNA only within host cells. Viral infections may lead to mild to severe illnesses in humans and mammals, and in some instances, can result in death. Examples of viral infections include hepatitis B and C, smallpox, herpes simplex, cytomegalovirus, human immunodeficiency virus (HIV), influenza, adenovirus, chickenpox, BK virus, JC virus and papillomavirus. Viral infection can lead to cancer in humans and other species. Viruses known to cause cancer include human papillomavirus (HPV), hepatitis B virus (HBV), hepatitis C virus (HCV), HIV and Epstein Barr virus (EBV).

Papillomaviruses are a group of non-enveloped DNA viruses, which in humans infect keratinocytes of skin and mucous membranes including in the anogenital area. They are known to cause skin warts, genital warts, and respiratory papillomatosis and cancer. In women, Papillomaviruses can cause precancerous cervical lesions which lead to cervical intraepithelial neoplasia, vaginal and anal intraepithelial neoplasia, and ultimately cervical cancer.

Several species of the alpha-papillomavirus genus contain high risk types of HPV which are more likely to lead to human cancer. Most of the cancer-causing HPV types are from the alpha-7 and alpha-9 species and include types 16, 18, 31, 33, 35, 39, 45, 51, 52, 56, 58, 59, 68, 73, and 82. Cancers caused by HPV include cervical, rectal, penile, vaginal and oropharyngeal cancer. The most common cancer-causing HPV types are 16 and 18. HPV-16 and -18 are reported to be the cause of 70% of cervical cancers; and 90% of venereal warts are caused by the low risk HPV types 6 and 11. The presence of a HPV infection can be detected using a PAP smear and/or DNA probe testing with products such as CEREVISTA® (Hologic), COBAS® (Roche) and other commercially available products. Currently available HPV DNA tests detect DNA from 14 high-risk HPV types, including HPV-16 and HPV 18. Vaccines have been developed for HPV 6, 11, 16 and 18, which may be effective if administered prior to sexual debut. However, the HPV vaccines may provide little benefit in sexually active women who have already been infected with HPV.

HPV replication and viral DNA synthesis that produce mature virions first takes place in the basilar layer of cervical epithelial cells and amplifies to involve the suprabasilar cells as the infection proceeds. After months or years of infection, elements of the HPV DNA episome can become integrated into the epithelial cell genomic DNA. The integrated elements generally include viral L1, the long control region (LCR), and the E6 and E7 oncogenes. This results in overexpression of E6 and E7 oncoproteins that over time cause the loss of cell cycle controls and progression to cervical cancer. However, in cervical cancer cell lines which have integrated HPV DNA such as HeLa (HPV18), SiHa (HPV16), CaSki (HPV16) and Me180 (HPV39) productive viral replication is not occurring. Thus, studies of compounds which inhibit cell division of human cervical cancer cell lines that contain integrated E6 and E7 do not provide knowledge about the inhibition of productive viral DNA synthesis. Additional information regarding HPV and its replication is provided in Fields Virology 1662-1703 (David M. Knipe, Ph.D. and Peter M. Howley, MD eds., 6th ed., Wolters Kluwer, 2013) (2001), which is hereby incorporated by reference in its entirety. There is presently no approved antiviral treatment for a human papillomavirus infection.

One class of antiviral drugs are nucleoside or nucleotide analogs, which interfere with DNA or RNA replication necessary for viral growth. Examples of antiviral nucleoside analogs include RETROVIR®, ZOVIRAX®, CYTOVENE®, EPIVIR® and EMTRIVA®.

Nucleotide analogs include the acyclic nucleoside phosphonates (ANPs). Nucleotide analogs were initially designed to circumvent the first phosphorylation of a parent nucleoside. This first phosphorylation has been identified as the limiting step in the generation of the active nucleoside triphosphate. Examples of ANPs include adefovir, tenofovir and cidofovir (CDV) which are active against human infections such as HBV, HIV and CMV, respectively. ANPs are known in the art to be poorly adsorbed from the gastrointestinal tract of mammals due to 1) their molecular weight and 2) the presence of a double negative charge on the phosphonate moiety. Because of their poor oral pharmacokinetic properties, ANPs have been converted to prodrugs to produce clinically useful therapeutic agents. For example, tenofovir is marketed as VIREAD®; a disoproxil (diester) fumarate salt, for the treatment of HIV. Adefovir is marketed as HEPSERA®; a dipivoxil ester, for the treatment of HBV.

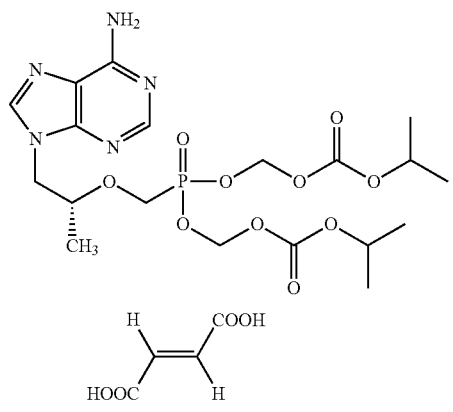

VIREAD®, tenofovir disoproxil fumarate

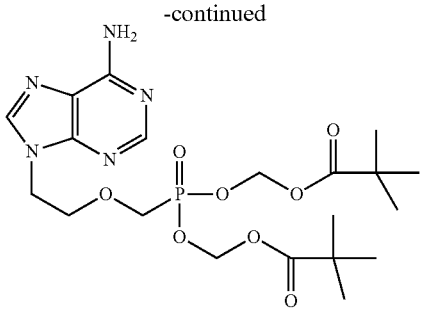

HEPSERA®, adefovir dipivoxil

Additional examples of ANP prodrugs include pradefovir (Phase III) and GS-7340. GS-7340, tenofovir alafenamide, has been approved for the treatment of HIV and is part of the fixed-dose combinations GENVOYA®, ODEFSEY® and DESCOVY®. See, for example, Pradere, U. et al., "Synthesis of Nucleoside and Phosphonate Prodrugs", Chemical Reviews, 2014, 114, 9154-9218 and the structures below.

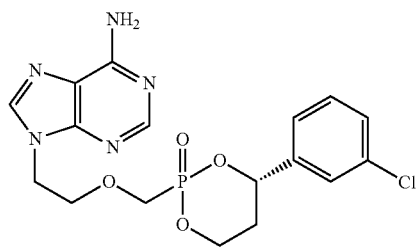

Pradefovir

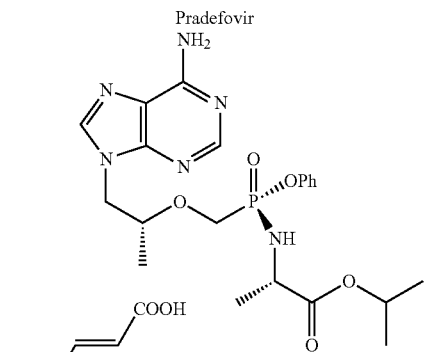

GS-7340

An alternate approach to increasing the oral bioavailability of ANPs has been to prepare alkoxyalkyl monoesters or alkyl monoesters. See, for example, Beadle et al., "Synthesis and Antiviral Evaluation of Alkoxyalkyl Derivatives of 9-(S)-(3-Hydroxy-2-phosphono-methoxypropyl)adenine against Cytomegalovirus", J. Med. Chem., 2006, 49:2010-215; Painter et al., "Evaluation of Hexadecyloxypropyl-9-R-[2-(Phosphonomethoxy)Propyl]-Adenine, CMX157, as a Potential Treatment for Human Immunodeficiency Virus Type 1 and Hepatitis B Virus Infections," Antimicrobial Agents and Chemotherapy, 2007, 51:3505-3509; Valiaeva et al., "Synthesis and antiviral evaluation of alkoxyalkyl esters of acyclic purine and pyrimidine nucleoside phosphonates against HIV-1 in vitro", Antiviral Research, 2006, 72:10-19; Aldern et al., "Update and Metabolism of Cidofovir and Oleyloxyethyl-cidofovir in Human Papillomavirus Positive ME-180 Human Cervical Cancer Cells" Abstract 173 Antiviral Res., 2007, 74(3):A83; Hostetler et al., "Enhanced Anti-proliferative effects of alkoxyalkyl esters of cidofovir in human cervical cancer cells in vitro" Mol. Cancer Ther., 2006, 51(1):156-158; Trahan et al., "Anti-proliferative Effects of Octadecyloxyethyl-Phosphonomethoxyethylguanine (ODE-PMEG) on the Growth of Human Papilloma Virus Positive Cervical Carcinoma (ME-180) Cells in Vitro and Solid Tumors in Athymic Nude Mice" Abstract 85 Antiviral Res., 2009, 82(2):A42; Valiaeva et al., "Antiproliferative Effects of Octadecyloxyethyl 9-[2-(Phosphonomethoxy)Ethyl] Guanine against Me-180 Human Cervical Cancer Cells in vitro and in vivo", Chemotherapy, 2010, 56:(1)54-59; Valiaeva et al., "Synthesis and antiviral evaluation of 9-(S)-[3-alkoxy-2-(phosphonomethoxy)-propyl] nucleoside alkoxyalkyl esters: Inhibitors of hepatitis C virus and HIV-1 replication", Bioorganic and Medicinal Chemistry, 2011, 19:4616-4625. In addition, see the patent applications and patents to Hostetler: U.S. Pat. Nos. 6,716,825; 7,034,014; 7,094,772; 7,098,197; 7,652,001; 7,452,898; 7,790,703; 7,687,480; 7,749,983; 7,994,143; 8,101,745; 8,008,308; 8,193,167; 8,309,565; 8,318,700; 8,846,643; 8,710,030; 8,889,658, 9,156,867; 9,387,217 and US 2015/0080344; The Regents of The University of California: WO 1996/39831; WO 2001/039724; WO 2005/087788; WO 2006/066074; WO 2006/076015; and WO 2011/130557; and the Dana Farber Cancer Institute, Inc.: WO/1998/38202.

A hexadecyloxypropyl ester of cidofovir, HDP-CDV (brincidofovir), is currently being developed for the treatment of adenovirus. The drug is currently in Phase III. See, for example, U.S. Pat. No. 9,006,218; 8,993,542; 8,962,829; 8,614,200; 8,569,321; 7,994,143; 7,749,983; 6,599,887; 6,448,392; WO 2007/130783; WO 2008/133966; WO 2009/094190; WO 2011/011519; WO 2011/011710; WO 2011/017253 and WO 2011/053812.

The synthesis of phosphonomethoxyethyl or 1,3-bis (phosphonomethoxy)propan-2-yl lipophilic esters of acyclic nucleoside phosphonates, and alkyl diesters of ANPs have been disclosed See, Holy et al., "Structure-Antiviral Activity Relationship in the Series of Pyrimidine and Purine N-[2-(2-Phosphono-methyloxy)ethyl] Nucleotide Analogues. Derivatives Substituted at the Carbon Atoms of the base", J. Med. Chem., 1999, 42(12):2064-2086; Holy et al., "Synthesis of phosphonomethoxyethyl or 1,3-bis(phosphonomethoxy) propan-2-yl lipophilic esters of acyclic nucleoside phosphonates", Tetrahedron, 2007, 63:11391-11398. The synthesis of anti-cancer phosphonate analogs has also been investigated; see, WO 2004/096235; WO 2005/066189 and WO 2007/002808. The synthesis of prodrugs of ANPs has also been investigated; see, WO 2006/114064 and WO 2006/114065. The synthesis of purine nucleoside monophosphate prodrugs for the treatment of cancer and viral infections has also been investigated; see, WO 2010/091386.

Certain acyclic nucleoside phosphonate diesters are disclosed in U.S. Pat. Nos. 8,835,630; 9,156,867; and 9,387,217.

While there are currently no approved pharmaceutical drugs that are used to treat an early HPV infection that has not yet progressed to cancer, certain epicatechins, epicatechin oligomers or thiolated epicatechins from *Theobroma cacao* for treatment of genital warts have been disclosed; see, US 2015/0011488.

The pyrimidine, 5-fluorouracil, is active against HPV but is highly toxic. The broad spectrum antiviral agent GSK983 has been shown to have anti HPV activity but has not been studied extensively in humans yet. Other small molecules having anti-HPV activity include the cobalt complex CDC-96, indol-3-carbinol (I3C) and the immunomodulatory Imiquimod, see, US 2015/0011488.

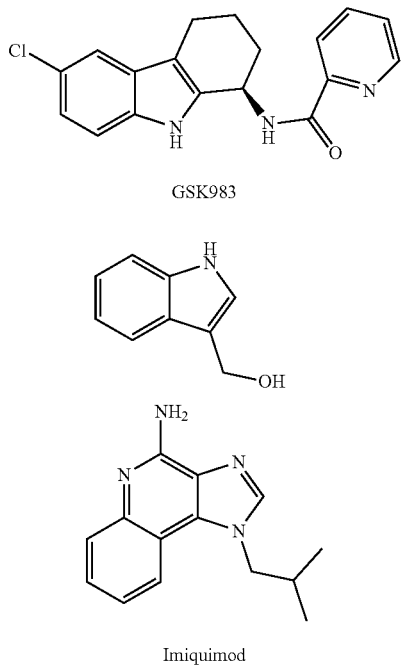

GSK983

I3C

Imiquimod

To date, there are no approved pharmaceutical drugs that are used to treat an early HPV infection that has not yet progressed to cancer. Provided herein are solutions to these and other problems in the art.

BRIEF SUMMARY OF THE INVENTION

The present invention provides new compounds, composition and methods that for the treatment of viral diseases including in particular including those caused by papillomaviruses. Specifically, the invention provides compounds of Formula I:

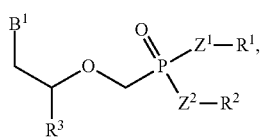

(I)

wherein: $B^1$ is a naturally occurring purine, a naturally occurring pyrimidine, a non-naturally occurring purine or a non-naturally occurring pyrimidine. In one embodiment, $B^1$ is selected from adenine, hypoxanthine, xanthine, theobromine, caffeine, uric acid, isoguanine, 2,6-diaminopurine, cytosine, thymine or uracil, guanine-7-yl, adenine-9-yl, cytosine-1-yl, thymin-1-yl, uracil-1-yl, 2,6-diaminopurin-9-yl, 5-fluorouracil, 5-fluorocytosine, 7-deazaguanine or 9-deazaguanine. In embodiments, B is selected from:

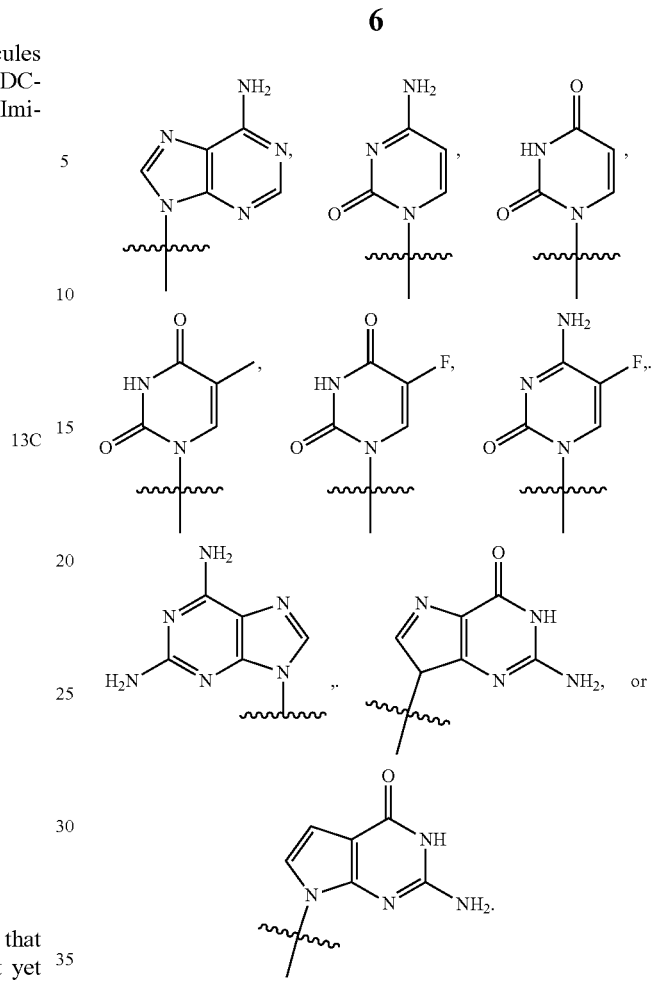

$Z^1$ and $Z^2$ are independently O or $NR^Z$. $R^Z$ is hydrogen or an optionally substituted $C_{1-4}$ alkyl. $R^1$ is an optionally substituted $-C_{2-24}$ alkenyl, an optionally substituted $-C_{2-24}$ alkynyl, an optionally substituted $-(CHR^4)_a-O-C_{2-24}$ alkenyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl), an optionally substituted heteroaryl, an optionally substituted heteroaryl($C_1$-$C_4$ alkyl)-, an optionally substituted heterocyclyl, an optionally substituted heterocyclyl($C_1$-$C_4$ alkyl)-,

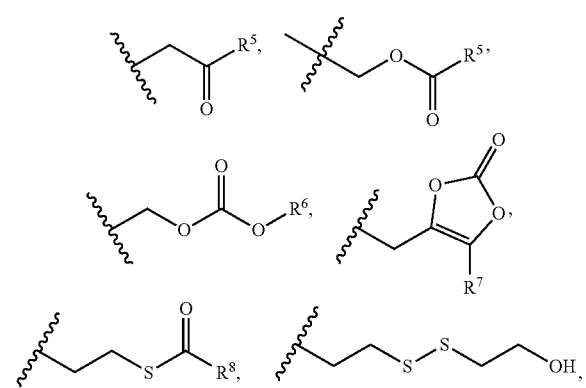

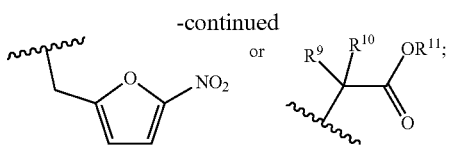

and $R^2$ is an optionally substituted —$C_{2-24}$ alkenyl, an optionally substituted —$C_{2-24}$ alkynyl, an optionally substituted —$(CHR^4)_b$—O—$C_{2-24}$ alkenyl, an optionally substituted cycloalkyl, an optionally substituted cycloalkyl($C_{1-4}$ alkyl)-, an optionally substituted cycloalkenyl, an optionally substituted cycloalkenyl($C_{1-4}$ alkyl)-, substituted aryl($C_{1-4}$ alkyl)-,

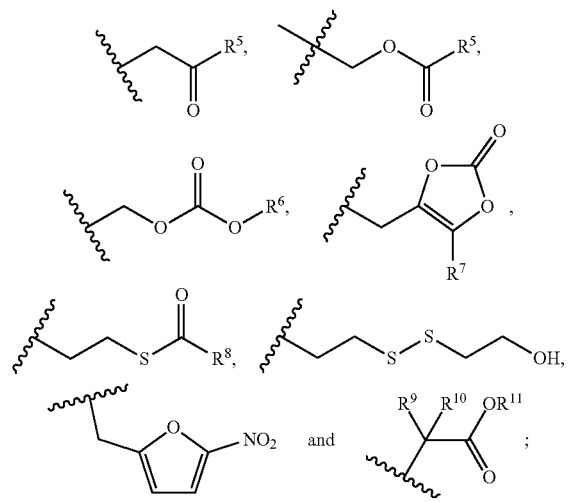

or $R^1$ and $R^2$ can be taken together to form a moiety selected from an optionally substituted

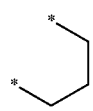 [SMILES: *CCC*]

or an optionally substituted

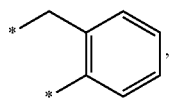

wherein $Z^1$, $Z^2$, $R^1$ and $R^2$, the phosphorus and the moiety form a six-membered to ten-membered ring system. $R^3$ is hydrogen, optionally substituted alkyl or optionally substituted heteroalkyl; each $R^4$ is independently hydrogen, —$(CH_2)_c$—S—$C_{1-24}$ alkyl or —O—$(CH_2)_d$—$R^{4A}$; each $R^{4A}$ is independently hydrogen, an optionally substituted $C_{1-24}$ alkyl or an optionally substituted aryl; each $R^5$, each $R^6$ and each $R^8$ are independently an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^7$ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^9$ and each $R^{10}$ are independently hydrogen or an optionally substituted $C_{1-6}$ alkyl; —$CH_2SH$, —$CH_2(C=O)NH_2$, —$CH_2CH_2(C=O)NH_2$, —$CH_2CH_2SCH_3$, $CH_2$— an optionally substituted phenyl, —$CH_2OH$, —$CH(OH)CH_3$,

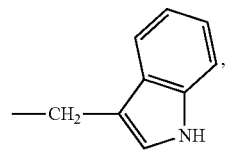

—$CH_2(C=O)OH$, —$CH_2CH_2(C=O)OH$, —$(CH_2)_3NH(C=NH)NH_2$,

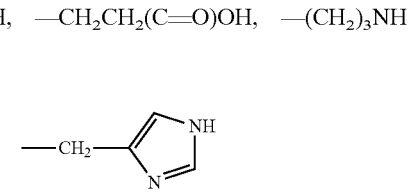

and —$(CH_2)_4NH_2$; each $R^{11}$ is independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each a and each b are independently 1, 2, 3 or 4; and each c and each d are independently 0, 1, 2 or 3.

In an alternative embodiment, when $B^1$ is

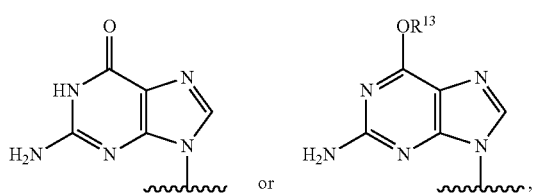

$R^{13}$ can be an unsubstituted $C_{1-6}$ alkyl or an unsubstituted $C_{3-6}$ cycloalkyl and $R^3$ can be selected from optionally substituted alkyl such as $CH_3$, $CH_2OH$, $CH_2F$, $CHF_2$, $CF_3$, or optionally substituted heteroalkyl such as $OCH_3$.

PMEG diphosphate is one of the most potent chain-terminating inhibitors of DNA polymerases alpha, delta and epsilon (Kramata P, Votruba I, Otová B, Holý A. Different inhibitory potencies of acyclic phosphonomethoxyalkyl nucleotide analogs toward DNA polymerases alpha, delta and epsilon. Mol Pharmacol. 1996 June; 49(6):1005-11. PubMed PMID: 8649338). However its inhibition of polymerases beta, gamma and epsilon is less pronounced. Pol delta and epsilon are involved in DNA repair and have exonuclease activity. Kramata et al have shown that PMEG-terminated primers cannot be repaired by pol delta (Kramata P, Downey KM, Paborsky LR. Incorporation and excision of 9-(2-phosphonylmethoxyethyl)guanine (PMEG) by DNA polymerase delta and epsilon in vitro. J Biol. Chem. 1998 Aug. 21; 273(34):21966-71. PubMed PMID: 9705337).

The mechanism of action of the antiviral compounds of the present invention that are metabolized to PMEG diphosphate is not known with certainty, however, it is possible that rapidly dividing epithelial cells cannot effectively repair PMEG terminated viral primers. Certain of the active compounds described herein release PMEG very slowly which tends to moderate intracellular levels of PMEG diphosphate, the active metabolite favoring antiviral activity and inhibition of HPV DNA synthesis, while higher intracellular levels of PMEG diphosphate (resulting from prodrugs that release PMEG diphosphate more quickly in the cell) lead to inhibition of cell division in a number of human cancers. This invention is based on the discovery that the anti-proliferative activity of the active metabolite PMEG diphosphate can be separated from the antiviral action of the active metabolite PMEG diphosphate by careful selection of the prodrug moiety to moderate the release rate of the active metabolite in the cell.

In embodiments, the invention describes compounds with antiviral activity against a papillomavirus in the absence of a significant anti-proliferative host cell effect.

The invention includes antiviral agents that selectively inhibit and/or block viral DNA synthesis and/or the production of virions of high risk HPV types. Inhibition and/or blockage of viral DNA synthesis and/or the production of virions of high risk HPV types can then eradicate the papillomavirus infection before cellular changes take place which can lead to invasive cancers, such as those described herein, and thus represent an advance in the art.

One embodiment of the invention provides an effective amount of an antiviral compound of Formula (I), or a pharmaceutically acceptable salt thereof, for treating a host infected with a human papillomavirus, by inhibiting the synthesis of viral DNA. Another embodiment disclosed herein is a method for treating a host infected with a human papillomavirus that includes contacting a cell infected with the human papillomavirus and/or administering to a subject infected with the human papillomavirus an effective amount of a compound of Formula (I), or a pharmaceutically acceptable salt thereof, wherein the human papillomavirus can be treated by selectively inhibiting viral replication by inhibiting the synthesis of viral DNA.

The present invention includes at least the following features:

(a) an antiviral compound of Formula I as described herein, and pharmaceutically acceptable salts and prodrugs thereof (each of which and all subgenera and species thereof considered individually and specifically described);

(b) an antiviral Formula I as described herein, and pharmaceutically acceptable salts and prodrugs thereof, for use in treating or preventing a viral infection such as papillomavirus in a host;

(c) use of Formula I, and pharmaceutically acceptable salts and prodrugs thereof in the manufacture of a medicament for use in treating or preventing a viral disease such as papillomavirus in a host;

(d) a process for manufacturing a medicament intended for the therapeutic use for treating or preventing treating or preventing a viral disease such as papillomavirus in a host further herein characterized in that Formula I as described herein is used in the manufacture;

(e) a pharmaceutical formulation comprising an effective host-treating amount of the Formula I or a pharmaceutically acceptable salt or prodrug thereof together with a pharmaceutically acceptable carrier or diluent;

(f) Formula I as described herein in substantially pure form, including substantially isolated from other chemical entities (e.g., at least 90 or 95%);

(g) processes for the manufacture of the compounds of Formula I and salts, compositions, dosage forms thereof; and (h) processes for the preparation of therapeutic products that contain an effective amount of Formula I, as described herein.

DETAILED DESCRIPTION OF THE INVENTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$ and $R^{13}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

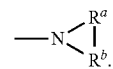

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$," "$C_a$—$C_b$," "$C_{a-b}$" and the like in which "a" and "b" are integers, refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refer to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heteroalicyclyl)alkyl" and "(heterocyclyl)alkyl" refer to a heterocyclic or a heteroalicylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aralkyl, (heteroaryl)alkyl or (heterocyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy, benzyloxy, hexadecyloxy and octadecyloxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heteroalicyclyl, aralkyl, heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R^A)$—" group wherein each X is a halogen, and $R^A$ is hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl.

The term "amino" as used herein refers to a "—$NH_2$" group.

As used herein, the term "hydroxy" refers to a "—OH" group.

A "cyano" group refers to a "—CN" group.

The term "azido" as used herein refers to a "—$N_3$" group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a "C=O" group.

An "S-sulfonamido" group refers to a "—$SO_2N(R^AR^B)$" group in which $R^A$ and $R^B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An S-sulfonamido may be substituted or unsubstituted.

An "N-sulfonamido" group refers to a "$RSO_2N(R^A)$—" group in which R and $R^A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-sulfonamido may be substituted or unsubstituted.

An "O-carbamyl" group refers to a "—OC(=O)N($R^AR^B$)" group in which $R^A$ and $R^B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An O-carbamyl may be substituted or unsubstituted.

An "N-carbamyl" group refers to an "ROC(=O)N($R^A$)—" group in which R and $R^A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-carbamyl may be substituted or unsubstituted.

An "O-thiocarbamyl" group refers to a "—OC(=S)—N($R^A R^B$)" group in which $R^A$ and $R^B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An O-thiocarbamyl may be substituted or unsubstituted.

An "N-thiocarbamyl" group refers to an "ROC(=S)N($R^A$)—" group in which R and $R^A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-thiocarbamyl may be substituted or unsubstituted.

A "C-amido" group refers to a "—C(=O)N($R^A R^B$)" group in which $R^A$ and $R^B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. A C-amido may be substituted or unsubstituted.

An "N-amido" group refers to a "RC(=O)N($R^A$)—" group in which R and $R^A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, the term "phosphonate" is used in its ordinary sense as understood by those skilled in the art, and includes its protonated forms
(for example,

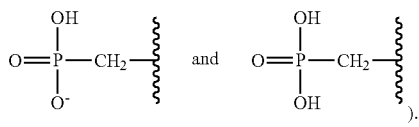

).

As used herein, the terms "monophosphonate" and "diphosphonate" are used in their ordinary sense as understood by those skilled in the art, and include protonated forms. Additionally, the term "phosphate" is used in its ordinary sense as understood by those skilled in the art, and includes its protonated forms (for example,

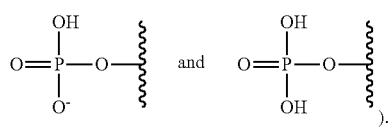

).

The terms "monophosphate," "diphosphate," and "triphosphate" are also used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of phosphonates and heterocyclic bases known in the art are intended to be included, including tautomers of natural and non-natural purine-bases and pyrimidine-bases are intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

As used herein, a "subject" refers to an animal that is a host for a viral infection as described herein. "Animal" includes a mammal. "Mammals" includes, without limitation, mice, rats, rabbits, guinea pigs, dogs, cats, sheep, goats, cows, horses, primates, such as monkeys, chimpanzees, and apes, and, in particular, humans. In a typical embodiment, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Some embodiments disclosed herein include the use of an effective amount of a compound of Formula (I), or a pharmaceutically acceptable salt thereof, in the preparation of a medicine for treating a host infected with a human papillomavirus, by inhibiting the synthesis of viral DNA. Other embodiments disclosed herein include the use of an effective amount of a compound of Formula (I), or a pharmaceutically acceptable salt thereof, for treating a host infected with a human papillomavirus, wherein the human papillomavirus can be ameliorated by inhibiting the synthesis of viral DNA. Still other embodiments disclosed herein include a method for treating a host infected with a human papillomavirus that can include contacting a cell infected with the human papillomavirus in a subject infected with the human papillomavirus with an effective amount of a compound of Formula (I), or a pharmaceutically acceptable salt thereof. Yet still other embodiments disclosed herein include a method for treating a host infected with a human papillomavirus that can includes administering to a subject infected with the human papillomavirus an effective amount of a compound of Formula (I), or a pharmaceutically acceptable salt thereof, by inhibiting the synthesis of viral DNA. Some embodiments disclosed herein include compound of Formula (I), or a pharmaceutically acceptable salt thereof, for use treating a host infected with a human papillomavirus, by inhibiting viral replication by inhibiting the synthesis of viral DNA.

In some embodiments, the human papillomavirus can be a high-risk human papillomavirus, such as those described herein. For example, the high-risk human papillomavirus can be selected from HPV-16, HPV-18, HPV-31, HPV-33, HPV-35, HPV-39, HPV-45, HPV-51, HPV-52, HPV-56, HPV-58, HPV-59, HPV-68, HPV-73 and HPV-82. In some embodiments, the human papillomavirus can be HPV-16. In some embodiments, the human papillomavirus can be HPV-18. In some embodiments, the human papillomavirus can be one or more of the following high-risk types: HPV-31, HPV-33, HPV-35, HPV-39, HPV-45, HPV-51, HPV-52, HPV-56, HPV-58, HPV-59, HPV-68, HPV-73 and HPV-82. As described herein, the presence of a HPV infection can be detected using a PAP smear and/or DNA probe testing (for example, HPV DNA probe testing for one or more high-risk HPV types). Therefore, in some embodiments, an effective amount of a compound of Formula (I), or a pharmaceutically acceptable salt thereof, can be provided to a subject diagnosed with a HPV infection, for example a high-risk HPV infection, by a DNA test, such as one of the HPV DNA tests described herein.

In some embodiments, the human papillomavirus can be a low-risk human papillomavirus, including those described herein. In some embodiments, the human papillomavirus can be HPV-6. In some embodiments, the human papillomavirus can be HPV-11.

A compound of Formula (I), or a pharmaceutically acceptable salt thereof, can be used to treat a host infected with one or more types of human papillomaviruses. For example, a compound of Formula (I), or a pharmaceutically acceptable salt thereof, can be used to treat HPV-16 and HPV-18. In some embodiments, a compound of Formula (I), or a pharmaceutically acceptable salt thereof, can be used to treat both high-risk and low-risk HPV.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. For a topical or intravaginal administration, the dose may be between 0.02 mg to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of another agent. In some embodiments, the total time of the treatment regime with a compound of Formula (I), or a pharmaceutically acceptable salt thereof, can less compared to the total time of the treatment regime with another agent.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, a compound of Formula (I), or a pharmaceutically acceptable salt thereof, can have a moiety(ies) that neutralize the charge of the phosphonate. By neutralizing the charge on the phosphonate, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphonate thus released may then be metabolized by cellular enzymes to the monophosphate or to the diphosphate, the active metabolite. Furthermore, in some embodiments, varying the substituents on a compound described herein, such as a compound of Formula (I), or a pharmaceutically acceptable salt thereof, can help maintain the efficacy of the compound by reducing undesirable effects, such as isomerization.

In some embodiments, a compound of Formula (I), or a pharmaceutically acceptable salt thereof, can act as a chain terminator of DNA synthesis. Once the compound is incorporated into a DNA chain, no further elongation is observed to occur. In some embodiments, a compound of Formula (I) or a pharmaceutically acceptable salt thereof, is metabolized such that the groups attached to the phosphorus atom are removed to generate a phosphonic acid. The phosphonic acid can then be anabolized to a diphosphate, the active metabolite, that can act as a chain terminator of DNA synthesis. Once the compound is incorporated into a DNA chain, no further elongation is observed to occur.

Additionally, in some embodiments, the presence of a moiety(ies) that neutralizes the charge of the phosphonate can increase the stability of the compound by inhibiting its degradation. Also, in some embodiments, the presence of a moiety(ies) that neutralizes the charge of the phosphonate can make the compound more resistant to cleavage in vivo and provide sustained, extended efficacy. In some embodiments, a moiety(ies) that neutralizes the charge of the phosphonate can facilitate the penetration of the cell membrane by a compound of Formula (I) by making the compound more lipophilic. In some embodiments, a moiety(ies) that neutralizes the charge of the phosphonate can have improved oral bioavailability, improved aqueous stability and/or reduced risk of byproduct-related toxicity.

Compounds

In a first embodiment disclosed herein are a compound of Formula (I), or a pharmaceutically acceptable salt thereof:

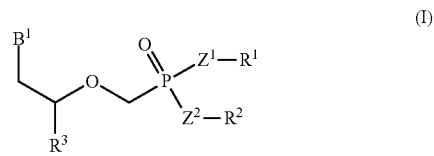

wherein: $B^1$ is a naturally occurring purine, a naturally occurring pyrimidine, a non-naturally occurring purine or a non-naturally occurring pyrimidine. The term naturally occurring purine or pyrimidine base includes guanine, adenine, hypoxanthine, xanthine, theobromine, caffeine, uric acid, isoguanine, 2,6-diaminopurine, cytosine, thymine or uracil, wherein the acyclic chain is bonded to the N as normally occurring in nature. Attachment of the naturally occurring purine or pyrimidine base can be at any available site, e.g., guanin-9-yl, guanine-7-yl, adenine-9-yl, cytosine-1-yl, thymin-1-yl, uracil-1-yl, 2,6-diaminopurin-9-yl. The term "non-naturally occurring" purine or pyrimidine refers to purine or pyrimidine not found in nature, for example, 5-fluorouracil, 5-fluorocytosine, 7-deazaguanine and 9-deazaguanine.

In nonlimiting embodiments, $B^1$ can be:

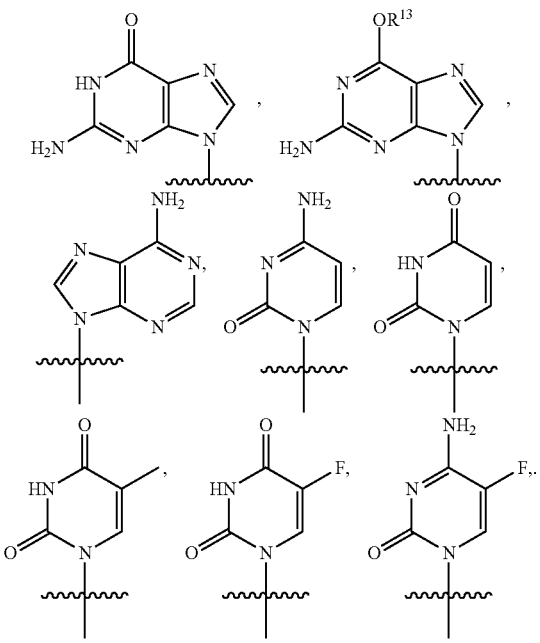

-continued

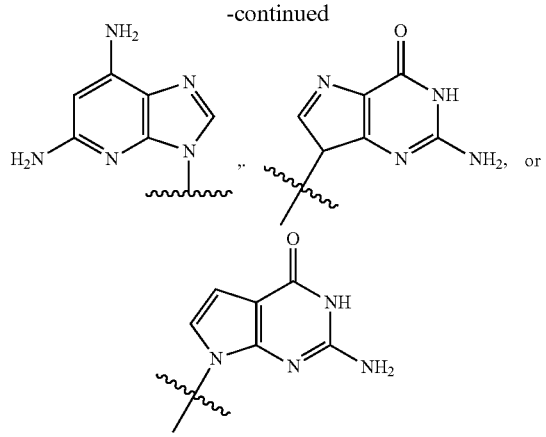

wherein R$^{13}$ can be an unsubstituted C$_{1-6}$ alkyl or an unsubstituted C$_{3-6}$ cycloalkyl. In some embodiments, R$^{13}$ can be methyl, ethyl, n-propyl, isopropyl, n-butyl, isobutyl, tert-butyl, pentyl (branched or straight chained) or hexyl (branched or straight chained). In other embodiments, R$^{13}$ can be cyclopropyl, cyclobutyl, cyclopentyl or cyclohexyl. In other embodiments, B$^1$ can be adenine, cytosine, thymine, uracil, 2,6-diaminopurine, 7-deazapurine or 9-deazapurine. Z$^1$ and Z$^2$ can be independently O (oxygen) or NR$^Z$, wherein R$^Z$ can be H (hydrogen) or an optionally substituted C$_{1-4}$ alkyl; wherein when Z$^1$ and Z$^2$ are each independently O (oxygen); R$^1$ can be selected from, an optionally substituted —C$_{2-24}$ alkenyl, an optionally substituted —C$_{2-24}$ alkynyl, an optionally substituted —(CHR$^4$)$_a$—O—C$_{2-24}$ alkenyl, an optionally substituted cycloalkyl, an optionally substituted cycloalkyl(C$_1$-C$_4$ alkyl)-, an optionally substituted cycloalkenyl, an optionally substituted cycloalkenyl(C$_1$-C$_4$ alkyl)-, an optionally substituted aryl, an optionally substituted aryl(C$_{1-4}$ alkyl), an optionally substituted heteroaryl, an optionally substituted heteroaryl(C$_1$-C$_4$ alkyl)-, an optionally substituted heterocyclyl, an optionally substituted heterocyclyl(C$_1$-C$_4$ alkyl)-,

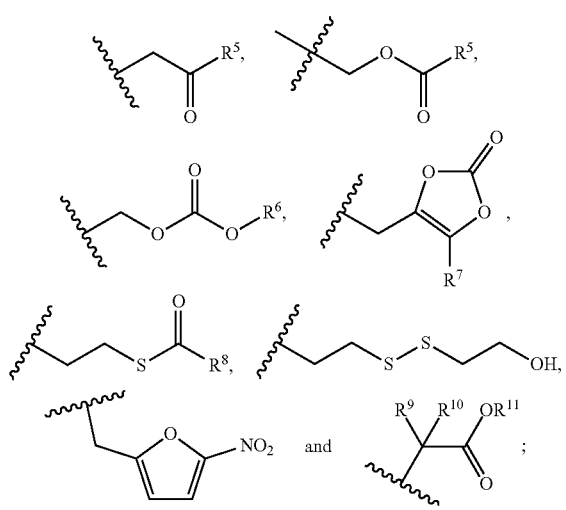

R$^2$ can be selected from, an optionally substituted —C$_{2-24}$ alkenyl, an optionally substituted —C$_{2-24}$ alkynyl, an optionally substituted —(CHR$^4$)$_b$—O—C$_{2-24}$ alkenyl, an optionally substituted cycloalkyl, an optionally substituted cycloalkyl(C$_{1-4}$ alkyl)-, an optionally substituted cycloalkenyl, an optionally substituted cycloalkenyl(C$_{1-4}$ alkyl)-, substituted aryl(C$_{1-4}$ alkyl)-,

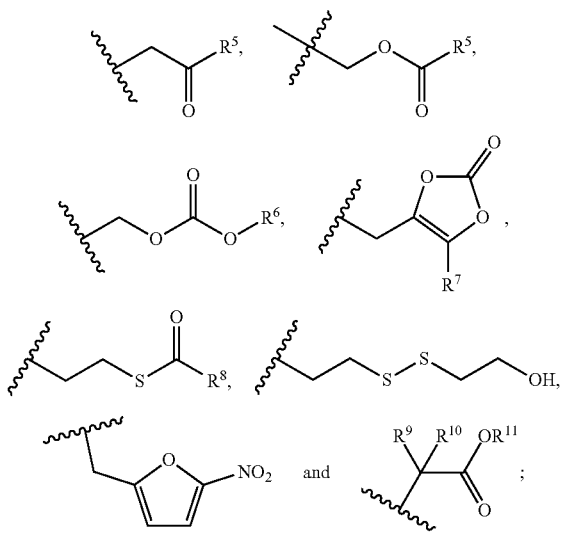

when Z$^1$ and Z$^2$ are each independently O; R$^1$ and R$^2$ can be taken together to form a moiety selected from an optionally substituted

or an optionally substitute

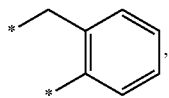

wherein Z$^1$, Z$^2$, R$^1$ and R$^2$, the phosphorus and the moiety form a six-membered to ten-membered ring system; or one of Z$^1$ and Z$^2$ can be independently O (oxygen) and the other Z$^1$ or Z$^2$ group is NR$^Z$, wherein R$^Z$ can be H (hydrogen) or an optionally substituted C$_{1-4}$ alkyl; or Z$^1$ and Z$^2$ are each NR$^Z$, wherein R$^Z$ can be H (hydrogen) or an optionally substituted C$_{1-4}$ alkyl; wherein: R$^1$ and R$^2$ can each be independently selected from an optionally substituted —C$_{1-24}$ alkyl, an optionally substituted —C$_{2-24}$ alkenyl, an optionally substituted —C$_{2-24}$ alkynyl, an optionally substituted —(CHR$^4$)$_a$—O—C$_{1-24}$ alkyl, an optionally substituted —(CHR$^4$)$_b$—O—C$_{2-24}$ alkenyl, an optionally substituted —(CHR$^4$)$_b$—O—C$_{2-24}$ alkynyl, an optionally substituted cycloalkyl, an optionally substituted cycloalkyl(C$_1$-C$_4$ alkyl)-, an optionally substituted cycloalkenyl, an optionally substituted cycloalkenyl(C$_1$-C$_4$ alkyl)-, an optionally substituted aryl, a substituted aryl(C$_{1-4}$ alkyl), an optionally substituted heteroaryl, an optionally substituted heteroaryl(C$_1$-C$_4$ alkyl)-, an optionally substituted heterocyclyl, an optionally substituted heterocyclyl(C$_1$-C$_4$ alkyl)-,

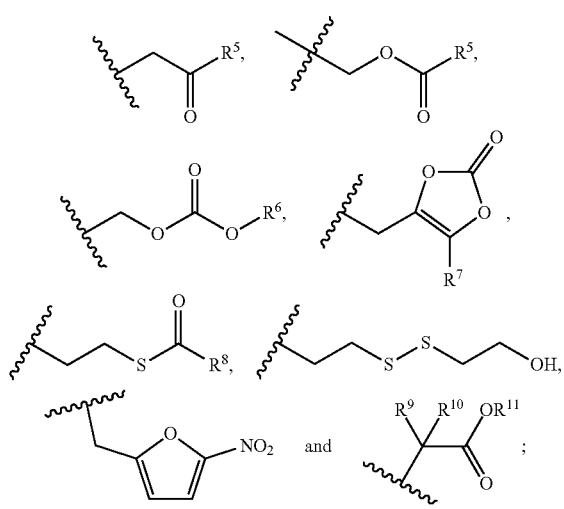

when one of $Z^1$ or $Z^2$ is O; and the other $Z^1$ or $Z^2$ group is $NR^Z$ or both of $Z^1$ and $Z^2$ is $NR^Z$; $R^1$ and $R^2$ can be taken together to form a moiety selected from an optionally substituted

or an optionally substituted

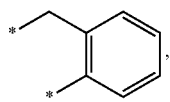

wherein $Z^1$, $Z^2$, $R^1$ and $R^2$, the phosphorus and the moiety form a six-membered to ten-membered ring system; $R^3$ can be selected from hydrogen, optionally substituted alkyl such as $CH_3$, $CH_2OH$, $CH_2F$, $CHF_2$, $CF_3$, or optionally substituted heteroalkyl such as $OCH_3$; each $R^4$ can be independently hydrogen, $-(CH_2)_c-S-C_{1-24}$ alkyl or $-O-(CH_2)_d-R^{4.4}$; each $R^{4.4}$ can be hydrogen, an optionally substituted $C_{1-24}$ alkyl or an optionally substituted aryl; each $R^5$, each $R^6$ and each $R^8$ can be independently an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^7$ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^9$ and each $R^{10}$ can be independently hydrogen or an optionally substituted $C_{1-6}$ alkyl; $-CH_2SH$, $-CH_2(C=O)NH_2$, $-CH_2CH_2(C=O)NH_2$, $-CH_2CH_2S\ CH_3$, $CH_2$-an optionally substituted phenyl, $-CH_2OH$, $-CH(OH)CH_3$,

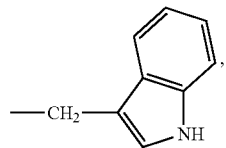

$-CH_2(C=O)OH$, $-CH_2CH_2(C=O)OH$, $-(CH_2)_3NH(C=NH)NH_2$,

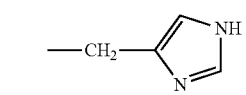

and $-(CH_2)_4NH_2$; each $R^{11}$ can be independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each a and each b can be independently 1, 2, 3 or 4; each c and each d can be independently 0, 1, 2 or 3.

In embodiments, when $B^1$ is

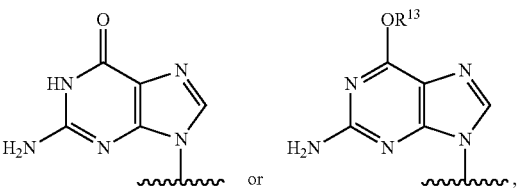

$R^3$ can be selected from optionally substituted alkyl such as $CH_3$, $CH_2OH$, $CH_2F$, $CHF_2$, $CF_3$, or optionally substituted heteroalkyl such as $OCH_3$.

In embodiments, compounds are disclosed having Formula Ia:

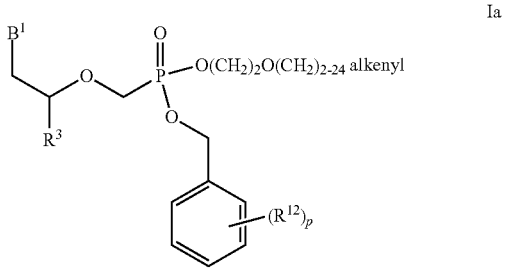

wherein: $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; p=1, 2, 3, 4 or 5; and $B^1$ and $R^3$ are as defined above.

In embodiments, compounds are disclosed having Formula Ib:

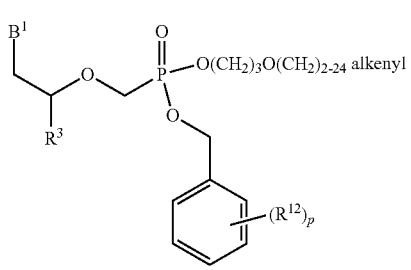

Ib wherein: $B^1$, $R^3$, $R^{12}$ and p are as defined above.

In embodiments, compounds are disclosed having Formula Ic:

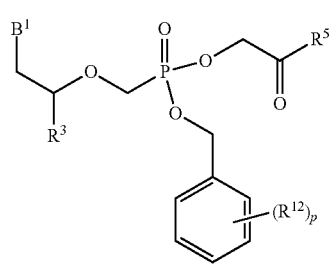

Ic wherein: $B^1$, $R^3$, $R^5$, $R^{12}$ and p are as defined above.

In embodiments, compounds are disclosed having Formula Id:

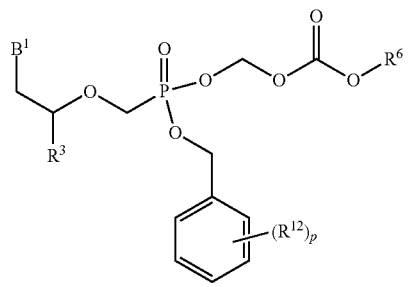

Id wherein: $B^1$, $R^3$, $R^6$, $R^{12}$ and p are as defined above.

In embodiments, compounds are disclosed having Formula Ie:

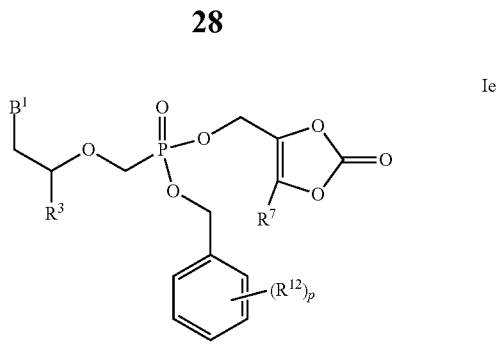

Ie wherein: $B^1$, $R^3$, $R^7$, $R^{12}$ and p are as defined above.

In embodiments, compounds are disclosed having Formula If:

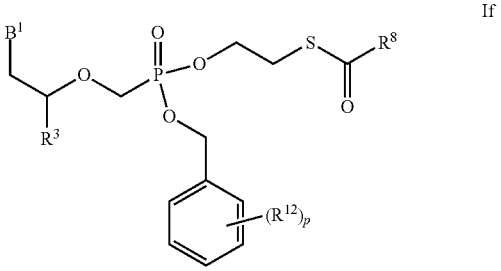

If wherein: $B^1$, $R^3$, $R^8$, $R^{12}$ and p are as defined above.

In embodiments, compounds are disclosed having Formula Ig:

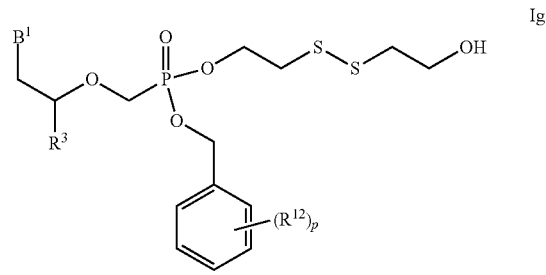

Ig wherein: $B^1$, $R^3$, $R^{12}$ and p are as defined above.

In embodiments, compounds are disclosed having Formula Ih:

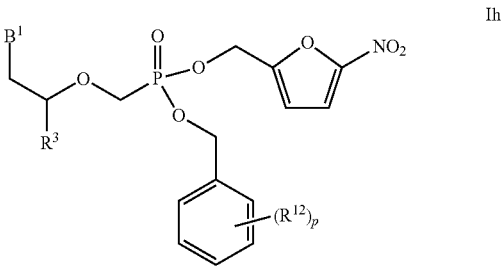

Ih wherein: $B^1$, $R^3$, $R^{12}$ and p are as defined above.

In embodiments, compounds are disclosed having Formula Ii:

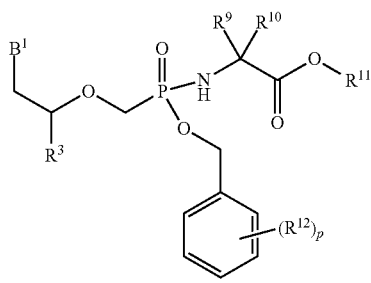

Ii wherein: $B^1$, $R^3$, $R^9$, $R^{10}$, $R^{11}$, $R^{12}$ and p are as defined above.

In embodiments, compounds are disclosed having Formula Ij:

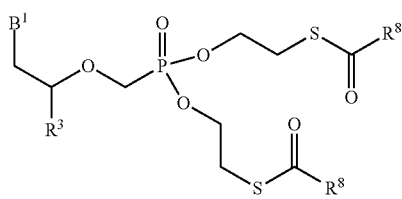

Ij wherein: $B^1$, $R^3$, and $R^8$ are as defined above.

In embodiments, compounds are disclosed having Formula Ik:

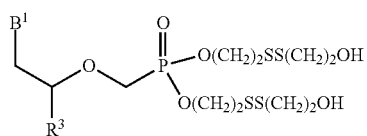

Ik wherein: $B^1$ and $R^3$ are as defined above.

In embodiments, compounds are disclosed having Formula Il:

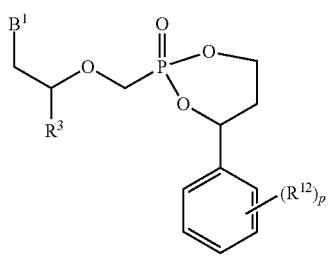

Il wherein: $B^1$, $R^3$, $R^{12}$ and p are as defined above.

In an alternate embodiment, compounds are disclosed having Formula Im:

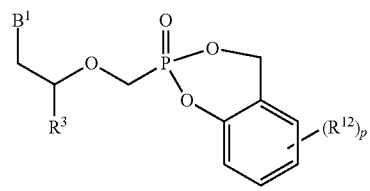

Im wherein: $B^1$, $R^3$, $R^{12}$ and p are as defined above.

Some embodiments of a compound of Formula (I), or a pharmaceutically acceptable salt thereof, are provided in Table 1. In Table 1,

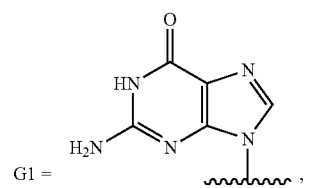

G1 =

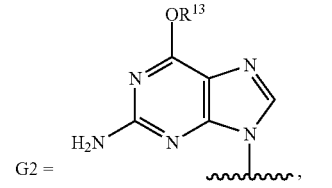

G2 =

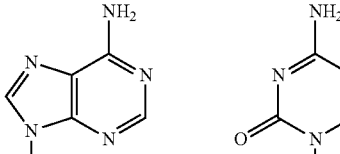

G3 = , G4 = and

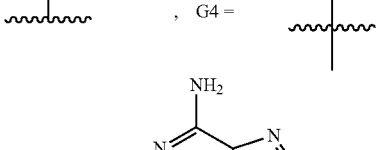

G5 =

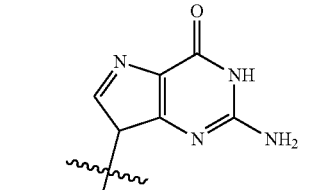

G6 = ,

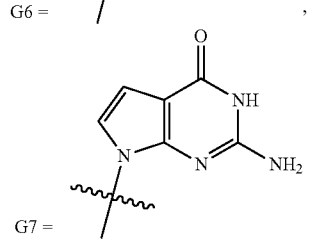

G7 =

TABLE 1

| B¹ | Z¹ | Z² | R¹ | R¹ |
|---|---|---|---|---|
| G1 | O | O | —$C_{2-24}$ alkenyl | —$C_{12-24}$ alkenyl |
| G1 | O | O | —$C_{2-24}$ alkynyl | —$C_{12-24}$ alkenyl |
| G1 | O | O | —$(CH_2)_2O$—$C_{2-24}$ alkenyl | —$C_{12-24}$ alkenyl |
| G1 | O | O | Cycloalkyl | —$C_{12-24}$ alkenyl |
| G1 | O | O | cycloalkyl($C_{1-4}$ alkyl)- | —$C_{12-24}$ alkenyl |
| G1 | O | O | Cycloalkenyl | —$C_{12-24}$ alkenyl |
| G1 | O | O | cycloalkenyl($C_{1-4}$ alky) | —$C_{12-24}$ alkenyl |
| G1 | O | O | Aryl | —$C_{12-24}$ alkenyl |
| G1 | O | O | aryl($C_{1-4}$ alky) | —$C_{12-24}$ alkenyl |
| G1 | O | O | Heteroaryl | —$C_{12-24}$ alkenyl |
| G1 | O | O | heteroaryl($C_{1-4}$ alky) | —$C_{12-24}$ alkenyl |
| G1 | O | O | —$C_{2-24}$ alkenyl | —$(CH_2)_2O$—$C_{2-24}$ alkenyl |
| G1 | O | O | —$C_{2-24}$ alkynyl | —$(CH_2)_2O$—$C_{2-24}$ alkenyl |
| G1 | O | O | —$(CH_2)_2O$—$C_{2-24}$ alkenyl | —$(CH_2)_2O$—$C_{2-24}$ alkenyl |
| G1 | O | O | Cycloalkyl | —$(CH_2)_2O$—$C_{2-24}$ alkenyl |
| G1 | O | O | cycloalkyl($C_{1-4}$ alkyl)- | —$(CH_2)_2O$—$C_{2-24}$ alkenyl |
| G1 | O | O | Cycloalkenyl | —$(CH_2)_2O$—$C_{2-24}$ alkenyl |
| G1 | O | O | cycloalkenyl($C_{1-4}$ alkyl) | —$(CH_2)_2O$—$C_{2-24}$ alkenyl |
| G1 | O | O | Aryl | —$(CH_2)_2O$—$C_{2-24}$ alkenyl |
| G1 | O | O | aryl($C_{1-4}$ alkyl) | —$(CH_2)_2O$—$C_{2-24}$ alkenyl |
| G1 | O | O | Heteroaryl | —$(CH_2)_2O$—$C_{2-24}$ alkenyl |
| G1 |   | O | heteraroyl($C_{1-4}$ alkyl) | —$(CH_2)_2O$—$C_{2-24}$ alkenyl |
| G1 | O | O | ~~CH₂C(=O)R⁵~~ | ~~CH₂C(=O)R⁵~~ |
| G1 | O | O | ~~(CH₂)₂SC(=O)R⁸~~ | ~~(CH₂)₂SC(=O)R⁸~~ |
| G1 | O | O | ~~(CH₂)₂SSCH₂CH₂OH~~ | ~~(CH₂)₂SSCH₂CH₂OH~~ |
| G1 | O | O | ~~CH₂-(5-nitrofuran-2-yl)~~ | ~~CH₂-(5-nitrofuran-2-yl)~~ |
| G1 | NCH₃ | O | —$(CH_2)_3CH_2Cl$ | ~~CH₂-(5-nitrofuran-2-yl)~~ |
| G1 | ++ | O | —$(CH_2)_3CH_2Cl$ | ~~CH₂-(5-nitrofuran-2-yl)~~ |
| G1 | O | O | *—(CH₂)₃—* (linker) | |
| G1 | O | O | *—CH₂-(o-phenylene)—* (linker) | |
| G2 | O | O | —$C_{2-24}$ alkenyl | —$C_{12-24}$ alkenyl |
| G2 | O | O | —$C_{2-24}$ alkynyl | —$C_{12-24}$ alkenyl |
| G2 | O | O | —$(CH_2)_2O$—$C_{2-24}$ alkenyl | —$C_{12-24}$ alkenyl |
| G2 | O | O | Cycloalkyl | —$C_{12-24}$ alkenyl |
| G2 | O | O | cycloalkyl($C_{1-4}$ alkyl)- | —$C_{12-24}$ alkenyl |
| G2 | O | O | Cycloalkenyl | —$C_{12-24}$ alkenyl |

TABLE 1-continued

| B¹ | Z¹ | Z² | R¹ | R¹ |
|---|---|---|---|---|
| G2 | O | O | cycloalkenyl(C$_{1-4}$ alkyl) | —C$_{12-24}$ alkenyl |
| G2 | O | O | Aryl | —C$_{12-24}$ alkenyl |
| G2 | O | O | aryl(C$_{1-4}$ alkyl) | —C$_{12-24}$ alkenyl |
| G2 | O | O | Heteroaryl | —C$_{12-24}$ alkenyl |
| G2 | O | O | heteroaryl(C$_{1-4}$ alkyl) | —C$_{12-24}$ alkenyl |
| G2 | O | O | —C$_{2-24}$ alkenyl | —(CH$_2$)$_2$O—C$_{2-24}$ alkenyl |
| G2 | O | O | —C$_{2-24}$ alkynyl | —(CH$_2$)$_2$O—C$_{2-24}$ alkenyl |
| G2 | O | O | —(CH$_2$)$_2$O—C$_{2-24}$ alkenyl | —(CH$_2$)$_2$O—C$_{2-24}$ alkenyl |
| G2 | O | O | Cycloalkyl | —(CH$_2$)$_2$O—C$_{2-24}$ alkenyl |
| G2 | O | O | cycloalkyl(C$_{1-4}$ alkyl)- | —(CH$_2$)$_2$O—C$_{2-24}$ alkenyl |
| G2 | O | O | Cycloalkenyl | —(CH$_2$)$_2$O—C$_{2-24}$ alkenyl |
| G2 | O | O | cycloalkenyl(C$_{1-4}$ alkyl) | —(CH$_2$)$_2$O—C$_{2-24}$ alkenyl |
| G2 | O | O | Aryl | —(CH$_2$)$_2$O—C$_{2-24}$ alkenyl |
| G2 | O | O | aryl(C$_{1-4}$ alkyl) | —(CH$_2$)$_2$O—C$_{2-24}$ alkenyl |
| G2 | O | O | Heteroaryl | —(CH$_2$)$_2$O—C$_{2-24}$ alkenyl |
| G2 | O | O | heteroaryl(C$_{1-4}$ alkyl) | —(CH$_2$)$_2$O—C$_{2-24}$ alkenyl |
| G2 | O | O | [structure: —CH$_2$—C(=O)—R$^5$] | [structure: —CH$_2$—C(=O)—R$^5$] |
| G2 | O | O | [structure: —(CH$_2$)$_2$—S—C(=O)—R$^8$] | [structure: —(CH$_2$)$_2$—S—C(=O)—R$^8$] |
| G2 | O | O | [structure: —(CH$_2$)$_2$—S—S—CH$_2$CH$_2$OH] | [structure: —(CH$_2$)$_2$—S—S—CH$_2$CH$_2$OH] |
| G2 | O | O | [structure: —CH$_2$-(5-nitrofuran-2-yl)] | [structure: —CH$_2$-(5-nitrofuran-2-yl)] |
| G2 | NCH$_3$ | O | —(CH$_2$)$_3$CH$_2$Cl | [structure: —CH$_2$-(5-nitrofuran-2-yl)] |
| G2 | ++ | O | —(CH$_2$)$_3$CH$_2$Cl | [structure: —CH$_2$-(5-nitrofuran-2-yl)] |
| G2 | O | O | [structure: butylene linker with two * attachment points] | |
| G2 | O | O | [structure: ortho-xylylene linker with two * attachment points] | |
| G3 | O | O | —C$_{2-24}$ alkenyl | —C$_{12-24}$ alkenyl |
| G3 | O | O | —C$_{2-24}$ alkynyl | —C$_{12-24}$ alkenyl |
| G3 | O | O | —(CH$_2$)$_2$O—C$_{2-24}$ alkenyl | —C$_{12-24}$ alkenyl |
| G3 | O | O | Cycloalkyl | —C$_{12-24}$ alkenyl |
| G3 | O | O | cycloalkyl(C$_{1-4}$ alkyl)- | —C$_{12-24}$ alkenyl |
| G3 | O | O | Cycloalkenyl | —C$_{12-24}$ alkenyl |
| G3 | O | O | cycloalkenyl(C$_{1-4}$ alkyl) | —C$_{12-24}$ alkenyl |
| G3 | O | O | Aryl | —C$_{12-24}$ alkenyl |
| G3 | O | O | aryl(C$_{1-4}$ alkyl) | —C$_{12-24}$ alkenyl |
| G3 | O | O | Heteroaryl | —C$_{12-24}$ alkenyl |
| G3 | O | O | heteroaryl(C$_{1-4}$ alkyl) | —C$_{12-24}$ alkenyl |
| G3 | O | O | —C$_{2-24}$ alkenyl | —(CH$_2$)$_2$O—C$_{2-24}$ alkenyl |

TABLE 1-continued

| B¹ | Z¹ | Z² | R¹ | R¹ |
|---|---|---|---|---|
| G3 | O | O | —$C_{2-24}$ alkynyl | —$(CH_2)_2O$—$C_{2-24}$ alkenyl |
| G3 | O | O | —$(CH_2)_2O$—$C_{2-24}$ alkenyl | —$(CH_2)_2O$—$C_{2-24}$ alkenyl |
| G3 | O | O | Cycloalkyl | —$(CH_2)_2O$—$C_{2-24}$ alkenyl |
| G3 | O | O | cycloalkyl($C_{1-4}$ alkyl)- | —$(CH_2)_2O$—$C_{2-24}$ alkenyl |
| G3 | O | O | Cycloalkenyl | —$(CH_2)_2O$—$C_{2-24}$ alkenyl |
| G3 | O | O | cycloalkenyl($C_{-14}$ alky) | —$(CH_2)_2O$—$C_{2-24}$ alkenyl |
| G3 | O | O | Aryl | —$(CH_2)_2O$—$C_{2-24}$ alkenyl |
| G3 | O | O | aryl($C_{1-4}$ alkyl) | —$(CH_2)_2O$—$C_{2-24}$ alkenyl |
| G3 | O | O | Heteroaryl | —$(CH_2)_2O$—$C_{2-24}$ alkenyl |
| G3 | O | O | heteroaryl($C_{1-4}$ alkyl) | —$(CH_2)_2O$—$C_{2-24}$ alkenyl |
| G3 | O | O | [structure with $R^5$ and C=O] | [structure with $R^5$ and C=O] |
| G3 | O | O | [structure with S—C(=O)—$R^8$] | [structure with S—C(=O)—$R^8$] |
| G3 | O | O | [structure with S—S—CH₂CH₂OH] | [structure with S—S—CH₂CH₂OH] |
| G3 | O | O | [5-nitrofuran structure] | [5-nitrofuran structure] |
| G3 | NCH₃ | O | —$(CH_2)_3CH_2Cl$ | [5-nitrofuran structure] |
| G3 | ++ | O | —$(CH_3)_3CH_2Cl$ | [5-nitrofuran structure] |
| G3 | O | O | | [alkyl chain structure with *] |
| G3 | O | O | | [ortho-disubstituted benzyl structure with *] |
| G4 | O | O | —$C_{2-24}$ alkenyl | —$C_{12-24}$ alkenyl |
| G4 | O | O | —$C_{2-24}$ alkynyl | —$C_{12-24}$ alkenyl |
| G4 | O | O | —$(CH_2)_2O$—$C_{2-24}$ alkenyl | —$C_{12-24}$ alkenyl |
| G4 | O | O | Cycloalkyl | —$C_{12-24}$ alkenyl |
| G4 | O | O | cycloalkyl($C_{1-4}$ alkyl)- | —$C_{12-24}$ alkenyl |
| G4 | O | O | Cycloalkenyl | —$C_{12-24}$ alkenyl |
| G4 | O | O | cycloalkenyl($C_{1-4}$ alkyl) | —$C_{12-24}$ alkenyl |
| G4 | O | O | Aryl | —$C_{12-24}$ alkenyl |
| G4 | O | O | aryl($C_{1-4}$ alkyl) | —$C_{12-24}$ alkenyl |
| G4 | O | O | Heteroaryl | —$C_{12-24}$ alkenyl |
| G4 | O | O | heteroaryl($C_{1-4}$ alkyl) | —$C_{12-24}$ alkenyl |
| G4 | O | O | —$C_{2-24}$ alkenyl | —$(CH_2)_2O$—$C_{2-24}$ alkenyl |
| G4 | O | O | —$C_{2-24}$ alkynyl | —$(CH_2)_2O$—$C_{2-24}$ alkenyl |
| G4 | O | O | —$(CH_2)_2O$—$C_{2-24}$ alkenyl | —$(CH_2)_2O$—$C_{2-24}$ alkenyl |
| G4 | O | O | Cycloalkyl | —$(CH_2)_2O$—$C_{2-24}$ alkenyl |
| G4 | O | O | cycloalkyl($C_{1-4}$ alkyl)- | —$(CH_2)_2O$—$C_{2-24}$ alkenyl |
| G4 | O | O | cycloalkenyl | —$(CH_2)_2O$—$C_{2-24}$ alkenyl |
| G4 | O | O | cycloalkenyl($C_{1-4}$ alkyl) | —$(CH_2)_2O$—$C_{2-24}$ alkenyl |

TABLE 1-continued

| $B^1$ | $Z^1$ | $Z^2$ | $R^1$ | $R^1$ |
|---|---|---|---|---|
| G4 | O | O | Aryl | —(CH$_2$)$_2$O—C$_{2-24}$ alkenyl |
| G4 | O | O | aryl(C$_{1-4}$ alkyl) | —(CH$_2$)$_2$O—C$_{2-24}$ alkenyl |
| G4 | O | O | Heteroaryl | —(CH$_2$)$_2$O—C$_{2-24}$ alkenyl |
| G4 | O | O | heteroaryl(C$_{1-4}$ alkyl) | —(CH$_2$)$_2$O—C$_{2-24}$ alkenyl |
| G4 | O | O | 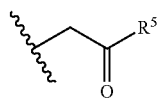 | 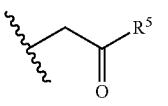 |
| G4 | O | O | 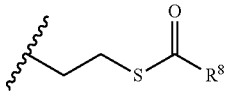 | 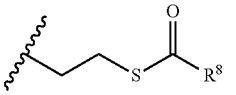 |
| G4 | O | O | 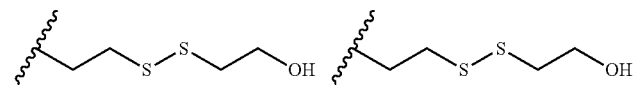 | 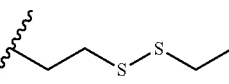 |
| G4 | O | O | 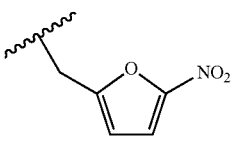 [SMILES: *Cc1ccc([N+](=O)[O-])o1] | 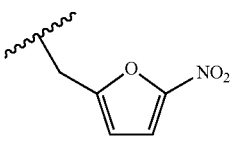 |
| G4 | NCH$_3$ | O | —(CH$_2$)$_3$CH$_2$Cl | 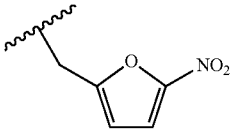 [SMILES: *Cc1ccc([N+](=O)[O-])o1] |
| G4 | ++ | O | —(CH$_2$)$_3$CH$_2$Cl | 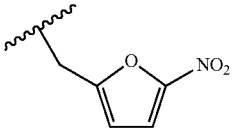 |
| G4 | O | O | | 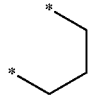 |
| G4 | O | O | | 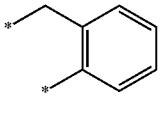 |
| G5 | O | O | —C$_{2-24}$ alkenyl | —C$_{12-24}$ alkenyl |
| G5 | O | O | —C$_{2-24}$ alkynyl | —C$_{12-24}$ alkenyl |
| G5 | O | O | —(CH$_2$)$_2$O—C$_{2-24}$ alkenyl | —C$_{12-24}$ alkenyl |
| G5 | O | O | cycloalkyl | —C$_{12-24}$ alkenyl |
| G5 | O | O | cycloalkyl(C$_{1-4}$ alkyl)- | —C$_{12-24}$ alkenyl |
| G5 | O | O | cycloalkenyl | —C$_{12-24}$ alkenyl |
| G5 | O | O | cycloalkenyl(C$_{1-4}$ alkyl) | —C$_{12-24}$ alkenyl |
| G5 | O | O | Aryl | —C$_{12-24}$ alkenyl |
| G5 | O | O | aryl(C$_{1-4}$ alkyl) | —C$_{12-24}$ alkenyl |
| G5 | O | O | Heteroaryl | —C$_{12-24}$ alkenyl |
| G5 | O | O | heteroaryl(C$_{1-4}$ alkyl) | —C$_{12-24}$ alkenyl |
| G5 | O | O | —C$_{2-24}$ alkenyl | —(CH$_2$)$_2$O—C$_{2-24}$ alkenyl |
| G5 | O | O | —C$_{2-24}$ alkynyl | —(CH$_2$)$_2$O—C$_{2-24}$ alkenyl |
| G5 | O | O | —(CH$_2$)$_2$O—C$_{2-24}$ alkenyl | —(CH$_2$)$_2$O—C$_{2-24}$ alkenyl |
| G5 | O | O | cycloalkyl | —(CH$_2$)$_2$O—C$_{2-24}$ alkenyl |
| G5 | O | O | cycloalkyl(C$_{1-4}$ alkyl)- | —(CH$_2$)$_2$O—C$_{2-24}$ alkenyl |
| G5 | O | O | cycloalkenyl | —(CH$_2$)$_2$O—C$_{2-24}$ alkenyl |
| G5 | O | O | cycloalkenyl(C$_{1-4}$ alkyl) | —(CH$_2$)$_2$O—C$_{2-24}$ alkenyl |
| G5 | O | O | Aryl | —(CH$_2$)$_2$O—C$_{2-24}$ alkenyl |
| G5 | O | O | aryl(C$_{1-4}$ alkyl) | —(CH$_2$)$_2$O—C$_{2-24}$ alkenyl |
| G5 | O | O | Heteroaryl | —(CH$_2$)$_2$O—C$_{2-24}$ alkenyl |
| G5 | | O | heteroaryl(C$_{1-4}$ alkyl) | —(CH$_2$)$_2$O—C$_{2-24}$ alkenyl |

TABLE 1-continued

| B¹ | Z¹ | Z² | R¹ | R¹ |
|---|---|---|---|---|
| G5 | O | O | –CH₂C(=O)R⁵ | –CH₂C(=O)R⁵ |
| G5 | O | O | –(CH₂)₂–S–C(=O)R⁸ | –(CH₂)₂–S–C(=O)R⁸ |
| G5 | O | O | –(CH₂)₂–S–S–CH₂CH₂OH | –(CH₂)₂–S–S–CH₂CH₂OH |
| G5 | O | O | –CH₂-(5-nitrofuran-2-yl) | –CH₂-(5-nitrofuran-2-yl) |
| G5 | NCH₃ | O | –(CH₂)₃CH₂Cl | –CH₂-(5-nitrofuran-2-yl) |
| G5 | ++ | O | –(CH₂)₃CH₂Cl | –CH₂-(5-nitrofuran-2-yl) |
| G5 | O | O | –(CH₂)₃– (bridging) | |
| G5 | O | O | –CH₂-(o-phenylene)-CH₂– (bridging) | |
| G6 | O | O | –C$_{2\text{-}24}$ alkenyl | –C$_{12\text{-}24}$ alkenyl |
| G6 | O | O | –C$_{2\text{-}24}$ alkynyl | –C$_{12\text{-}24}$ alkenyl |
| G6 | O | O | –(CH₂)₂O–C$_{2\text{-}24}$ alkenyl | –C$_{12\text{-}24}$ alkenyl |
| G6 | O | O | cycloalkyl | –C$_{12\text{-}24}$ alkenyl |
| G6 | O | O | cycloalkyl(C$_{1\text{-}4}$ alkyl)- | –C$_{12\text{-}24}$ alkenyl |
| G6 | O | O | cycloalkenyl | –C$_{12\text{-}24}$ alkenyl |
| G6 | O | O | cycloalkenyl(C$_{1\text{-}4}$ alkyl) | –C$_{12\text{-}24}$ alkenyl |
| G6 | O | O | Aryl | –C$_{12\text{-}24}$ alkenyl |
| G6 | O | O | aryl(C$_{1\text{-}4}$ alkyl) | –C$_{12\text{-}24}$ alkenyl |
| G6 | O | O | Heteroaryl | –C$_{12\text{-}24}$ alkenyl |
| G6 | O | O | heteroaryl(C$_{1\text{-}4}$ alkyl) | –C$_{12\text{-}24}$ alkenyl |
| G6 | O | O | –C$_{2\text{-}24}$ alkenyl | –(CH₂)₂O–C$_{2\text{-}24}$ alkenyl |
| G6 | O | O | –C$_{2\text{-}24}$ alkynyl | –(CH₂)2O–C$_{2\text{-}24}$ alkenyl |
| G6 | O | O | –(CH₂)₂O–C$_{2\text{-}24}$ alkenyl | –(CH₂)₂O–C$_{2\text{-}24}$ alkenyl |
| G6 | O | O | cycloalkyl | –(CH₂)₂O–C$_{2\text{-}24}$ alkenyl |
| G6 | O | O | cycloalkyl(C$_{1\text{-}4}$ alkyl)- | –(CH₂)₂O–C$_{2\text{-}24}$ alkenyl |
| G6 | O | O | cycloalkenyl | –(CH₂)₂O–C$_{2\text{-}24}$ alkenyl |
| G6 | O | O | cycloalkenyl(C$_{1\text{-}4}$ alkyl) | –(CH₂)₂O–C$_{2\text{-}24}$ alkenyl |
| G6 | O | O | Aryl | –(CH₂)₂O–C$_{2\text{-}24}$ alkenyl |
| G6 | O | O | aryl(C$_{1\text{-}4}$ alkyl) | –(CH₂)₂O–C$_{2\text{-}24}$ alkenyl |
| G6 | O | O | Heteroaryl | –(CH₂)₂O–C$_{2\text{-}24}$ alkenyl |
| G6 | | O | heteroaryl(C$_{1\text{-}4}$ alkyl) | –(CH₂)₂O–C$_{2\text{-}24}$ alkenyl |
| G6 | O | O | –CH₂C(=O)R⁵ | –CH₂C(=O)R⁵ |

TABLE 1-continued

| B¹ | Z¹ | Z² | R¹ | R¹ |
|---|---|---|---|---|
| G6 | O | O | ~CH₂CH₂CH₂—S—C(=O)—R⁸ | ~CH₂CH₂CH₂—S—C(=O)—R⁸ |
| G6 | O | O | ~CH₂CH₂CH₂—S—S—CH₂CH₂OH | ~CH₂CH₂CH₂—S—S—CH₂CH₂OH |
| G6 | O | O | ~CH₂-(5-nitrofuran-2-yl) | ~CH₂-(5-nitrofuran-2-yl) |
| G6 | NCH₃ | O | —(CH₂)₃CH₂Cl | ~CH₂-(5-nitrofuran-2-yl) |
| G6 | ++ | O | —(CH₂)₃CH₂Cl | ~CH₂-(5-nitrofuran-2-yl) |
| G6 | O | O | *—CH₂CH₂CH₂CH₂—* (butylene linker) | |
| G6 | O | O | *—CH₂-(o-phenylene)—* | |
| G7 | O | O | —C₂₋₂₄ alkenyl | —C₁₂₋₂₄ alkenyl |
| G7 | O | O | —C₂₋₂₄ alkynyl | —C₁₂₋₂₄ alkenyl |
| G7 | O | O | —(CH₂)₂O—C₂₋₂₄ alkenyl | —C₁₂₋₂₄ alkenyl |
| G7 | O | O | cycloalkyl | —C₁₂₋₂₄ alkenyl |
| G7 | O | O | cycloalkyl(C₁₋₄ alkyl)- | —C₁₂₋₂₄ alkenyl |
| G7 | O | O | cycloalkenyl | —C₁₂₋₂₄ alkenyl |
| G7 | O | O | cycloalkenyl(C₁₋₄ alkyl) | —C₁₂₋₂₄ alkenyl |
| G7 | O | O | Aryl | —C₁₂₋₂₄ alkenyl |
| G7 | O | O | aryl(C₁₋₄ alkyl) | —C₁₂₋₂₄ alkenyl |
| G7 | O | O | Heteroaryl | —C₁₂₋₂₄ alkenyl |
| G7 | O | O | heteroaryl(C₁₋₄ alkyl) | —C₁₂₋₂₄ alkenyl |
| G7 | O | O | —C₂₋₂₄ alkenyl | —(CH₂)₂O—C₂₋₂₄ alkenyl |
| G7 | O | O | —C₂₋₂₄ alkynyl | —(CH₂)₂O—C₂₋₂₄ alkenyl |
| G7 | O | O | —(CH₂)₂O—C₂₋₂₄ alkenyl | —(CH₂)₂O—C₂₋₂₄ alkenyl |
| G7 | O | O | cycloalkyl | —(CH₂)₂O—C₂₋₂₄ alkenyl |
| G7 | O | O | cycloalkyl(C₁₋₄ alkyl)- | —(CH₂)₂O—C₂₋₂₄ alkenyl |
| G7 | O | O | cylcoalkenyl | —(CH₂)₂O—C₂₋₂₄ alkenyl |
| G7 | O | O | cycloalkenyl(C₁₋₄ alkyl) | —(CH₂)₂O—C₂₋₂₄ alkenyl |
| G7 | O | O | Aryl | —(CH₂)₂O—C₂₋₂₄ alkenyl |
| G7 | O | O | aryl(C₁₋₄ alkyl) | —(CH₂)₂O—C₂₋₂₄ alkenyl |
| G7 | O | O | Heteroaryl | —(CH₂)₂O—C₂₋₂₄ alkenyl |
| G7 | O | O | heteroaryl(C₁₋₄ alkyl) | —(CH₂)₂O—C₂₋₂₄ alkenyl |
| G7 | O | O | ~CH₂—C(=O)—R⁵ | ~CH₂—C(=O)—R⁵ |
| G7 | O | O | ~CH₂CH₂CH₂—S—C(=O)—R⁸ | ~CH₂CH₂CH₂—S—C(=O)—R⁸ |

TABLE 1-continued

| $B^1$ | $Z^1$ | $Z^2$ | $R^1$ | $R^1$ |
|---|---|---|---|---|
| G7 | O | O | ~~~CH₂CH₂-S-S-CH₂CH₂OH | ~~~CH₂CH₂-S-S-CH₂CH₂OH |
| G7 | O | O | ~~~CH₂-(furan)-NO₂ | ~~~CH₂-(furan)-NO₂ |
| G7 | NCH₃ | O | —(CH₂)₃CH₂Cl | ~~~CH₂-(furan)-NO₂ |
| G7 | ++ | O | —(CH₂)₃CH₂Cl | ~~~CH₂-(furan)-NO₂ |
| G7 | O | O | *—CH₂CH₂CH₂CH₂—* | |
| G7 | O | O | *—CH₂-(o-C₆H₄)-CH₂—* | |

++ = N(CH₂)—CH(OH)—CH₂OH

In an alternate embodiment, in Table 1, when the base is G1 or G2, $R^3$ can be selected from optionally substituted alkyl such as $CH_3$, $CH_2OH$, $CH_2F$, $CHF_2$, $CF_3$, or optionally substituted heteroalkyl such as $OCH_3$. In Table 1, $C_{2-24}$ alkenyl, —(CIH₂)₂O—$C_{2-24}$ alkenyl, aryl (including phenyl), aryl($C_{1-4}$ alkyl) (including benzyl),

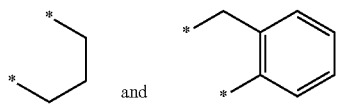 [SMILES: *CCC* ; *Cc1ccccc1*]

and can be each optionally substituted. $R^{13}$ is $C_{1-6}$ alkyl or cycloalkyl($C_{0-4}$ alkyl).

In some embodiments, at least one of $R^1$ and $R^2$ can be an optionally substituted $C_{2-24}$ alkenyl. In still other embodiments, $R^1$ and $R^2$ both can be an optionally substituted $C_{2-24}$ alkenyl. When one or both of $R^1$ and $R^2$ is an optionally substituted $C_{2-24}$ alkenyl, the optionally substituted $C_{2-24}$ alkenyl can be the aliphatic chain from a fatty acid. Fatty acid aliphatic chains differ by length. Types of fatty acids include short-chain fatty acids (fewer than six carbons), medium-chain fatty acids (six to twelve carbons), long-chain fatty acids (thirteen to twenty-one carbons), and very long-chain fatty acids (more than twenty-two carbons). Examples of aliphatic chains include, but are not limited to, the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl. In some embodiments of this paragraph, at least one of $Z^1$ and $Z^2$ can be O. In some embodiments of this paragraph, both $Z^1$ and $Z^2$ can be O.

In some embodiments, at least one of $R^1$ and $R^2$ can be —(CHR⁴)$_b$—O—$C_{2-24}$ alkenyl. In other embodiments, $R^1$ and $R^2$ both can be —(CHR⁴)$_b$—O—$C_{2-24}$ alkenyl. In some embodiments, each $R^4$ can be hydrogen. In some embodiments, at least one $R^4$ can be —(CH₂)$_c$—S—$C_{1-24}$ alkyl. In some embodiments, at least one $R^4$ can be —O—(CH₂)$_d$—$R^{4.4}$. In some embodiments, b can be 1. In other embodiments, b can be 2. In still other embodiments, b can be 3. In yet still other embodiments, b can be 4. In some embodiments of this paragraph, at least one of $Z^1$ and $Z^2$ can be O. In some embodiments of this paragraph, both $Z^1$ and $Z^2$ can be O.

When an $R^4$ moiety is present, in some embodiments, $R^{4.4}$ can be H (hydrogen). In other embodiments, $R^{4.4}$ can be an optionally substituted $C_{1-24}$ alkyl. In still other embodiments, $R^{4.4}$ can be an optionally substituted aryl. In embodiments, at least one $R^4$ can be —(CH₂)$_c$—S—$C_{1-24}$ alkyl, and c can be 0. In other embodiments, at least one $R^4$ can be —(CH₂)$_c$—S—$C_{1-24}$ alkyl, and c can be 1. In still other embodiments, at least one $R^4$ can be —(CH₂)$_c$—S—$C_{1-24}$ alkyl, and c can be 2. In yet still other embodiments, at least one $R^4$ can be —(CH₂)$_c$—S—$C_{1-24}$ alkyl, and c can be 3. In embodiments, at least one $R^4$ can be —O—(CH₂)$_d$—$R^{4.4}$, and d can be 0. In other embodiments, at least one $R^4$ can be —O—(CH₂)$_d$—$R^{4.4}$, and d can be 1. In still other embodiments, at least one $R^4$ can be —O—(CH₂)$_d$—$R^{4.4}$, and d can be 2. In yet still other embodiments, at least one $R^4$ can be —O—(CH$_2$)$_d$—R$^{4.4}$, and d can be 3. When more than one $R^4$ is present, the $R^4$ moieties can be the same, or at least one $R^4$ can be different.

In embodiments, at least one of $R^1$ and $R^2$ can be an optionally substituted aryl($C_{1-4}$ alkyl). In other embodiments, $R^1$ and $R^2$ both can be an optionally substituted aryl($C_{1-4}$ alkyl). A suitable optionally substituted aryl($C_{1-4}$ alkyl) is an optionally substituted benzyl. When the aryl and/or aryl($C_{1-4}$ alkyl) is substituted, the aryl ring can be substituted with 1, 2, 3 or more than 3 substituents. When more than two substituents are present, the substituents can be the same or different. In embodiments, the aryl ring can be a para-, ortho- or meta-substituted phenyl. In some embodiments of this paragraph, at least one of $Z^1$ and $Z^2$ can be O. In some embodiments of this paragraph, both $Z^1$ and $Z^2$ can be O.

In embodiments, at least one of $R^1$ and $R^2$ can be

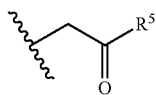

or one of $R^1$ and $R^2$ can be

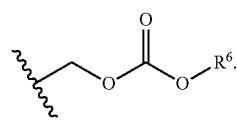

In other embodiments, $R^1$ and $R^2$ both can be

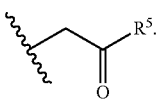

In embodiments, $R^5$ can be an optionally substituted $C_{1-8}$ alkyl. In embodiments, $R^5$ can be an unsubstituted $C_{1-6}$ alkyl. In other embodiments, $R^5$ can be an optionally substituted $C_{2-8}$ alkenyl, such as an optionally substituted allyl. In still other embodiments, $R^5$ can be an optionally substituted cycloalkyl, for example, an optionally substituted $C_{3-6}$ cycloalkyl or an optionally substituted $C_{5-6}$ cycloalkyl. In yet still other embodiments, $R^5$ can be an optionally substituted aryl, such as an optionally substituted phenyl. In embodiments, $R^6$ can be an optionally substituted $C_{1-8}$ alkyl. In embodiments, $R^6$ can be an unsubstituted $C_{1-6}$ alkyl. In other embodiments, $R^6$ can be an optionally substituted $C_{2-8}$ alkenyl. In still other embodiments, $R^6$ can be an optionally substituted cycloalkyl. In yet still other embodiments, $R^6$ can be an optionally substituted aryl, such as an optionally substituted phenyl. Examples of suitable $R^6$ groups include, but are not limited to, methyl, ethyl, n-propyl, isopropyl, n-butyl, iso-butyl, tert-butyl, pentyl (branched or straight chained), hexyl (branched or straight chained), an optionally substituted allyl, an optionally substituted $C_{3-6}$ cycloalkyl, an optionally substituted $C_{5-6}$ cycloalkyl and an optionally substituted phenyl. In some embodiments of this paragraph, at least one of $Z^1$ and $Z^2$ can be O. In some embodiments of this paragraph, both $Z^1$ and $Z^2$ can be O. In embodiments, one of $R^1$ and $R^2$ can be isopropyloxycarbonyloxymethyl (POC).

In embodiments, at least one of $R^1$ and $R^2$ can be

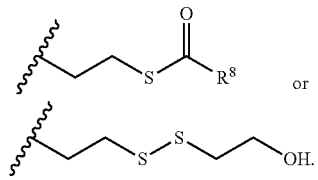

In other embodiments, $R^1$ and $R^2$ both can be

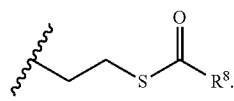

In still other embodiments, $R^1$ and $R^2$ both can be

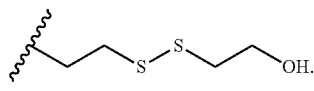 [SMILES: *CCSSCCO]

In embodiments, $R^8$ can be an optionally substituted $C_{1-8}$ alkyl. In embodiments, $R^8$ can be an unsubstituted $C_{1-6}$ alkyl. In other embodiments, $R^8$ can be an optionally substituted $C_{2-8}$ alkenyl, such as an optionally substituted allyl. In still other embodiments, $R^8$ can be an optionally substituted cycloalkyl, for example, an optionally substituted $C_{3-6}$ cycloalkyl or an optionally substituted $C_{5-6}$ cycloalkyl. In yet still other embodiments, $R^8$ can be an optionally substituted aryl, such as an optionally substituted phenyl. In some embodiments of this paragraph, at least one of $Z^1$ and $Z^2$ can be O. In some embodiments of this paragraph, both $Z^1$ and $Z^2$ can be O. In embodiments, $R^1$ and $R^2$ both can be an S-acylthioethyl (SATE) group and form a SATE ester prodrug. In other embodiments, $R^1$ and $R^2$ both can be a S-[(2-hydroxyethyl)sulfidyl]-2-thioethyl (DTE) group and form a DTE ester prodrug. In still other embodiments, one of $R^1$ and $R^2$ can be a S-acylthioethyl (SATE) group, and the other of $R^1$ and $R^2$ can be an optionally substituted phenyl group and form a phenyl(SATE) prodrug. In yet still other embodiments, one of $R^1$ and $R^2$ can be a S-acylthioethyl (SATE) group, and the other of $R^1$ and $R^2$ can be an N-linked alpha-amino acid ester and form a (SATE)-phosphonoamidate diester prodrug.

The term "N-linked alpha-amino acid ester" refers to an amino acid that is attached to the indicated moiety via a main-chain amino or mono-substituted amino group and wherein the main-chain carboxylic acid group has been converted to an ester group. Examples of alpha-amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. When the amino acid is attached in an —N-linked amino acid, one of the hydrogens that is part of the main-chain amino or mono-substituted amino group is not present and the amino acid is attached via the nitrogen. In embodiments, the ester group has a formula selected from alkyl-O—C(=O)—, cycloalkyl-O—C(=O)—, aryl-O—C(=O)— and aryl(alkyl)-O—C(=O)—. N-linked alpha-amino acid esters can be substituted or unsubstituted. When $R^1$ and/or $R^2$ is an N-linked alpha-amino acid ester, the main-chain nitrogen of the main-chain amino or mono-substituted amino group is the nitrogen of $Z^1$ and/or $Z^2$, respectively.

In embodiments, at least one of $R^1$ and $R^2$ can be

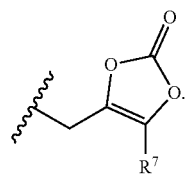

In other embodiments, $R^1$ and $R^2$ both can be

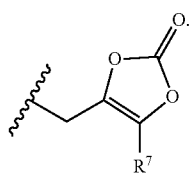

In embodiments, $R^7$ can be hydrogen. In other embodiments, $R^7$ can be an optionally substituted $C_{1-8}$ alkyl. In embodiments, $R^7$ can be a $C_{1-4}$ alkyl, such as methyl, ethyl, n-propyl, iso-propyl, n-butyl, iso-butyl and t-butyl. In still other embodiments, $R^7$ can be an optionally substituted cycloalkyl, for example, an optionally substituted $C_{3-6}$ cycloalkyl or an optionally substituted $C_{5-6}$ cycloalkyl. In yet still other embodiments, $R^7$ can be an optionally substituted aryl, such as an optionally substituted phenyl or an optionally substituted naphthyl. In some embodiments of this paragraph, at least one of $Z^1$ and $Z^2$ can be O. In some embodiments of this paragraph, both $Z^1$ and $Z^2$ can be O. In embodiments, $R^1$ and $R^2$ both can be a dioxolenone group and form a dioxolenone prodrug.

In embodiments, $R^1$ and $R^2$ can be taken together to form an optionally substituted

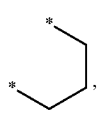

wherein $Z^1$, $Z^2$, $R^1$ and $R^2$, the phosphorus and the moiety form a six-membered ring system, and the "*" indicate the points of attachment to $Z^1$ and $Z^2$, respectively. An example of $R^1$ and $R^2$ taken together to form an optionally substituted

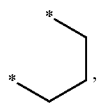

wherein $Z^1$, $Z^2$, $R^1$ and $R^2$, the phosphorus and the moiety form a six-membered ring system is the following:

(Ph is an optionally substituted phenyl).
When substituted, the ring of

can be substituted 1, 2, 3 or 3 or more times. When substituted with multiple substituents, the substituents can be the same or different. In embodiments, the

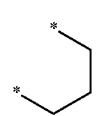

ring can be substituted with an optionally substituted aryl, an optionally substituted heteroaryl or an optionally substituted heterocyclyl. In embodiments, $R^1$ and $R^2$ can be taken together to form an optionally substituted

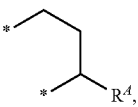

such as

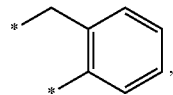

wherein $R^A$ can be an optionally substituted phenyl, an optionally substituted mono-cyclic heteroaryl (such as pyridinyl) or an optionally substituted mono-cyclic heterocyclyl. In embodiments, $R^{6A}$ and $R^{7A}$ can form a cyclic 1-aryl-1,3-propanyl ester (HEPDIRECT™) prodrug moiety.

In embodiments, $R^1$ and $R^2$ can be taken together to form an optionally substituted

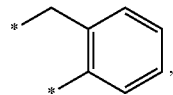

wherein $Z^1$, $Z^2$, $R^1$ and $R^2$, the phosphorus and the moiety form a ten-membered ring system, and the "*" indicate the points of attachment to $Z^1$ and $Z^2$, respectively. Example of an optionally substituted

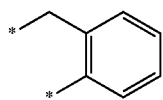

include

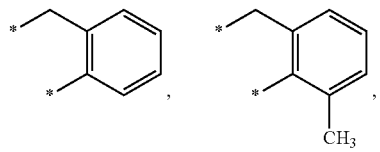

In embodiments, $R^1$ and $R^2$ can form a cyclosaligenyl (cycloSal) prodrug. An example of $R^1$ and $R^2$ taken together to form an optionally substituted

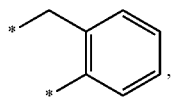

wherein $Z^1$, $Z^2$, $R^1$ and $R^2$, the phosphorus and the moiety form a ten-membered ring system is the following:

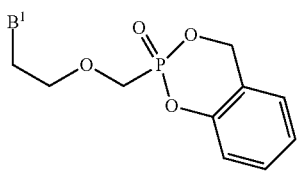

In embodiments, one of $R^1$ or $R^2$ can be

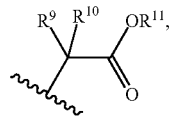

wherein $Z^1$ can be $NR^Z$, such as NH. In embodiments, $R^9$ can be hydrogen. In other embodiments, $R^9$ can be an optionally substituted $C_{1-6}$ alkyl. In embodiments, $R^{10}$ can be hydrogen. In other embodiments, $R^{10}$ can be an unsubstituted $C_{1-6}$ alkyl, —$CH_2SH$, —$CH_2(C=O)NH_2$, —$CH_2CH_2(C=O)NH_2$, —$CH_2CH_2S$ $CH_3$, $CH_2$-an optionally substituted phenyl, —$CH_2OH$, —$CH(OH)CH_3$,

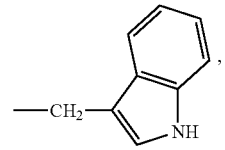

—$CH_2(C=O)OH$, —$CH_2CH_2(C=O)OH$, —$(CH_2)_3NH$ $(C=NH)NH_2$,

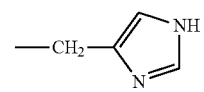

or —$(CH_2)_4NH_2$. In embodiments, $R^{11}$ can be hydrogen. In embodiments, $R^{11}$ can be an optionally substituted $C_{1-8}$ alkyl. In still other embodiments, $R^1$ can be an optionally substituted cycloalkyl, such as an optionally substituted $C_{3-6}$ cycloalkyl. In yet still other embodiments, $R^{11}$ can be an optionally substituted aryl. For example, $R^{11}$ can be a substituted or unsubstituted phenyl. In embodiments, $R^{11}$ can be an optionally substituted aryl($C_{1-6}$ alkyl) (such as an optionally substituted benzyl).

When $Z^1$ and $R^1$ or $Z^2$ and $R^2$ form

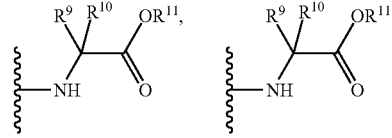

can be N-linked alpha-amino acid ester. N-linked alpha-amino acid esters are described herein. In embodiments,

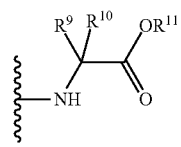

can be

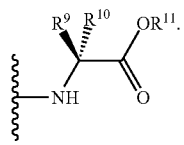

In other embodiments,

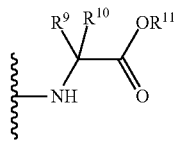

can be

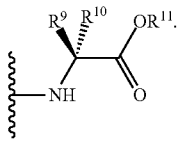

In embodiments, $R^1$ can be

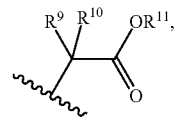

wherein $Z^1$ can be NH; and $R^2$ can be an optionally substituted aryl($C_{1-4}$ alkyl) (for example, an optionally substituted benzyl), and form an optionally substituted benzyl phosphonoamidate prodrug.

When $Z^1$ or $Z^2$ is $NR^Z$, $R^Z$ can be H (hydrogen) or an optionally substituted $C_{1-4}$ alkyl. In embodiments, $Z^1$ or $Z^2$ can be NH. In other embodiments, $Z^1$ or $Z^2$ can be N-an optionally substituted $C_{1-4}$ alkyl. In embodiments, $Z^1$ or $Z^2$ can be N-an unsubstituted $C_{1-4}$ alkyl. For example, $Z^1$ or $Z^2$ can be N-methyl, N-ethyl, N-(n-propyl), N-(iso-propyl), N-(n-butyl), N-(iso-butyl) or N-(t-butyl). In embodiments, the N-an optionally substituted $C_{1-4}$ alkyl can be —N(CH$_2$)—CH(OH)—CH$_2$OH.

In embodiments, at least one of $R^1$ and $R^2$ can be

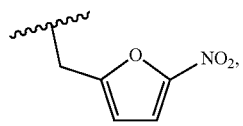 [SMILES: *Cc1ccc([N+](=O)[O-])o1]

In other embodiments, $R^1$ and $R^2$ both can be

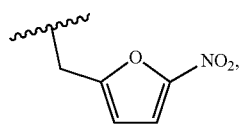 [SMILES: *Cc1ccc([N+](=O)[O-])o1]

In embodiments, one of $R^1$ and $R^2$ can be

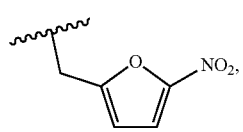 [SMILES: *Cc1ccc([N+](=O)[O-])o1]

and the other of $R^1$ and $R^2$ can be an optionally substituted $C_{2-24}$ alkenyl. In some embodiments of this paragraph, at least one of $Z^1$ and $Z^2$ can be O. In some embodiments of this paragraph, both $Z^1$ and $Z^2$ can be O. In some embodiments of this paragraph, one of $Z^1$ and $Z^2$ can be O and the other of $Z^1$ and $Z^2$ can be $NR^Z$. Examples of prodrugs that include

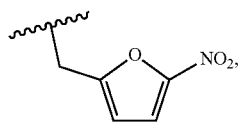 [SMILES: *Cc1ccc([N+](=O)[O-])o1]

include the following:

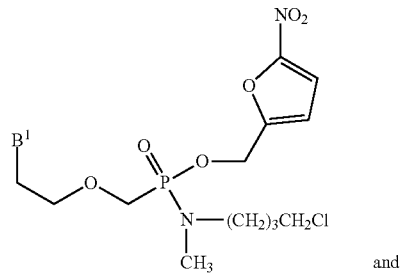

and

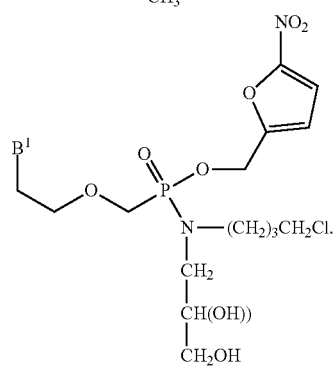

In embodiments, a compound of Formula (I) can be a nitrofuranylmethyl phosphonoamidate prodrug, wherein $R^1$ can be

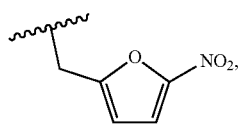 [SMILES: *Cc1ccc([N+](=O)[O-])o1]

$R^2$ can be (CH$_2$)$_3$CH$_2$Cl, $Z^1$ can be O, and $Z^2$ can be NCH$_3$. In embodiments, a compound of Formula (I) can be a nitrofuranylmethyl N-dihydroxypropyl phosphonoamidate prodrug, wherein $R^1$ can be

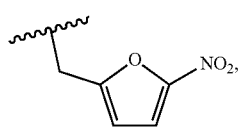

$R^2$ can be —(CH$_2$)$_3$CH$_2$Cl, $Z^1$ can be O, and $Z^2$ can be —N(CH$_2$)—CH(OH)—CH$_2$OH.

In embodiments, $R^1$ and $R^2$ can be the same. In embodiments, $R^1$ and $R^2$ can be different.

In a second embodiment disclosed herein are compound of Formula (I), or a pharmaceutically acceptable salt thereof:

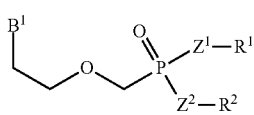

(I)

wherein: $B^1$ is as defined above; $Z^1$ and $Z^2$ can be independently O (oxygen) or $NR^Z$, wherein $R^Z$ can be H (hydrogen) or an optionally substituted $C_{1-4}$ alkyl; $R^1$ can be selected from an optionally substituted $—C_{1-24}$ alkyl, an optionally substituted $—C_{2-24}$ alkenyl, an optionally substituted $—(CHR^4)_a—O—C_{1-24}$ alkyl, an optionally substituted $—(CHR^4)_b—O—C_{2-24}$ alkenyl, an optionally substituted aryl, an optionally substituted aryl($C_{1-4}$ alkyl), an optionally substituted heteroaryl, an optionally substituted heterocyclyl,

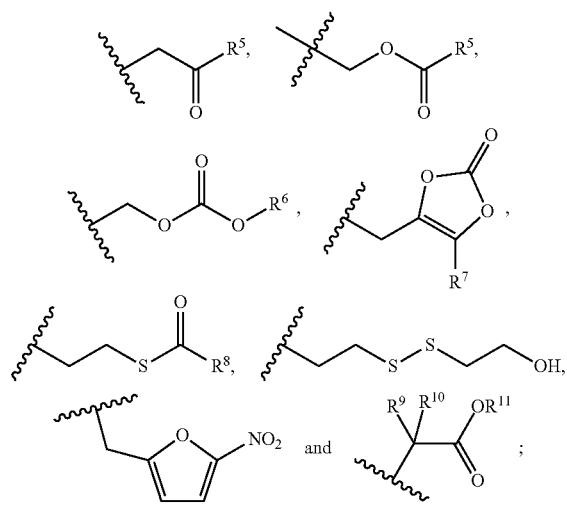

$R^2$ can be selected from an optionally substituted $—C_{1-24}$ alkyl, an optionally substituted $—C_{2-24}$ alkenyl, an optionally substituted $—(CHR^4)_a—O—C_{1-24}$ alkyl, an optionally substituted $—(CHR^4)_b—O—C_{2-24}$ alkenyl, an optionally substituted aryl, an optionally substituted aryl($C_{1-4}$ alkyl),

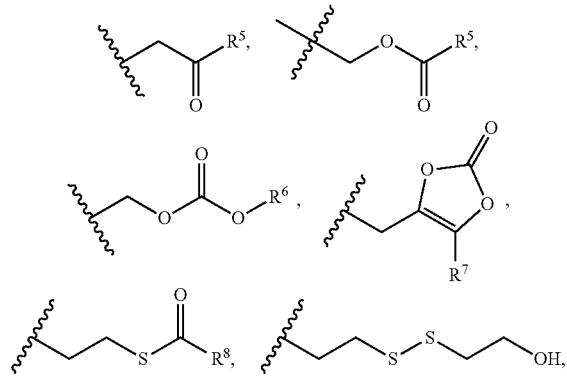

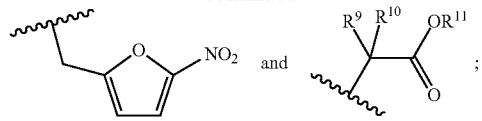

or $Z^1$ and $Z^2$ can be O; and $R^1$ and $R^2$ can be taken together to form a moiety selected from an optionally substituted

and an optionally substituted

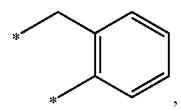

wherein $Z^1$, $Z^2$, $R^1$ and $R^2$, the phosphorus and the moiety form a six-membered to ten-membered ring system; each $R^4$ can be independently H (hydrogen), $—(CH_2)_c—S—C_{1-24}$ alkyl or $—O—(CH_2)_d—R^{4A}$; each $R^{4A}$ can be H (hydrogen), an optionally substituted $C_{1-24}$ alkyl or an optionally substituted aryl; each $R^5$, each $R^6$ and each $R^8$ can be independently an optionally substituted $C_{1-8}$ alkyl, an optionally substituted $C_{2-8}$ alkenyl, an optionally substituted cycloalkyl or an optionally substituted aryl; each $R^9$ can be independently H (hydrogen) or an optionally substituted $C_{1-6}$ alkyl.

In embodiments, $R^1$ can be absent or H; and $R^2$ can be selected from an optionally substituted $—C_{1-24}$ alkyl, an optionally substituted $—C_{2-24}$ alkenyl, an optionally substituted $—(CHR^4)_a—O—C_{1-24}$ alkyl, an optionally substituted $—(CHR^4)_b—O—C_{2-24}$ alkenyl, an optionally substituted aryl, an optionally substituted aryl($C_{1-4}$ alkyl),

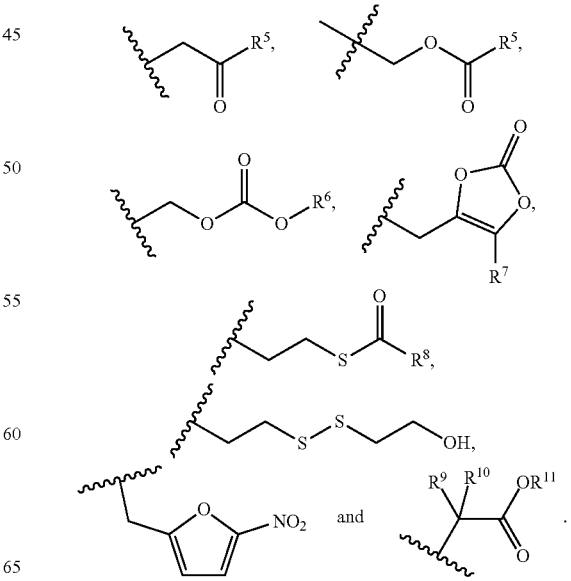

In embodiments, $R^1$ and $R^2$ can be independently selected from an optionally substituted —$C_{1-24}$ alkyl, an optionally substituted —$C_{2-24}$ alkenyl, an optionally substituted —$(CHR^4)_b$—O—$C_{1-24}$ alkyl, an optionally substituted —$(CHR^4)_a$—O—$C_{2-24}$ alkenyl, an optionally substituted aryl, an optionally substituted aryl($C_{1-4}$ alkyl),

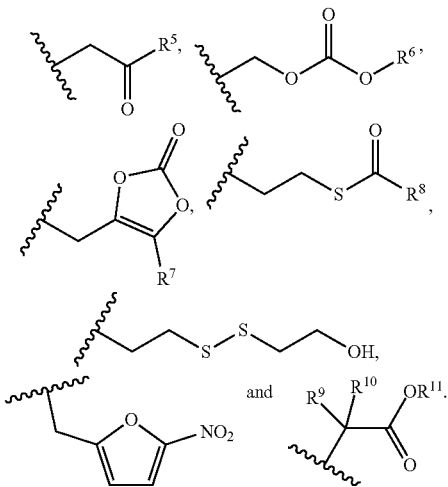

In embodiments, at least one of $R^1$ and $R^2$ can be an optionally substituted $C_{1-24}$ alkyl or an optionally substituted $C_{2-24}$ alkenyl. In other embodiments, $R^1$ and $R^2$ both can be an optionally substituted $C_{1-24}$ alkyl. In still other embodiments, $R^1$ and $R^2$ both can be an optionally substituted $C_{2-24}$ alkenyl. When one or both of $R^1$ and $R^2$ is an optionally substituted $C_{1-24}$ alkyl or an optionally substituted $C_{2-24}$ alkenyl, the optionally substituted $C_{1-24}$ alkyl and/or the optionally substituted $C_{2-24}$ alkenyl can be the aliphatic chain from a fatty acid. Fatty acid aliphatic chains differ by length. Types of fatty acids include short-chain fatty acids (fewer than six carbons), medium-chain fatty acids (six to twelve carbons), long-chain fatty acids (thirteen to twenty-one carbons), and very long-chain fatty acids (more than twenty-two carbons). Examples of aliphatic chains include, but are not limited to, the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl. In some embodiments of this paragraph, at least one of $Z^1$ and $Z^2$ can be O. In some embodiments of this paragraph, both $Z^1$ and $Z^2$ can be O.

In embodiments, at least one of $R^1$ and $R^2$ can be —$(CHR^4)_a$—O—$C_{1-24}$ alkyl. In other embodiments, $R^1$ and $R^2$ both can be —$(CHR^4)_a$—O—$C_{1-24}$ alkyl. In some embodiments, each $R^4$ can be hydrogen. In some embodiments, at least one $R^4$ can be —$(CH_2)_c$—S—$C_{1-24}$ alkyl. In some embodiments, at least one $R^4$ can be —O—$(CH_2)_d$—$R^{4A}$. In some embodiments, a can be 1. In other embodiments, a can be 2. In still other embodiments, a can be 3. In yet still other embodiments, a can be 4. In some embodiments of this paragraph, at least one of $Z^1$ and $Z^2$ can be O. In some embodiments of this paragraph, both $Z^1$ and $Z^2$ can be O.

In some embodiments, at least one of $R^1$ and $R^2$ can be —$(CHR^4)_b$—O—$C_{2-24}$ alkenyl. In other embodiments, $R^1$ and $R^2$ both can be —$(CHR^4)_b$—O—$C_{2-24}$ alkenyl. In some embodiments, each $R^4$ can be hydrogen. In some embodiments, at least one $R^4$ can be —$(CH_2)_c$—S—$C_{1-24}$ alkyl. In some embodiments, at least one $R^4$ can be —O—$(CH_2)_d$—$R^{4A}$. In some embodiments, b can be 1. In other embodiments, b can be 2. In still other embodiments, b can be 3. In yet still other embodiments, b can be 4. In some embodiments of this paragraph, at least one of $Z^1$ and $Z^2$ can be O. In some embodiments of this paragraph, both $Z^1$ and $Z^2$ can be O.

In some embodiments, at least one of $R^1$ and $R^2$ can be an optionally substituted aryl. In other embodiments, $R^1$ and $R^2$ both can be an optionally substituted aryl. For example, one or both $R^1$ and $R^2$ can be an optionally substituted phenyl. In some embodiments, at least one of $R^1$ and $R^2$ can be an optionally substituted aryl($C_{1-4}$ alkyl). In other embodiments, $R^1$ and $R^2$ both can be an optionally substituted aryl($C_{1-4}$ alkyl). A suitable optionally substituted aryl($C_{1-4}$ alkyl) is an optionally substituted benzyl. When the aryl and/or aryl($C_{1-4}$ alkyl) is substituted, the aryl ring can be substituted with 1, 2, 3 or more than 3 substituents. When more than two substituents are present, the substituents can be the same or different. In some embodiments, the aryl ring can be a para-, ortho- or meta-substituted phenyl. In some embodiments of this paragraph, at least one of $Z^1$ and $Z^2$ can be O. In some embodiments of this paragraph, both $Z^1$ and $Z^2$ can be O.

In embodiments, at least one of $R^1$ and $R^2$ can

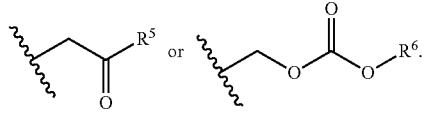

In embodiments, $R^1$ and $R^2$ both can be

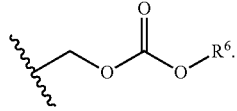

In embodiments, $R^1$ and $R^2$ both can be a isopropyloxycarbonyloxymethyl (POC) group, and form a bis(isopropyloxycarbonyloxymethyl) (bis(POC)) prodrug. In other embodiments, one or both of $R^1$ and $R^2$ can be pivaloyloxymethyl (POM). In some embodiments, $R^1$ and $R^2$ both can be a pivaloyloxymethyl (POM) group, and form a bis(pivaloyloxymethyl) (bis(POM)) prodrug.

In embodiments, $R^1$ and $R^2$ both can be a S-[(2-hydroxyethyl)sulfidyl]-2-thioethyl (DTE) group and form a DTE ester prodrug. In still other embodiments, one of $R^1$ and $R^2$ can be a S-acylthioethyl (SATE) group, and the other of $R^1$ and $R^2$ can be an optionally substituted phenyl group and form a phenyl(SATE) prodrug. In yet still other embodiments, one of $R^1$ and $R^2$ can be a S-acylthioethyl (SATE) group, and the other of $R^1$ and $R^2$ can be an N-linked alpha-amino acid ester and form a (SATE)-phosphonamidate diester prodrug.

In embodiments, at least $R^1$ can be

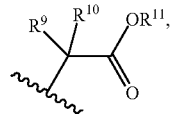

wherein $Z^1$ can be $NR^Z$, such as NH.

In other embodiments, $R^1$ and $R^2$ both can be

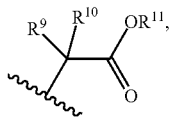

wherein $Z^1$ and $Z^2$ both can be $NR^Z$, such as NH. In some embodiments, $R^9$ can be hydrogen. In other embodiments, $R^9$ can be an optionally substituted $C_{1-6}$ alkyl.

In embodiments, a compound of Formula (I) can be a phosphorodiamidate prodrug, wherein $R^1$ and $R^2$ both can be

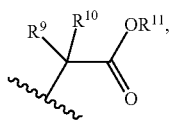

wherein $Z^1$ and $Z^2$ both can be $NR^Z$, such as NH.

In embodiments, a compound of Formula (I) can be a nitrofuranylmethyl phosphonoamidate prodrug, wherein $R^1$ can be

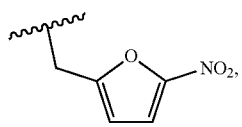 [SMILES: *Cc1ccc([N+](=O)[O-])o1]

$R^2$ can be —$(CH_2)_3CH_2Cl$, $Z^1$ can be O, and $Z^2$ can be $NCH_3$.

In embodiments, $R^1$ and $R^2$ can be the same. In some embodiments, $R^1$ and $R^2$ can be different.

As described herein, $B^1$ can be a naturally occurring purine, naturally occurring pyrimidine, non-naturally occurring purine or a non-naturally occurring pyrimidine. For example, $B^1$ can be

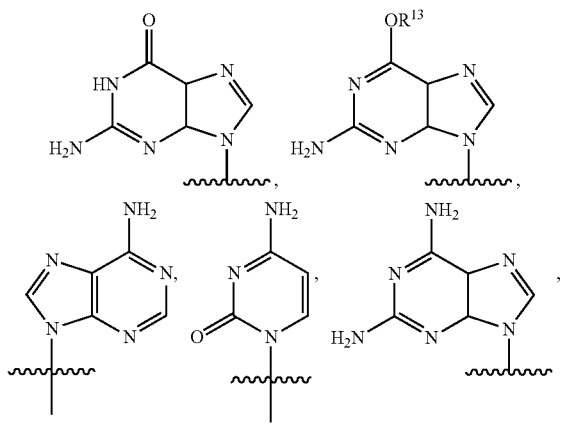

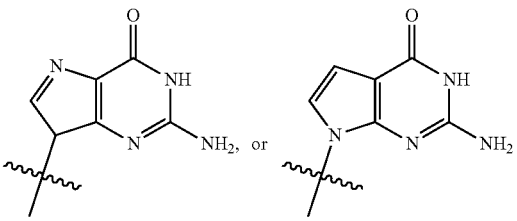

wherein $R^{13}$ can be an unsubstituted $C_{1-6}$ alkyl or an unsubstituted $C_{3-6}$ cycloalkyl. In some embodiments, $R^{13}$ can be methyl, ethyl, n-propyl, isopropyl, n-butyl, isobutyl, tert-butyl, pentyl (branched or straight chained) or hexyl (branched or straight chained). In other embodiments, $R^{13}$ can be cyclopropyl, cyclobutyl, cyclopentyl or cyclohexyl.

Examples of compounds of Formula (I), or a pharmaceutically acceptable salt thereof, include, but are not limited to:

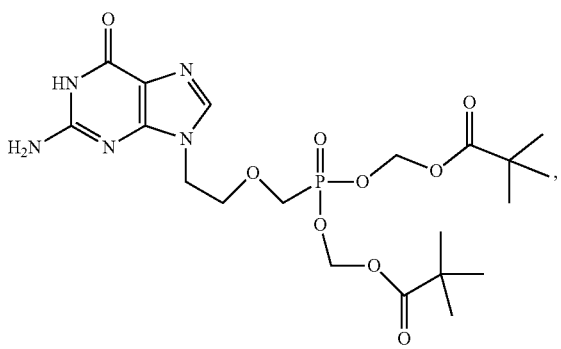

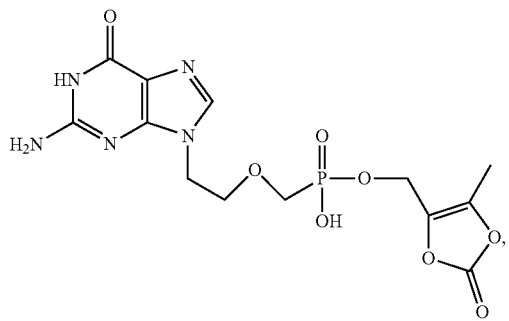

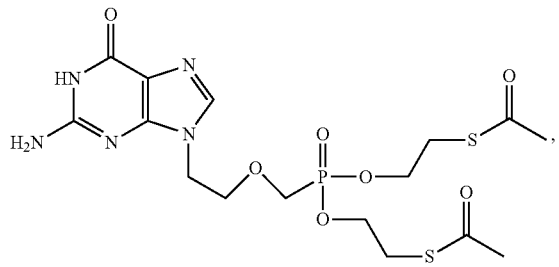

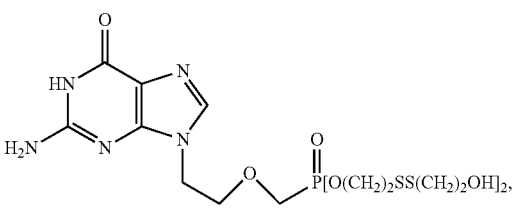

-continued

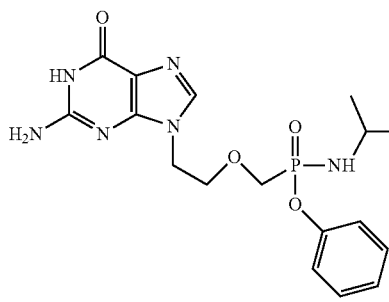

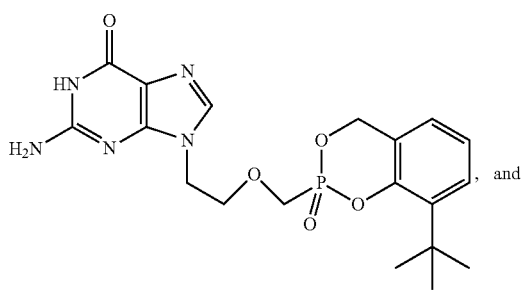

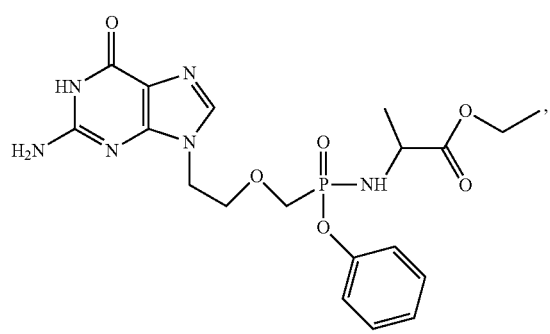

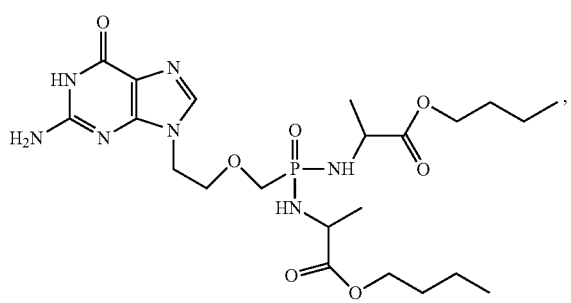

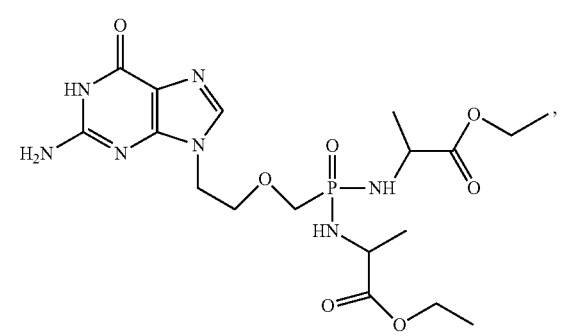

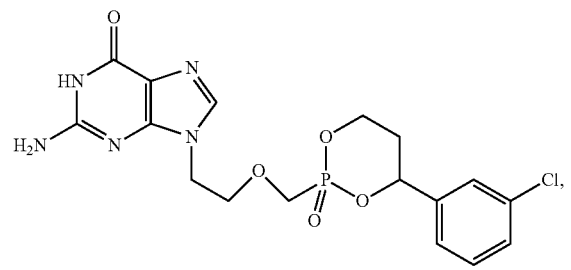

or a pharmaceutically acceptable salt of the foregoing.

In embodiments, there is provided a compound of the formula:

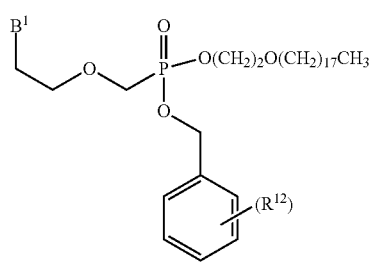

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

In embodiments, there is provided a compound of the formula:

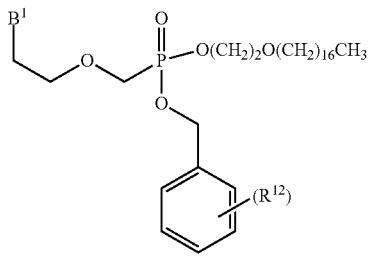

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

In embodiments, there is provided a compound of the formula:

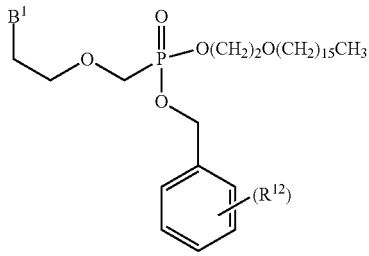

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

In embodiments, there is provided a compound of the formula:

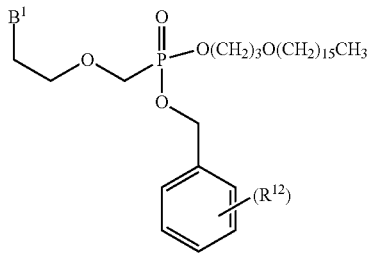

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

In embodiments, there is provided a compound of the formula:

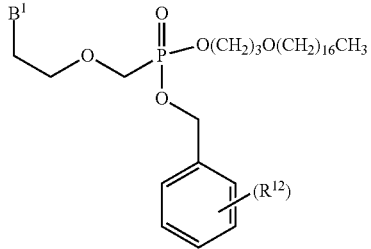

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

In embodiments, there is provided a compound of the formula:

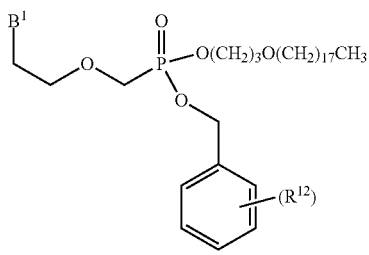

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

In embodiments, compounds have the formula:

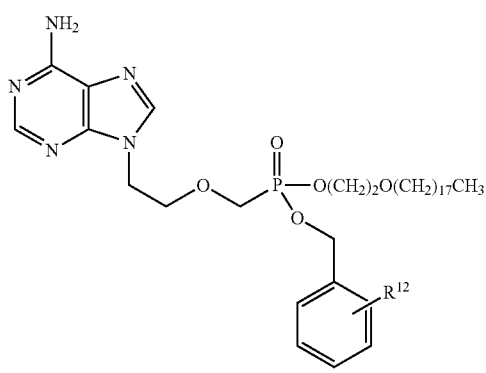

wherein $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group. The phenyl ring can be substituted by $R^{12}$ 1, 2 or 3 times.

In embodiments, compounds have the Formula:

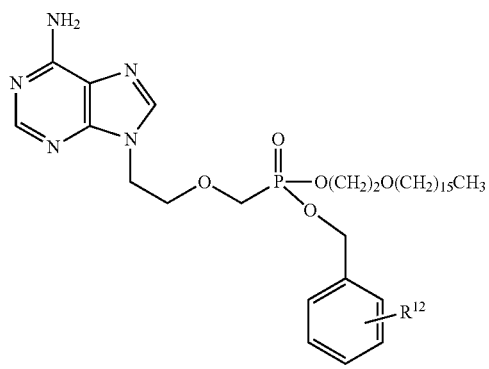

wherein $R^{12}$ is defined above. The phenyl ring can be substituted by $R^{12}$ 1, 2 or 3 times.

In embodiments, compounds have the Formula:

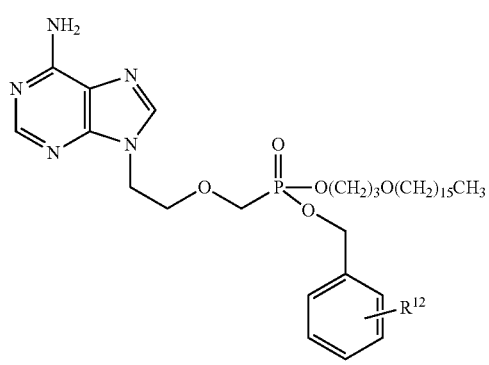

wherein $R^{12}$ is defined above. The phenyl ring can be substituted by $R^{12}$ 1, 2 or 3 times.

In embodiments, compounds have the Formula:

wherein $R^{12}$ is defined above. The phenyl ring can be substituted by $R^{12}$ 1, 2 or 3 times.

In embodiments, compounds have the Formula:

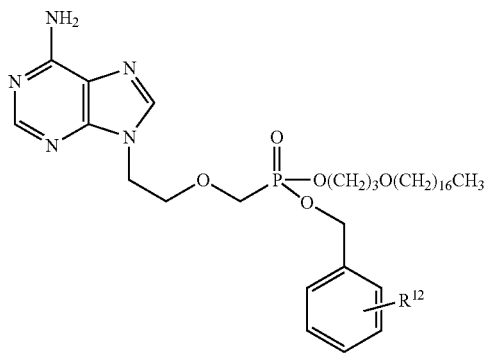

wherein R[12] is defined above. The phenyl ring can be substituted by R[12] 1, 2 or 3 times.

In embodiments, compounds have the Formula:

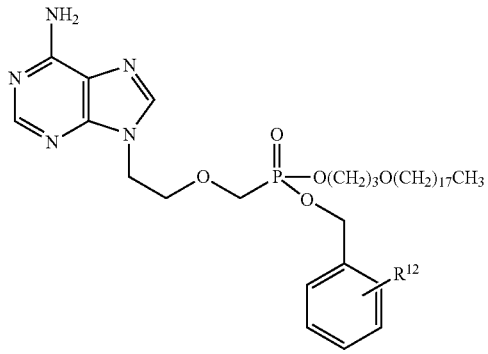

wherein R[12] is defined above. The phenyl ring can be substituted by R 1, 2 or 3 times.

In embodiments, compounds have the Formula:

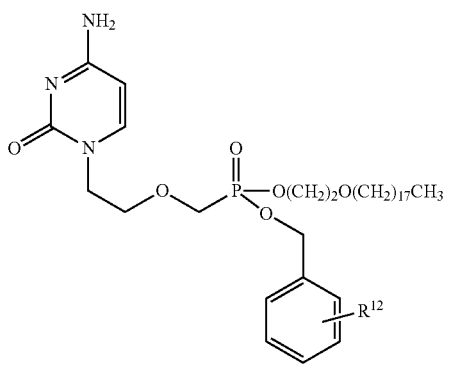

wherein R[12] is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group. The phenyl ring can be substituted by R[12] 1, 2 or 3 times.

In embodiments, compounds have the Formula:

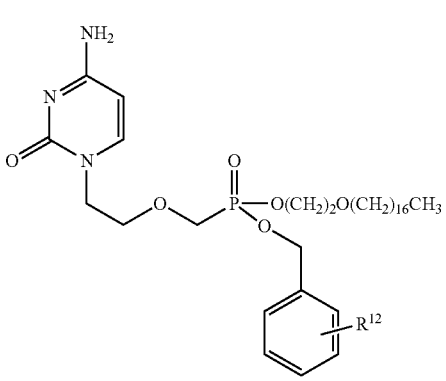

wherein R[12] is defined above. The phenyl ring can be substituted by R[12] 1, 2 or 3 times.

In embodiments, compounds have the Formula:

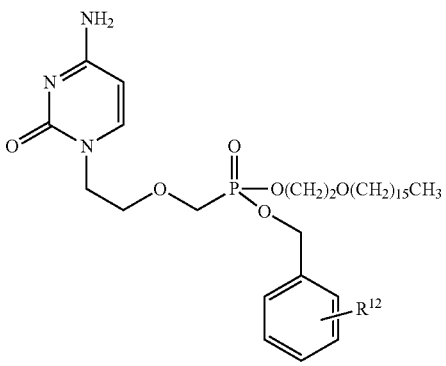

wherein R[12] is defined above. The phenyl ring can be substituted by R[12] 1, 2 or 3 times.

In embodiments, compounds have the Formula:

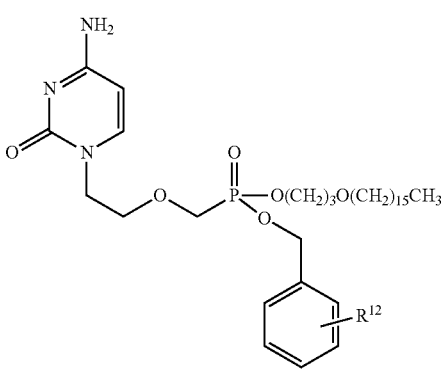

wherein R[12] is defined above. The phenyl ring can be substituted by R[12] 1, 2 or 3 times.

In embodiments, compounds have the Formula:

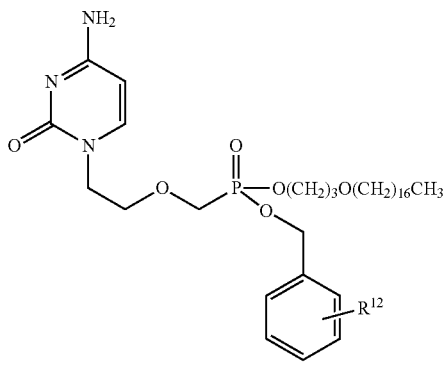

wherein $R^{12}$ is defined above. The phenyl ring can be substituted by $R^{12}$ 1, 2 or 3 times.

In embodiments, compounds have the Formula:

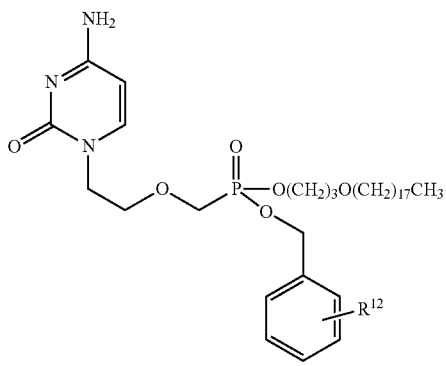

wherein $R^{12}$ is defined above. The phenyl ring can be substituted by $R^{12}$ 1, 2 or 3 times.

In embodiments, $R^{12}$ in a structure above is independently selected from alkyl, alkoxy, halogen and cyano.

In embodiments, $R^1$ is an optionally substituted heteroaryl, for example pyridine, pyrimidine, imidazole, pyrrole, furan or thiophene.

In embodiments, $R^1$ is an optionally substituted aryl include but not limited to phenyl.

In embodiments, $R^1$ is optionally substituted aryl($C_{1-4}$ alkyl).

In embodiments, $R^1$ is an optionally substituted heteroaryl, for example pyridine, pyrimidine, imidazole, pyrrole, furan or thiophene and $R^2$ is —$(CHR^4)_a$—O—($C_{1-24}$ alkyl or alkenyl). In some embodiments, $R^1$ is optionally substituted aryl including, but not limited, to phenyl and $R^2$ is —$(CHR^4)_a$—O—($C_{1-24}$ alkyl or alkenyl). In some embodiments, $R^1$ is optionally substituted aryl($C_{1-4}$ alkyl) and $R^2$ is —$(CHR^4)_a$—O—($C_{1-24}$ alkyl or alkenyl).

In some embodiments, when $R^1$ is —$(CH_2)_2$—O—$(CH_2)_{17}CH_3$, then $Z^2$ cannot be O and $R^2$ cannot be phenyl (a substituted or unsubstituted phenyl). In some embodiments, when $R^1$ is —$(CH_2)_2$—O—$(CH_2)_{17}CH_3$, then $Z^2$ cannot be O and $R^2$ cannot be benzyl (a substituted or unsubstituted benzyl). In some embodiments, when $R^1$ is —$(CH_2)_2$—O—$(CH_2)_{17}CH_3$, then $Z^2$ cannot be O and $R^2$ cannot be hydrogen. In some embodiments, when $R^1$ is —$(CH_2)_3$—O—$(CH_2)_{15}CH_3$, then $Z^2$ cannot be O and $R^2$ cannot be phenyl (a substituted or unsubstituted phenyl). In some embodiments, when $R^1$ is —$(CH_2)_3$—O—$(CH_2)_{15}CH_3$, then $Z^2$ cannot be O and $R^2$ cannot be benzyl (a substituted or unsubstituted benzyl). In some embodiments, when $R^1$ is —$(CH_2)_3$—O—$(CH_2)_{15}CH_3$, then $Z^2$ cannot be O and $R^2$ cannot be hydrogen. In some embodiments, $R^1$ cannot be —$(CH_2)_a$—O—$C_{1-24}$ alkyl. In some embodiments, the human papillomavirus cannot be HPV-16 and/or HPV-18. In some embodiments, the human papillomavirus cannot be HPV-11.

Pharmaceutical Compositions

Some embodiments described herein relates to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of ≥50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal, intravaginal and intraocular injections.

One may also administer the compound in a local rather than systemic manner, for example, via application of the compound directly to the infected area. The compound can be administered as a gel, a cream and/or a suppository. In addition, the compound can be administered in a depot or sustained release formulation (for example, as nanoparticles and/or an intravaginal ring). Furthermore, one may administer the compound in a targeted drug delivery system, for example, in a liposome coated with a tissue-specific antibody. The liposomes will be targeted to and taken up selectively by the organ.

The compositions may, if desired, be presented in a pack, applicator or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Synthesis

Compounds of Formula (I) and those described herein may be prepared in various ways. General synthetic routes to the compound of Formula (I) and some examples of starting materials used to synthesize compounds of Formula (I) are shown in Scheme 1 and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

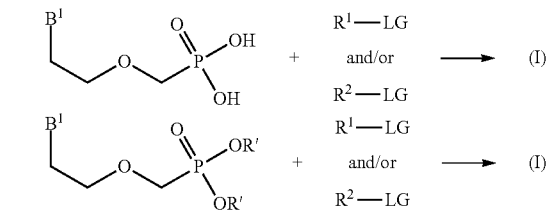

Scheme 1

A shown in Scheme 1, the acyclic nucleoside phosphonate can be coupled with $R^1$-LG and then with $R^2$-LG, wherein LG is a suitable leaving group (for example, Cl). Alternatively, the OH groups attached to the phosphorus can be transformed and then replaced with $R^1$ and $R^2$. For example, the hydrogens of the OH groups can be transformed to alkali metal ions, such as $Na^+$ (shown as R' in Scheme 1). Methods for coupling an acyclic nucleoside phosphonate are known to those skilled in the art. For examples, see methods described and referenced in Pradere, U. et al., Chem. Rev., 2014, 114:9154-9218.

An acyclic nucleoside phosphonate can be esterified by methods known to one skilled in the art and then reacted with an amine by methods known to one skilled in the art to generate a phosphoramidate ester of Formula I.

An acyclic nucleoside phosphonate can be reacted with an amine by methods known to one skilled in the art to generate a phosphoramidate and subsequently reacted with an amine by methods known to one skilled in the art to generate a bisphosphoramidate of Formula I.

Compounds of Formula I can be synthesized according to or analogously to the syntheses shown below. In certain embodiments, the person of ordinary skill in the art can replace guanine with another selected base described herein according to the present invention.

EXAMPLES

Example 1

9-[(2-phosphonomethoxy)ethyl]-2-amino-6-chloropurine, tributylamine salt (7)

Compound 6 was prepared as shown in Scheme A and converted to the phosphonic acid (6-a) by treatment with bromotrimethylsilane, followed by hydrolysis. The detailed methods are described in Holy, A. et al. J. Med. Chem. (1999) 42(12):2064-2086. To prepare 7, a 1 L flask was equipped with a magnetic stirrer, a nitrogen inlet, and an addition funnel. Compound 6-a (18.8 g, 61 mmol) and N,N-DMF (200 mL) were added, and the resulting slurry was stirred. Tributylamine (14.9 mL, 62 mmol) was added dropwise over 15-20 mins. The resulting solution was stirred at ambient temperature for 10 mins. Toluene (470 mL) was added, and stirring was continued for 30-40 mins. Seed crystals (50 mg) of compound 7 were added. The mixture was stirred for 5 h, after which the precipitated solids were filtered. The solids were washed with toluene (150 mL) and dried under vacuum for several hours to give 7 (25.6 g, 85% yield) as an off-white powder. The solid was analyzed by $^1$H NMR and $^{31}$P NMR spectroscopy. $^1$H NMR (DMSO-$d_6$) δ 8.20 (s, 1H), 6.91 (s, 2H), 4.20 (t, 2H), 3.81 (t, 2H), 3.45 (d, 2H), 2.73 (m, 2H), 1.51 (m, 2H), 1.26 (septet, 2H), 0.87 (t, 3H). The spectra were found to be consistent with 7.

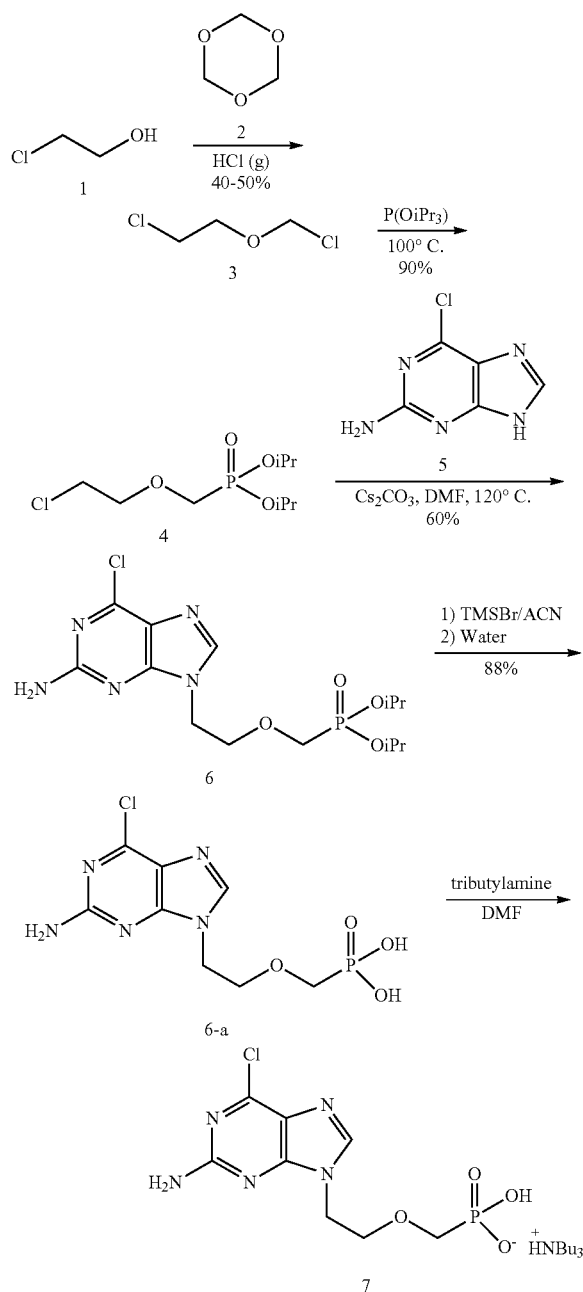

Example 2

9-[(2-phosphonomethoxy)ethyl]guanine (PMEG, 9)

Compound 9 was prepared by acidic hydrolysis of 6 as shown in Scheme B. Compound 6 (4.95 g, 12.6 mmol) was dissolved in 80% aq. CH₃COOH. The mixture was stirred and heated at reflux for 3 h. The mixture was then cooled. The solvent was evaporated under vacuum to give crude 8 as an off-white powder, which was dried in a vacuum oven at 45° C. Compound 8 was dissolved in CH₃CN (30 mL), treated with bromotrimethylsilane (11.6 g, 76 mmol) and stirred overnight. The mixture was evaporated under vacuum. Water/crushed ice (50 mL) was added to the residue. The slurry was stirred for 1 h, and the precipitate was collected by filtration to provide 9 (PMEG, 3.1 g, 85% yield). Additional details for preparing PMEG are described in Holy, A. et al. J. Med. Chem. (1999) 42(12):2064-2086.

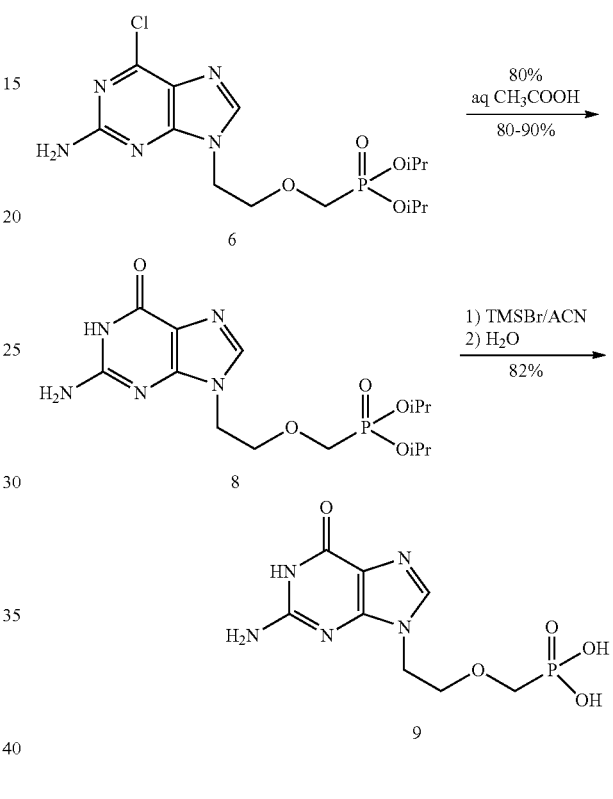

Example 3

Octadecyloxyethyl PMEG (ODE-PMEG, 11)

Method A: Compound 11 was prepared by esterification of 7 according to Scheme C. A 1 L flask was equipped with a magnetic stirrer, then compound 7 (21.7 g, 44 mmol), 2-octadecyloxyethanol (ODE-OH, 14.2 g, 45 mmol) and anhydrous N,N-DMF (300 mL) were added. The mixture was stirred and (benzotriazol-1-yloxy)-tripyrrolidinophosphonium hexafluorophosphate (PYBOP®, 35 g, 67.5 mmol) was subdivided in five equal portions (7 g each) and each portion was then added at 30 mins intervals. After the addition of PYBOP®, diisopropylethylamine (DIEA, 5.8 g, 45 mmol) and 1-hydroxybenzotriazole (HOBt, 3.0 g, 22.5 mmol) were added. The resulting mixture was stirred at 22-25° C., and the progress of the reaction was monitored by TLC (70:30:3:3 CHCl₃:MeOH:conc. NH₄OH:H₂O) on silica gel plates (Analtech, UNIPLATES™ Silica gel G, 250 microns). After the reaction was judged complete (16-20 h), the reaction mixture was slowly poured into a stirred acidic mixture comprised of conc. HCl (10 mL), water (750 mL) and crushed ice (750 mL). Stirring was continued for 10 mins. The precipitated solid was collected by filtration, washed with cold water (2×100 mL) and dried under vacuum to give crude 10 (32.7 g). The crude product was purified by silica gel column chromatography with elution of the product by CH$_2$Cl$_2$:MeOH 90:10 to yield 10 (9.5 g, 30.7% yield).

A 1 L reaction flask was equipped with a magnetic stirrer and a condenser. Compound 10 (9.5 g, 13.5 mmol), acetic acid (240 mL) and water (60 mL) were added. The resulting mixture was stirred and heated to reflux. The progress of the reaction was monitored by TLC (70:30:3:3 CHCl$_3$:MeOH:conc. NH$_4$OH:H2O) on silica gel plates (Analtech, UNIPLATES™ Silica gel G, 250 microns) using a UV lamp and charring. After the reaction was complete (3.5 h), the reaction mixture was cooled to 5° C., stirred for 2 h and filtered. The product was dried under vacuum to give 11 (7.5 g). The crude product was recrystallized in 80:20 isopropanol:water. After treatment with decolorizing carbon, the filtrate was allowed to cool to room temperature (RT) and then in an ice-bath. The precipitated solids were filtered and dried under vacuum to give 11 (6.2 g, 78%) as off-white powder.

Method B: Octadecyloxyethyl 9-[2-(phosphonomethoxy) ethyl]guanine (ODE-PMEG) was prepared according to the method described in Valiaeva, N. et al.; Antiviral Research (2006) 72:10-19.

mg, 4 mmol) and 1-hydroxybenzotriazole (HOBt, 270 mg, 2 mmol) were added. The reaction mixture was stirred at 22-25° C., and the progress of the reaction was monitored by TLC (70:30:3:3 CHCl$_3$:MeOH:conc. NH$_4$OH:H$_2$O) on silica gel plates (Analtech, UNIPLATES™ Silica gel G, 250 microns). After the reaction was judged complete (16-20 h), the reaction mixture was concentrated in vacuo. The crude product was purified by silica gel column chromatography with elution of the product by CH$_2$Cl$_2$:MeOH 55:45 to yield 12 (840 mg).

A 100 mL reaction flask was equipped with a magnetic stirrer and a condenser. Compound 12 (840 mg), acetic acid (24 mL) and water (6 mL) were added. The resulting mixture was stirred and heated to reflux. The progress of the reaction was monitored by TLC (70:30:3:3 CHCl$_3$:MeOH:conc. NH$_4$OH:H$_2$O) on silica gel plates (Analtech, UNIPLATES™ Silica gel G, 250 microns) using a UV lamp and charring. After the reaction was complete (3 h), the reaction mixture was evaporated under vacuum. The product was dried under vacuum to afford 13 (7.5 g). The crude product was purified by silica gel column chromatography with elution of the product by CH$_2$Cl$_2$:MeOH 50:50 to yield purified 13 (620 mg) as an off-white powder. $^1$H NMR (400

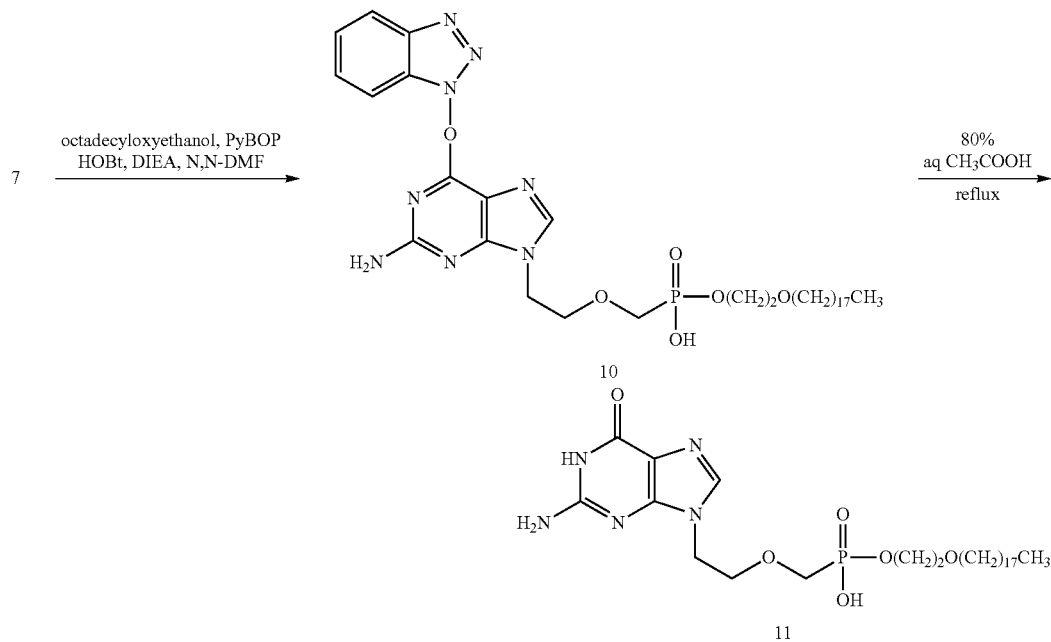

Example 4

BenzylPMEG (Bn-PMEG, 13)

Compound 13 was prepared by esterification of 7 with benzyl alcohol according to Scheme D. A 100 mL flask was equipped with a magnetic stirrer, then compound 7 (2.0 g, 4 mmol), benzyl alcohol (860 mg, 8 mmol) and anhydrous N,N-DMF (30 mL) were added. The mixture was stirred. (Benzotriazol-1-yloxy)-tripyrrolidinophosphonium hexafluorophosphate (PYBOP®, 3.2 g, 6 mmol) was sub-divided in five equal portions (640 mg each) and each portion was then added at 30 mins intervals. After the addition of PYBOP®, diisopropylethylamine (DIEA, 516

MHz, CDCl$_3$+methanol) δ 7.87 (s, 1 H) 7.20-7.36 (m, 5 H) 4.92 (d, J=7.33 Hz, 2 H) 4.17 (br. s., 2 H) 3.78 (br. s., 2 H) 3.66 (d, J=8.07 Hz, 2 H).

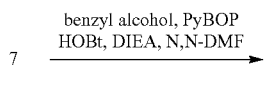

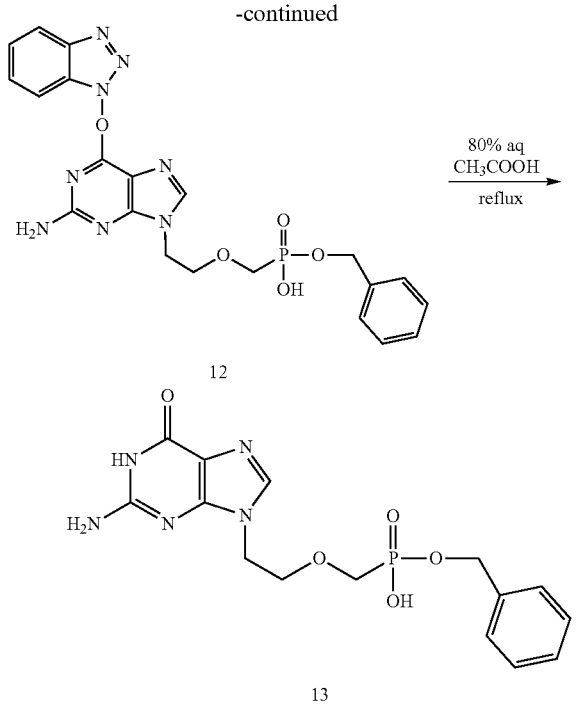

Example 5

1-O-Octadecyl-2-O-benzyl-sn-glyceryl PMEG (ODBG-PMEG, 14)

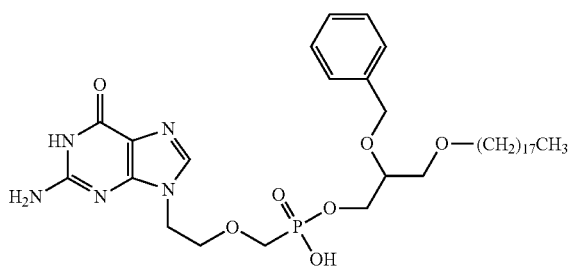

ODBG-PMEG was prepared by esterification of 7 with 1-O-octadecyl-2-O-benzyl-sn-glycerol (ODBG-OH). A 500 mL flask was equipped with a magnetic stirrer, then compound 7 (9.0 g, 18.25 mmol), ODBG-OH (20.7 mmol) and anhydrous N,N-DMF (200 mL) were added. The mixture was stirred and (benzotriazol-1-yloxy)-tripyrrolidinophosphonium hexafluorophosphate (PYBOP®, 15.6 g, 30 mmol) was subdivided in 3 equal portions (5.2 g each) and each portion was then added at 30 mins intervals. After the addition of PYBOP®, diisopropylethylamine (DIEA, 2.6 g, 20 mmol) and 1-hydroxybenzotriazole (HOBt, 1.2 g, 9 mmol) were added. The reaction mixture was stirred at 22-25° C., and the progress of the reaction was monitored by TLC (70:30:3:3 CHCl$_3$:MeOH:conc. NH$_4$OH:H$_2$O) on silica gel plates (Analtech, UNIPLATES™ Silica gel G, 250 microns). After the reaction was judged complete (16-20 h), the reaction mixture was concentrated in vacuo. The crude product was purified by silica gel column chromatography with elution of the product by CH$_2$Cl$_2$:EtOH 80:20 to yield the esterified intermediate (7.5 g, 50% yield).

A 500 mL reaction flask was equipped with a magnetic stirrer and a condenser. The esterified intermediate from the previous step (7.5 g), acetic acid (80 mL) and water (20 mL) were added. The resulting mixture was stirred and heated to reflux. The progress of the reaction was monitored by TLC (70:30:3:3 CHCl$_3$:MeOH:conc. NH$_4$OH:H$_2$O) on silica gel plates (Analtech, UNIPLATES™ Silica gel G, 250 microns) using a UV lamp and charring. After the reaction was complete (3 h), the reaction mixture was evaporated under vacuum. The crude product was purified by silica gel column chromatography with elution of the product by CH$_2$Cl$_2$:MeOH 80:20 to yield 14 (5.2 g, 81% yield) as an off-white powder.

Example 6

Acyloxyalkyl ester of 9-[2-(phosphonomethoxy)ethyl]-guanine

Acyloxyalkyl esters of PMEG are prepared using methods similar to those described by Srivasta, et al. Bioorg. Chem. (1984) 12:118-129 and Starrett et al. J. Med. Chem. (1994) 37 1857-1864. A typical approach to synthesis is shown in Scheme E.

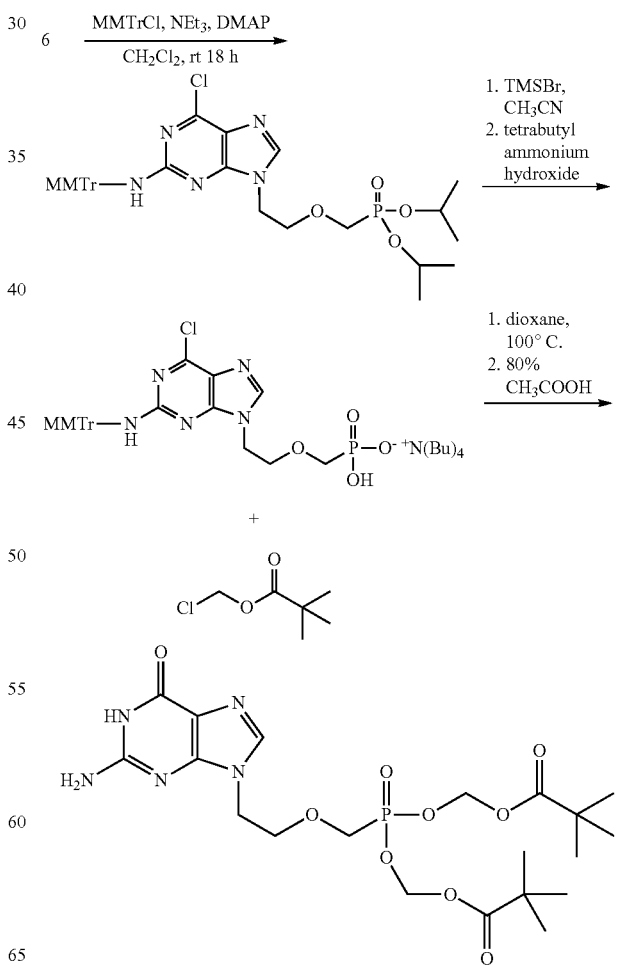

Example 7

(5-Methyl-2-oxo-1,3-dioxolen-4-yl)methyl ester of 9-[2-(phosphonomethoxy)-ethyl]guanine 9-[2-(phosphonomethoxy)ethyl]-guanine (PMEG) is neutralized with a 1M solution of methanolic tetrabutylammonium bromide in MeOH. The solution is evaporated and co-distilled with EtOH and toluene. The residue is dissolved in anhydrous DMF and treated with (5-methyl-2-oxo-1,3-dioxolen-4-yl)methyl bromide at RT for 4 days according to the procedure for preparing the corresponding adefovir prodrugs (see Tichý et al., Bioorg. & Med. Chem. (2011) 19(11):3527-3539.

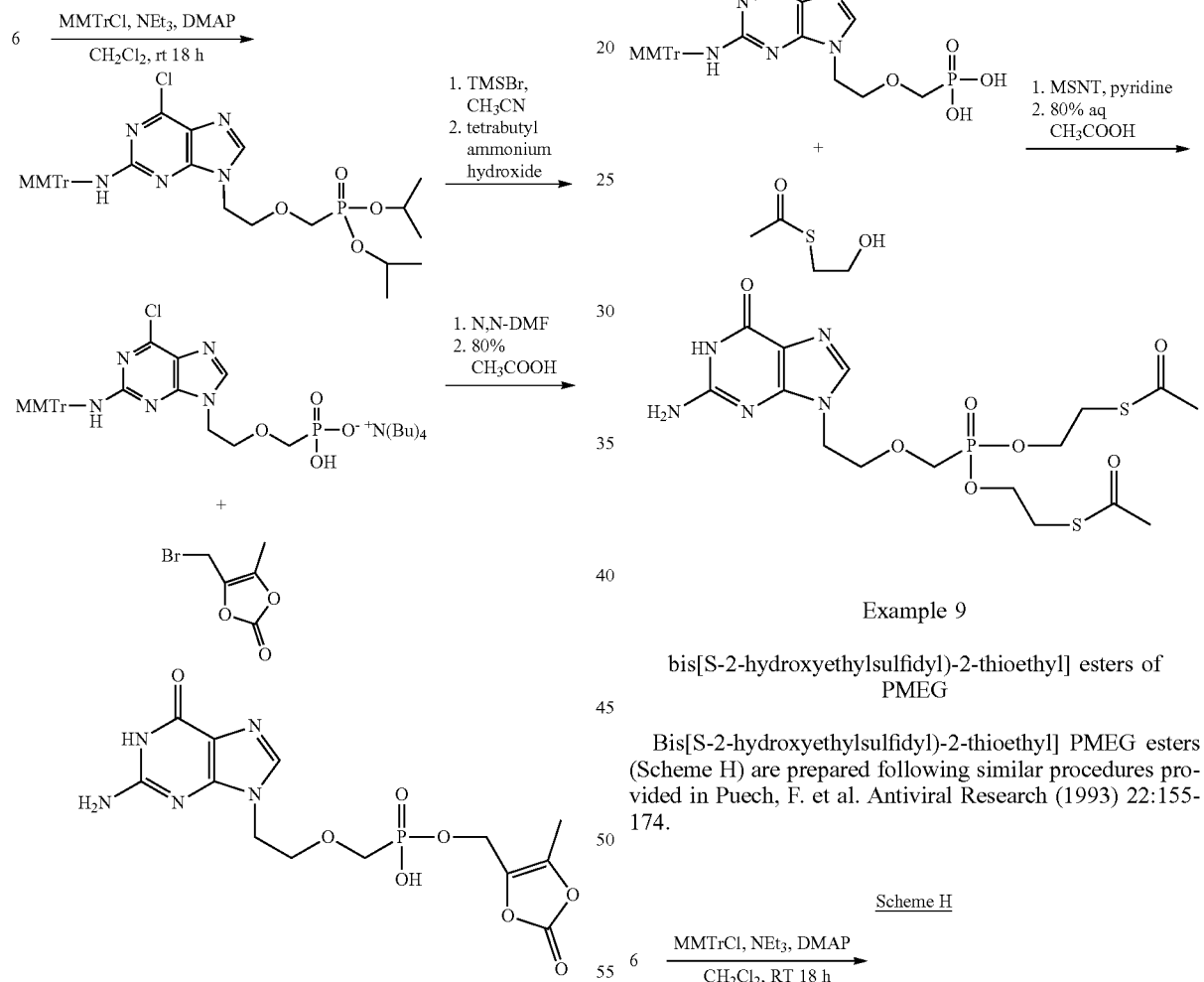

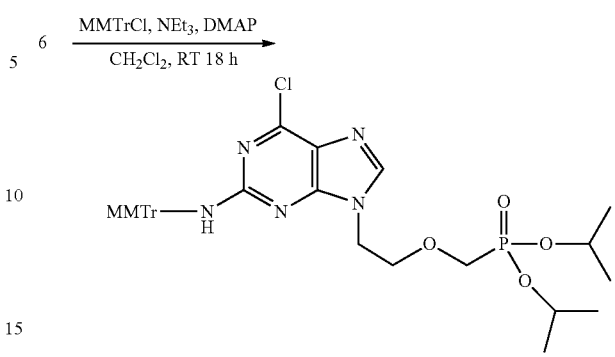

Example 8

S-acylthioethyl (SATE) esters of PMEG

The general procedure for the synthesis of (S-acylthioethyl) (SATE) esters of PMEG are shown in Scheme G. Procedures are analogous to those described for preparing the adefovir SATE esters in Benzaria, S. et al., J. Med. Chem. (1996) 39(25):4958-4965.

Example 9 bis[S-2-hydroxyethylsulfidyl)-2-thioethyl] esters of PMEG

Bis[S-2-hydroxyethylsulfidyl)-2-thioethyl] PMEG esters (Scheme H) are prepared following similar procedures provided in Puech, F. et al. Antiviral Research (1993) 22:155-174.

-continued

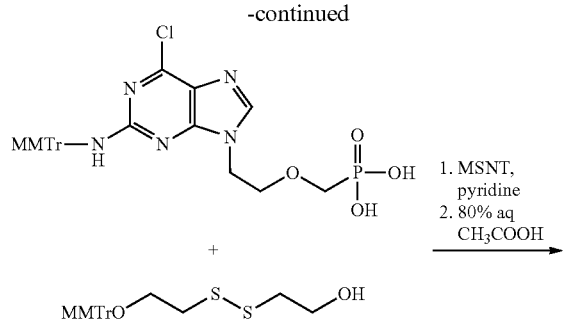

1. MSNT, pyridine
2. 80% aq CH₃COOH

Example 10

Aryl phosphonoamidate PMEG Prodrugs

Aryl phosphonoamidate PMEG prodrugs are prepared following similar procedures provided in U.S. Pat. No. 8,088,754. Examples are shown below.

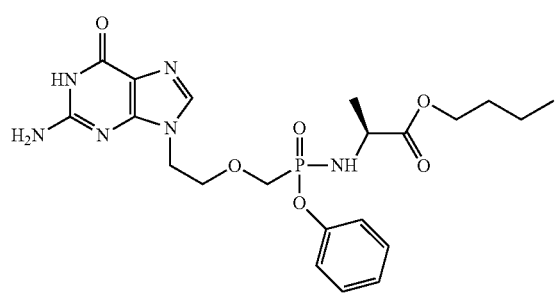

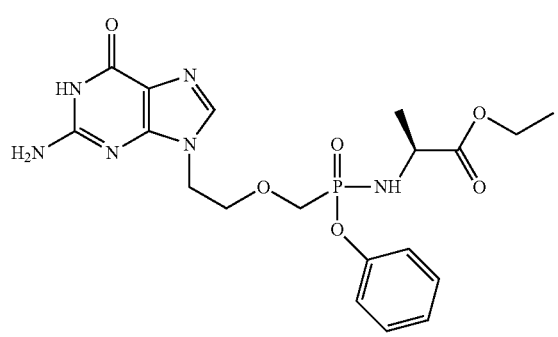

Synthesis of 9-[2-(phenyloxy-(ethoxy-L-alaninyl))-phosphonomethoxy)ethyl]guanine

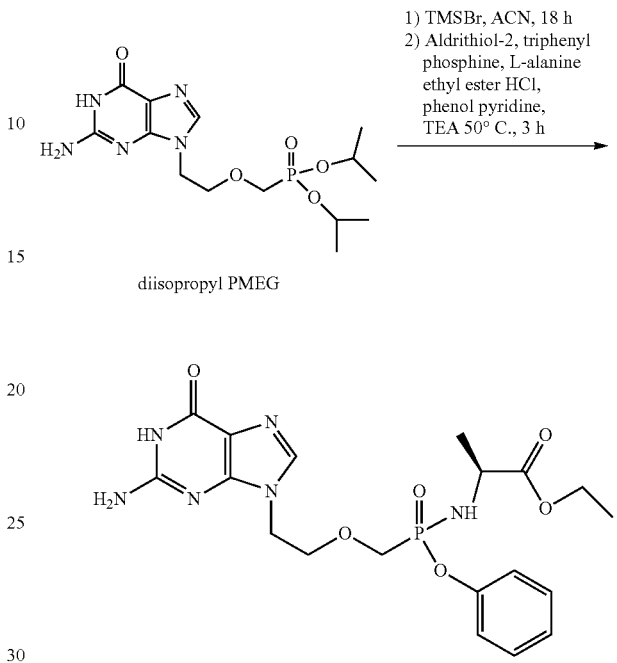

1) TMSBr, ACN, 18 h
2) Aldrithiol-2, triphenyl phosphine, L-alanine ethyl ester HCl, phenol pyridine, TEA 50° C., 3 h diisopropyl PMEG 9-[2-phenyloxy-(ethoxy-L-alaninyl))-phosphonomethoxy)ethyl]guanine To a solution of diisopropyl PMEG (1.0 g, 3 mmol) in dry acetonitrile (30 mL), bromotrimethylsilane (2.3 g, 15 mmol) was added and the reaction was stirred at room temperature overnight. The solvents were then removed under vacuum. The residue was dissolved in anhydrous Et3N (6 mL) and pyridine (25 mL), L-alanine ethyl ester HCl (0.69 g, 4.5 mmol) and phenol (0.42 g, 4.5 mmol) were added. A solution of Aldrithiol-2 (4.0 g, 18 mmol eq) and Ph₃P (4.7 g, 18 mmol) in anhydrous pyridine (30 ml) was added to the reaction. The resulting mixture was heated to 50° C. and stirred for 3 hours. After cooling, the solvents were removed under reduced pressure and the residue was adsorbed on silica gel. The product was isolated as a mixture of diastereomers by flash chromatography on silica gel eluted with 0 to 5% MeOH in dichloromethane (410 mg, 29%). ¹H NMR (DMSO-d₆) δ 10.65 (s, 2H), 7.69 (s, 1H), 7.68 (s, 1H), 7.35-7.30 (m, 4H), 7.17-7.11 (m, 6H), 6.52 (s, 4H), 5.71 (t, 4H), 5.64 (t, 4H), 4.15-4.11 (m, 2H), 4.03-3.99 (m, 2H), 3.91-3.81 (m, 4H), 3.36 (s, 2H), 3.07 (q, 2H), 1.20 (d, 3H), 1.15 (d, 3H), 1.13 (t, 6H). MS (ESI) 465.20 [M+H]+, 487.19 [M+Na]+, 509.17 M−H+2Na]+.

Example 11

Bis(phosphonoamidate) PMEG Prodrugs

Bis(phosphonoamidate) PMEG prodrugs are prepared following similar procedures provided in U.S. Pat. No. 8,088,754. Examples are shown below.

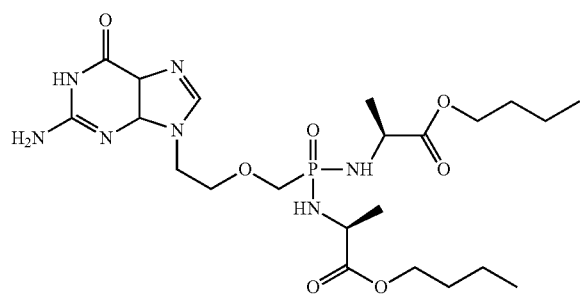

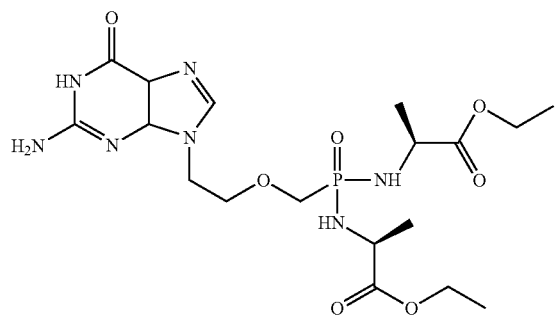

The compound 9-[2-(bis-(ethyloxy-L-alaninyl)-phosphonomethoxy)ethyl] guanine, illustrated above, was prepared as described in Lansa, P. et al. European Journal of Medicinal Chemistry, 2011, 46:3748-3754.

Example 12

Cyclic 1-aryl-1,3-propanyl PMEG esters

Cyclic 1-aryl-1,3-propanyl PMEG esters are prepared following similar procedures provided in Reddy, et al., J. Med. Chem. (2008) 51:666-676. A general procedure for preparing cyclic 1-aryl-1,3-propanyl PMEG esters is shown in Scheme I.

Scheme I

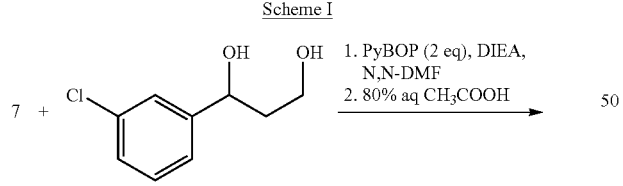

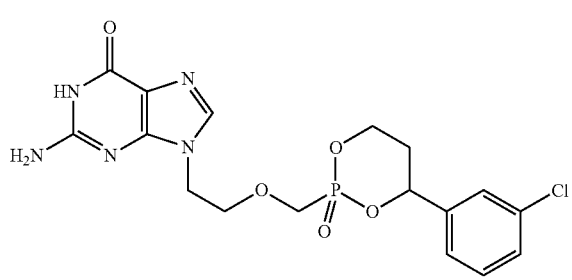

Example 13

Cyclosal PMEG esters

Cyclosal PMEG esters are prepared following similar procedures provided in Meier, C. et al., J. Med. Chem. (2005) 48:8079-8086. A general procedure for preparing cyclosal PMEG esters is shown in Scheme J.

Scheme J

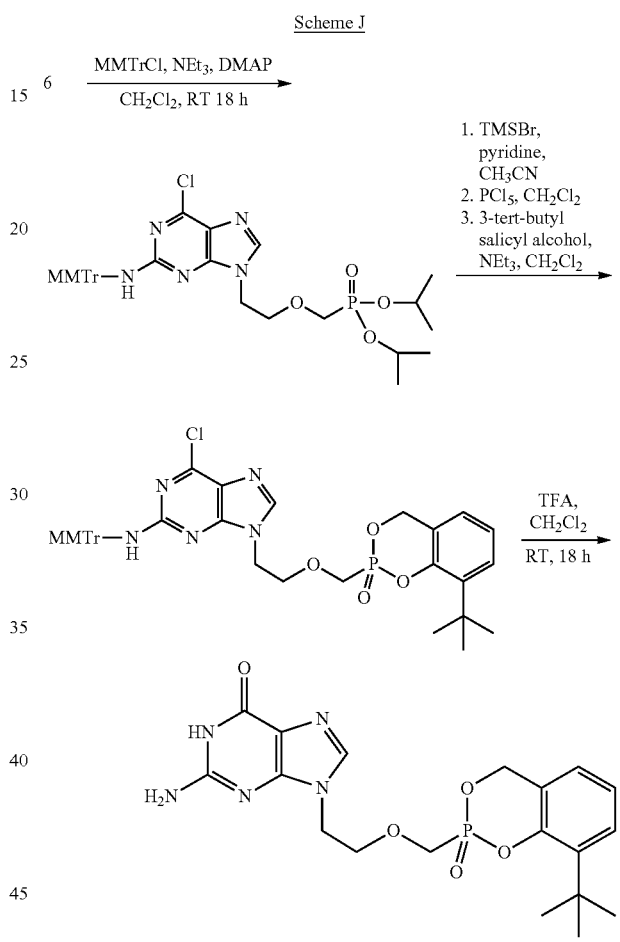

Example 14

Nitrofuranylmethyl PMEG Prodrugs

Nitrofuranylmethyl phosphonoamidate derivatives of PMEG are synthesized by sequential esterification of compound 7 with 5-nitrofurfuryl alcohol and N-methyl-N-4-chlorobutylamine as depicted in Scheme K. The nitrofuranylmethyl group has been shown (Tobias, S. C. et al., Mol. Pharmaceutics (2004) 1:112-116) to be readily taken up by cells, then cleaved intracellularly by a reductase enzyme which, in turn, leads to the formation of an intermediate chlorobutyl phosphonoamidate. Cyclization of the intermediate by nucleophilic attack of the nitrogen atom forms an N-phosphonotrialkyl ammonium species that can afford the unmasked phosphonate PMEG after hydrolysis.

Scheme K

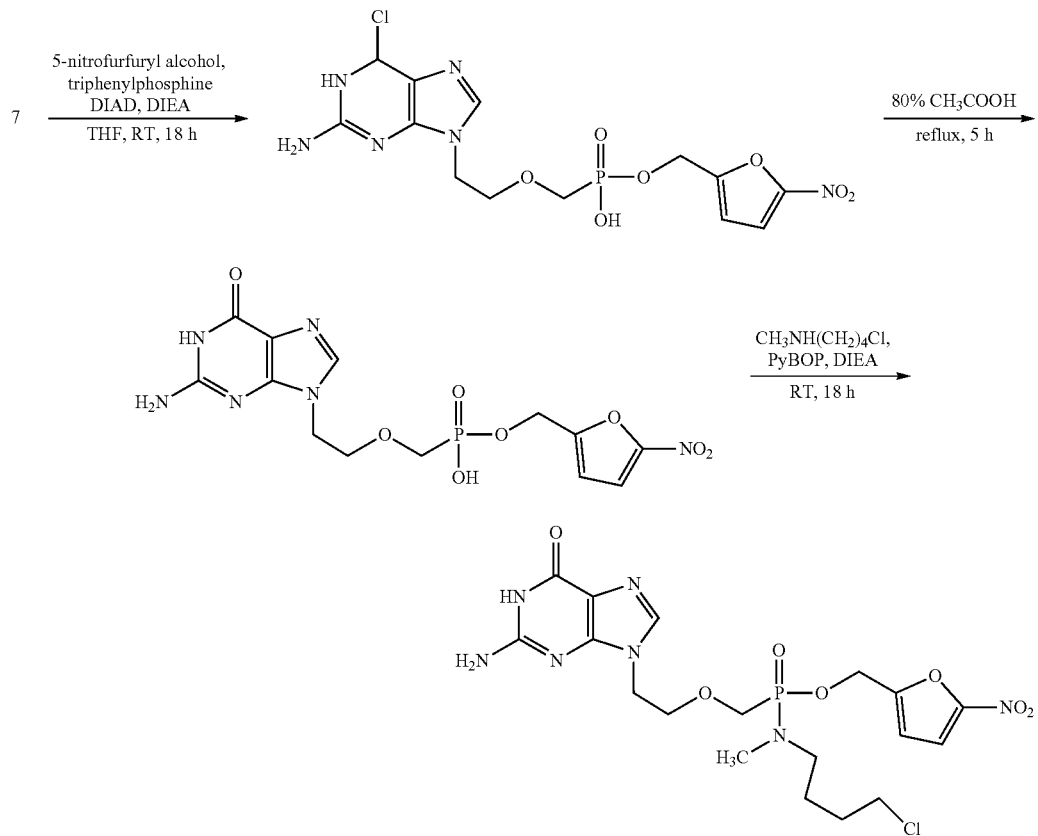

Example 15

Synthesis of ODE-(4-Me-Bn)-PMEG

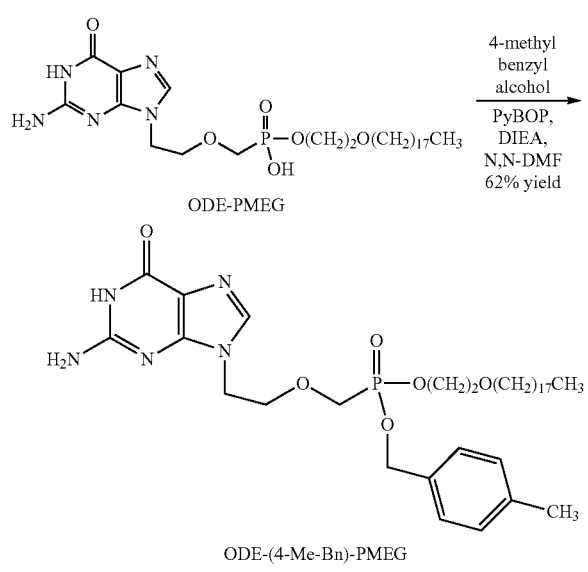

ODE-PMEG (150 mg, 0.26 mmol), 4-methylbenzyl alcohol (70 mg, 0.52 mmol) and (1H-bentriazol-1-yloxy)-tripyrrolidinophosphonium hexafluoride (PyBOP, 200 mg, 0.4 mmol) were weighed into a dried 100 mL round bottom flask. Anhydrous N,N-dimethylformamide (5 mL) and diisopropylethylamine (0.1 mL, 0.52 mmol) were then added and the reaction was stirred at room temperature for 4 hours. The mixture was then concentrated under vacuum to an oil. The residue was adsorbed on silica gel and the product was isolated by column chromatography on silica gel (eluant: 0 to 10% MeOH in dichloromethane) to yield ODE-(4-Me-Bn)-PMEG as an off-white waxy solid. (60 mg, 33% yield). $^1$H NMR (400 MHz, CDCl$_3$+methanol-d4) δ 7.64 (s, 1 H) 7.22-7.28 (m, 2 H) 7.15-7.20 (m, 2 H) 5.04 (dd, J=8.80, 2.20 Hz, 2 H) 4.19 (t, J=4.95 Hz, 2 H) 4.12 (m, 2 H) 3.82-3.87 (m, 2 H) 3.55-3.59 (m, 2 H) 3.43 (t, J=6.60 Hz, 2 H) 3.35 (dt, J=3.30, 1.65 Hz, 2 H) 2.35 (s, 3 H) 1.49-1.60 (m, 2 H) 1.16-1.37 (m, 30 H) 0.86 (t, J=7 Hz, 3H). MS (ESI): 690.67 (M+H)+, 712.53 (M+Na)+, 734.51 (M+2Na-H)+.

Example 16

Synthesis of ODE-(3-F-4-OMe-Bn)-PMEG

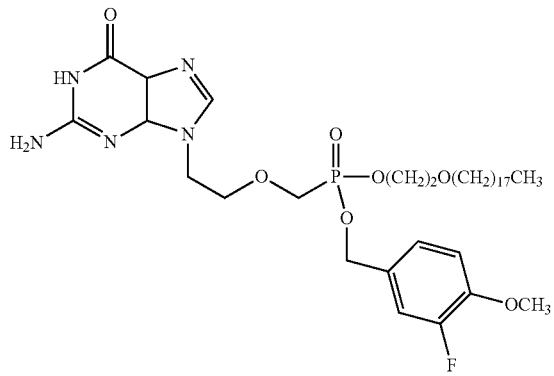

ODE-(3-F-4-OMe-Bn)-PMEG was prepared by the method of Example 4, using 3-fluoro-4-methoxybenzyl alcohol. The product was obtained as a waxy solid (100 mg, 52%). $^1$H NMR (400 MHz, CDCl$_3$+methanol-d4) δ 7.65 (s, 1 H) 7.06-7.17 (m, 2 H) 6.96-7.05 (m, 1 H) 5.00 (dd, J=8.80, 1.83 Hz, 2 H) 4.21 (t, J=5.13 Hz, 2 H) 4.14 (m, 2 H) 3.81-3.93 (m, 2 H) 3.59 (dd, J=4.95, 3.85 Hz, 2 H) 3.45 (t, J=6.78 Hz, 2 H) 3.35 (s, 3 H) 1.49-1.60 (m, 2 H) 1.07-1.45 (m, 30 H) 0.86 (t, J=7 Hz, 3H). MS (ESI): 724.56 (M+H)+, 746.49 (M+Na)+.

Example 17

Synthesis of ODE-(3-Cl-4-OMe-Bn)-PMEG

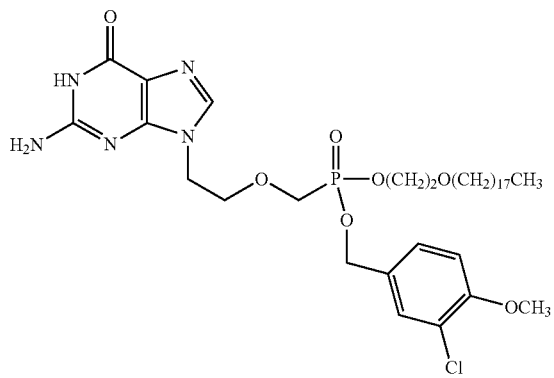

ODE-(3-Cl-4-OMe-Bn)-PMEG was prepared by the method of Example 4, using 3-chloro-4-methoxybenzyl alcohol. The product was obtained as a waxy solid (90 mg, 46%). $^1$H NMR (400 MHz, CDCl$_3$+methanol-d$_4$) δ ppm 7.66 (s., 1 H) 7.64-7.68 (m, 1 H) 7.38-7.42 (m, 1 H) 7.40 (d, J=2.20 Hz, 1 H) 4.95-5.05 (m, 2 H) 4.21 (t, J=5.13 Hz, 2 H) 4.11-4.17 (m, 2 H) 3.87-3.91 (m, 2 H) 3.84-3.89 (m, 2 H) 3.58 (dd, J=4.95, 3.85 Hz, 2 H) 3.44 (t, J=6.60 Hz, 2 H) 3.35 (s, 3 H) 1.51-1.59 (m, 2 H) 1.06-1.45 (m, 30 H) 0.89 (t, J=7 Hz, 3 H).). MS (ESI): 740.52 (M+H)+, 762.47 (M+Na)+.

Example 18

Synthesis of ODE-(3-F-Bn)-PMEG

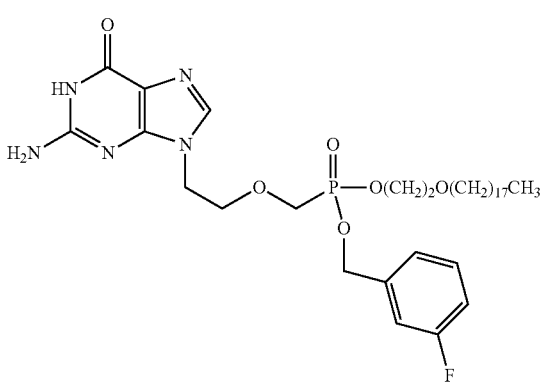

ODE-(3-F-Bn)-PMEG was prepared by the method of Example 4, using 3-fluorobenzyl alcohol. The product was obtained as an off-white solid (80 mg, 44%). $^1$H NMR (400 MHz, CDCl$_3$+methanol-d$_4$) δ 7.64 (s, 1 H) 7.42-7.50 (m, 1 H) 7.33-7.40 (m, 1 H) 6.97-7.19 (m, 2 H) 5.03-5.16 (m, 2 H) 4.11-4.25 (m, 4 H) 3.84-3.95 (m, 2 H) 3.55-3.65 (m, 2 H) 3.41-3.49 (m, 4 H) 3.35 (s, 3 H) 1.49-1.61 (m, 2 H) 1.07-1.39 (m, 30 H) 0.88 (t, J=7 Hz, 3 H). MS (ESI): 694.45 (M+H)+, 716.44 (M+Na)+, 738.44 (M+2Na-H)+.

Example 19

Synthesis of ODE-(3-Cl-Bn)-PMEG

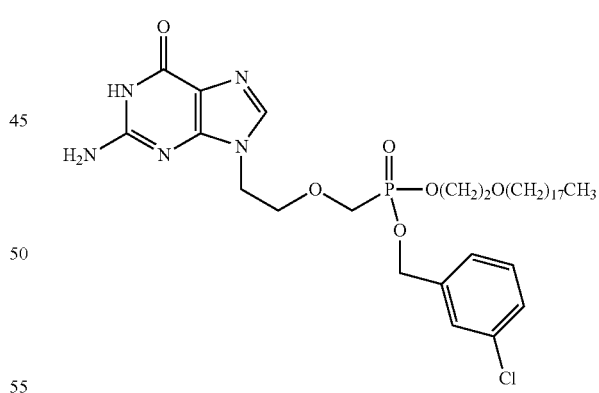

ODE-(3-Cl-Bn)-PMEG was prepared by the method of Example 4, using 3-chlorobenzyl alcohol. The product was obtained as an off-white solid (80 mg, 42%). $^1$H NMR (400 MHz, CDCl$_3$+methanol-d$_4$) δ 7.63 (s, 1H) 7.45 (t, J=6.42 Hz, 1 H) 7.23-7.41 (m, 3 H) 5.06 (d, J=8.80 Hz, 2 H) 4.17-4.21 (m, 4 H) 3.80-3.94 (m, 4 H) 3.59 (d, J=4.77 Hz, 2 H) 3.44 (t, J=6.78 Hz, 2 H) 3.36 (s, 4 H) 1.50-1.56 (m, 2 H) 1.11-1.24 (m, 30 H) 0.88 (t, J=6.78 Hz, 3 H). MS (ESI) [M+H]+ 710.46, [M+Na]+732.43.

Example 20

Synthesis of ODE-(3-picolyl)-PMEG

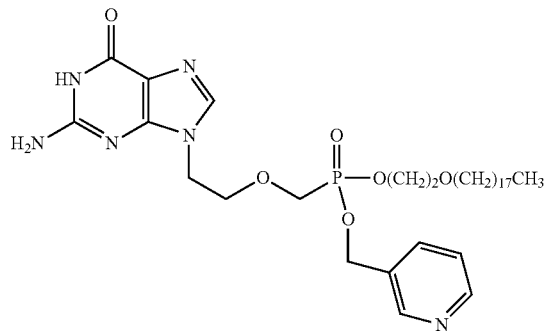

ODE-(3-picolyl)-PMEG was prepared by the method of Example 4, using 3-pyridinemethanol. The product was obtained as an off-white solid (110 mg, 40%). $^1$H NMR (400 MHz, CDCl$_3$+methanol-d$_4$) δ 7.60 (s, 1 H) 7.40-7.42 (m, 1 H) 7.23-7.31 (m, 3 H) 5.16 (d, J=8.80 Hz, 2 H) 4.15-4.20 (m, 4 H) 3.86-3.95 (m, 4 H) 3.56-3.60 (m, 2 H) 3.41-3.49 (m, 2 H) 3.36 (s, 3 H) 1.50-1.56 (m, 2 H) 1.11-1.24 (m, 30 H) 0.88 (t, J=6.78 Hz, 3 H). MS (EI): 677.46 (M+H)+, 699.47 (M+Na)+, 721.41 (M+2Na-H)+.

Example 21

Low Risk and High Risk HPV Assays

An origin-containing low risk or high risk HPV plasmid was co-transfected with homologous E1 and E2 protein expression vectors into HEK 293 cells. At 4 h post-transfection, cells were treated with test compound dilutions and then incubated for 48 h. HPV origin plasmid replication was detected after digestion with DpnI and exonuclease III to remove unreplicated transfected plasmids. Remaining replicated DNA was quantified by quantitative real time PCR (qPCR). In a parallel experiment in uninfected cells cytotoxicity was determined by trypan blue exclusion or CELL-TITER-GLO® to find the concentration that reduced viable cell number by 50% (CC50). $CC_{50}$ values were determined by trypan blue exclusion or CELLTITER-GLO® and the selectivity index calculated (Selectivity index=$CC_{50}/EC_{50}$). The low risk HPV tested was HPV-11, and the high-risk HPV tested was HPV-16 and HPV-18.

The results are provided in Table A and Table B. As shown in Table A, compounds of Formula (I) are active against both low-risk and high-risk HPV.

TABLE A

| Compound | Low Risk | High Risk |
|---|---|---|
| PMEG | C | C |
| ODE-PMEG | A | A |
| ODBG-PMEG | B | B |

'A' indicates an $EC_{50}$ < 0.3 μM, 'B' indicates an $EC_{50}$ of ≥0.3 μM and <3.0 μM and 'C' indicates an $EC_{50}$ ≥ 3.0 μM and <30 μM. For all the tested compounds, the selectivity indexes were >10.

The results are provided in Table B. As shown in Table B, compounds of Formula (I) are active against both low-risk and high-risk HPV.

TABLE B

Antiviral Activity against HPV-11 in HEK-293 Cells

| Compound | $EC_{50}$ (μM) | $EC_{90}$ (μM) | $CC_{50}$ (μM) | $SI_{50}$ |
|---|---|---|---|---|
| ODE-(4-Me-Bn)-PMEG | 0.93 ± 0.91 | 7.0 ± 3.45 | 23.80 ± 19.52 | 26 |
| ODE-(3-F-4-OMe-Bn)-PMEG | 0.18 ± 0.04 | 0.99 ± 0.13 | 14.25 ± 9.48 | 79 |
| ODE-(3-Cl-4-OMe Bn)-PMEG | 0.68 ± 0.62 | 1.34 ± 0.78 | 8.31 ± 1.83 | 12 |
| ODE-(3-F-Bn)-PMEG | 0.26 ± 0 | 1.59 ± 0.57 | 1.74 ± 0.03 | 7 |
| PMEG bisamidate Example 11 | 5.04 ± 7.01 | >100 ± 0 | >100 ± 0 | >20 |
| PMEG phenoxy amidate Example 10 | 7.56 ± 0.63 | >100 ± 0 | >100 ± 0 | >13 |
| ODE-(3-Cl-Bn)-PMEG | 0.22 ± 0.19 | >0.4 ± 0 | 1.11 ± 0.27 | 5 |
| Cidofovir | 41.71 ± 12 | >300 ± 0 | >300 ± 0 | >7 |

Example 22

Cytotoxicity Assay

Cytotoxicity Assays in HEK-293 cells. Cytotoxicity assays are performed in concurrently with every antiviral assay using the same cell line and media to ensure the same compound exposure. For the antiviral studies against HPV11 in HEK-293 cells, transfected cells are seeded in duplicate plates. Following a 2 h exposure, compound dilutions are prepared in both the antiviral plate and the duplicate cytotoxicity plate. At 48 h following compound addition, CELL-TITER-GLO® (Promega) is added to each well and luminescence is determined on a luminometer. Concentrations of compounds sufficient to reduce cell viability by 50% are calculated from the experimental data ($CC_{50}$ values).

Cytotoxicity Assays in Primary Human Foreskin Fibroblast Cells. Cytotoxicity was also evaluated in human foreskin fibroblast (HFF) cells as they are a highly sensitive indicator of toxicity in a standard assay with 7 d of compound exposure. A total of 4000 cells/well are seeded in 384-well plates in cell culture media containing 2% fetal bovine serum and antibiotics. Following a 24 h incubation, 5-fold compound dilutions are performed in duplicate wells directly in the plates containing monolayers of HFF cells. At 7 d following compound addition, CELLTITER-GLO® reagent is added to each well and resulting luminescence is measured on a luminometer to assess the number of viable cells in each well. Data are then used to calculate $CC_{50}$ values. The data is disclosed in Table 3 below.

TABLE 3

Cytotoxicity Results (CELLTITER-GLO ®)

| Compound | ($CC_{50}$, µM) | |
|---|---|---|
| | HEK293 (2 d incubation) | HFF (7 d incubation) |
| ODE-(4-Me-Bn)-PMEG | 32.01 ± 8.14 | 6.02 ± 3.79 |
| ODE-(3-F-4-OMe-Bn)-PMEG | 13.08 ± 5.17 | 1.72 ± 0.66 |
| ODE-(3-Cl-4-OMe-Bn)-PMEG | 8.87 ± 1.20 | 2.27 ± 0.51 |
| ODE-(3-F-Bn)-PMEG | 2.16 ± 0.36 | 6.88 ± 4.92 |
| PMEG bisamidate Example 11 | >100 ± 0 | >100 ± 0 |
| PMEG phenoxy amidate Example 10 | >100 ± 0 | 70.93 ± 4.07 |
| ODE-(3-Cl-Bn)-PMEG | 1.0 ± 0.16 | 4.65 ± 1.73 |
| Cidofovir | >300 ± 0 | >300 ± 0 |

Example 23

Synthesis of 9-[(2-phosphonomethoxy)ethyl]-2-amino-6-methoxypurine, tributylamine salt, 1, alternate name. ((2-(2-amino-6-methoxy-9H-purin-9-yl)ethoxy)methyl)phosphonic acid, tributylamine salt

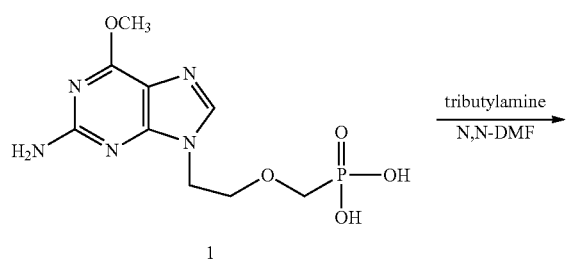

The scheme above provides a chemical synthetic scheme to afford 9-[(2-phosphonomethoxy)ethyl]-2-amino-6-methoxypurine, tributylamine salt.

Example 24

Synthesis of octadecyloxyethyl 9-[(2-phosphonomethoxy)ethyl]6-O-Me-guanine

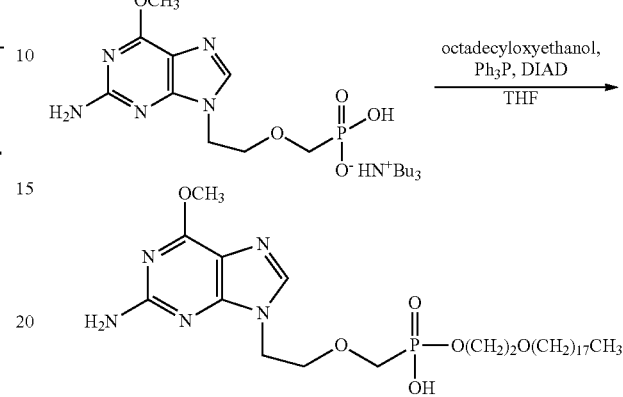

Example 25

Synthesis of benzyl 9-[(2-phosphonomethoxy)ethyl]6-O-Me-guanine

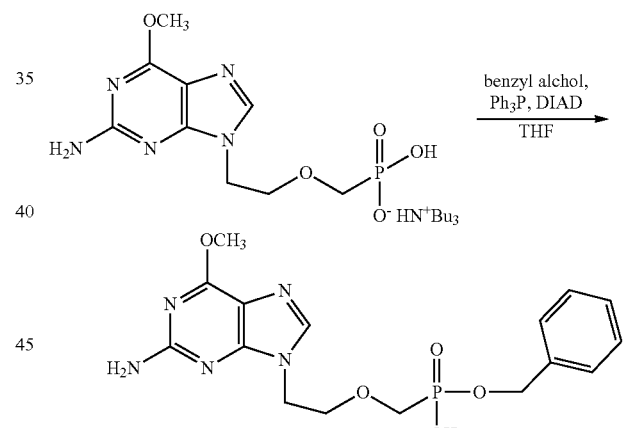

Example 26

Synthesis of 1-O-octadecyl-2-O-benzyl-sn-glyceryl 9-[(2-phosphono-methoxy)ethyl]6-O-Me-guanine

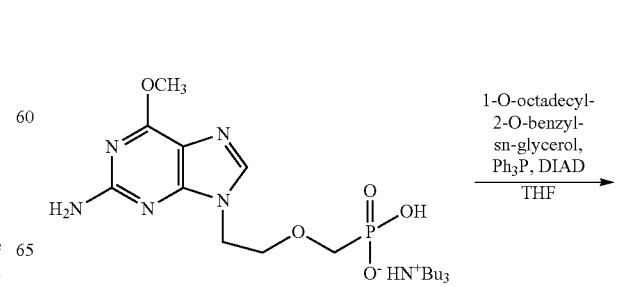

91
-continued

Example 27

Synthesis of (5-methyl-2-oxo-1,3-dioxol-4-yl) methyl hydrogen ((2-(2-amino-6-methoxy-9H-purin-9-yl)ethoxy)methyl)phosphonate

92

Example 28

Synthesis of S,S'-(((((2-(2-amino-6-methoxy-9H-purin-9-yl)ethoxy)methyl)phosphoryl)bis(oxy))bis(ethane-2,1-diyl)) diethanethioate Example 29

Synthesis of bis(2-((2-hydroxyethyl)sulfinothioyl)ethyl) ((2-(2-amino-6-methoxy-9H-purin-9-yl)ethoxy)methyl)phosphonate

Example 30
Synthesis of 2-amino-9-(2-((4-(3-chlorophenyl)-2-oxido-1,3,2-dioxaphosphinan-2-yl)methoxy)ethyl)-1,9-dihydro-6H-purin-6-one
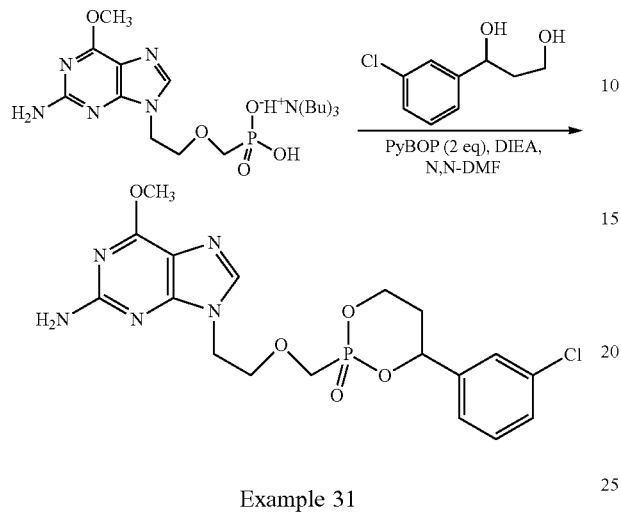
Example 31
Synthesis of 2-((2-(2-amino-6-hydroxy-9H-purin-9-yl)ethoxy)methyl)-8-(tert-butyl)-4H-benzo[d][1,3,2]dioxaphosphinine 2-oxide
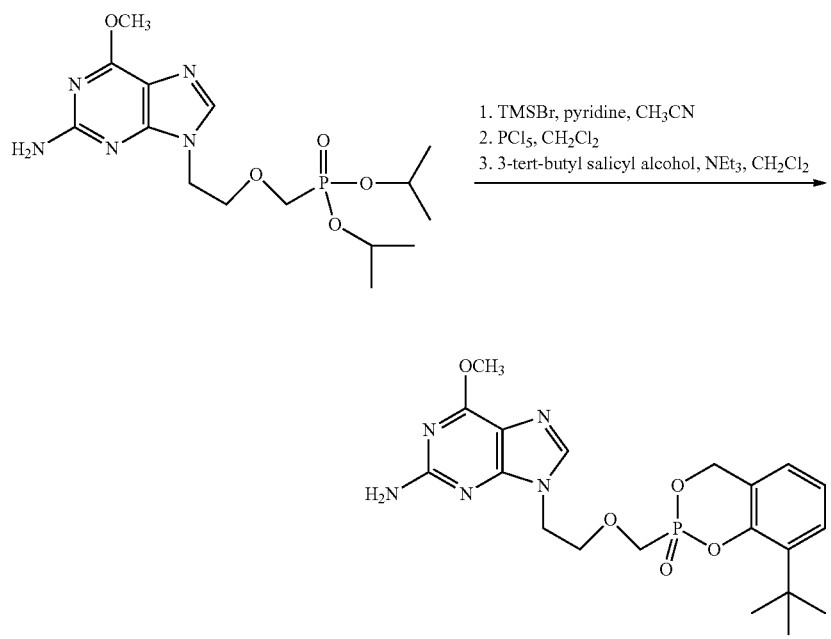
Example 32
Synthesis of (5-nitrofuran-2-yl)methyl P-((2-(2-amino-6-methoxy-9H-purin-9-yl)ethoxy)methyl)-N-(4-chlorobutyl)-N-methylphosphonamidate

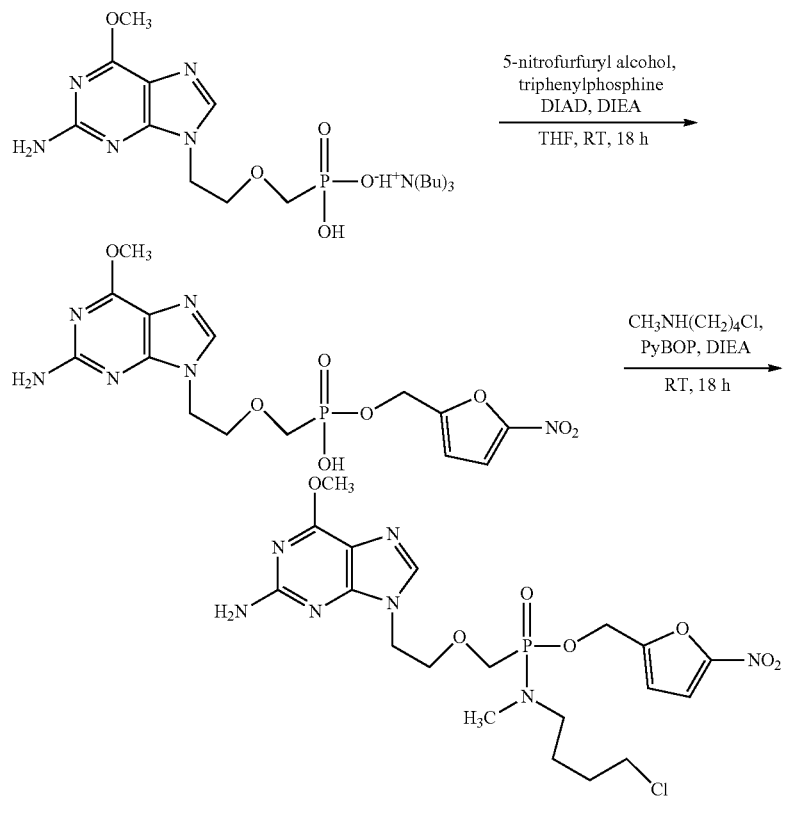
Example 33
Synthesis of dibenzyl PMEG
Dibenzyl PMEG can be prepared from benzyl PMEG, Example 4, as illustrated below.
Example 34
Synthesis of dibenzyl 9-[(2-phosphonomethoxyl)ethyl] 6-OMe-guanine
Dibenzyl 9-[(2-phosphonomethoxyl)ethyl] 6-OMe-guanine can be prepared from 9-[(2-phosphonomethoxy)ethyl]-2-amino-6-methoxypurine, tributylamine salt (Example 23).
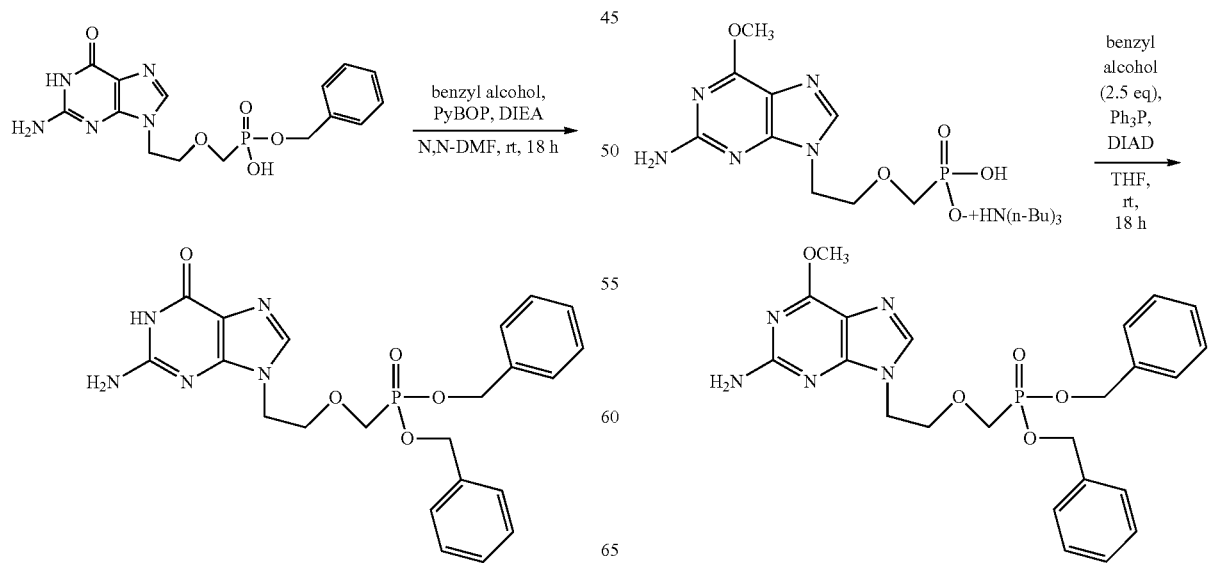

Example 35

Synthesis of octadecyloxyethyl benzyl 9-[(2-phosphonomethoxyl)ethyl] 6-OMe-guanine The compound octadecyloxyethyl benzyl 9-[(2-phosphonomethoxyl)ethyl] 6-OMe-guanine can be prepared from 9-[(2-phosphonomethoxy)ethyl]-2-amino-6-methoxypurine, tributylamine salt (Example 23) as illustrated below.

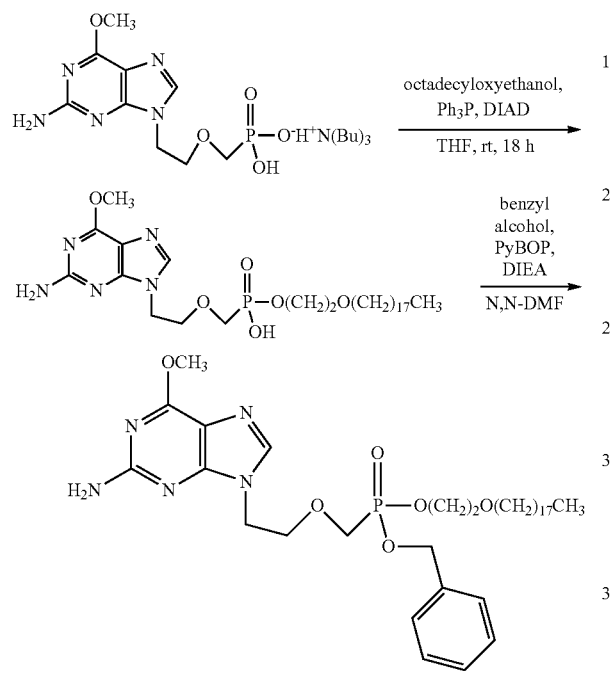

Example 36

Synthesis of hexadecyloxypropyl benzyl 9-[(2-phosphonomethoxyl)ethyl]6-OMe-guanine The compound hexadecyloxypropyl benzyl 9-[(2-phosphonomethoxyl)ethyl] 6-OMe-guanine can be prepared from 9-[(2-phosphonomethoxy)ethyl]-2-amino-6-methoxypurine, tributylamine salt (Example 23) as illustrated below.

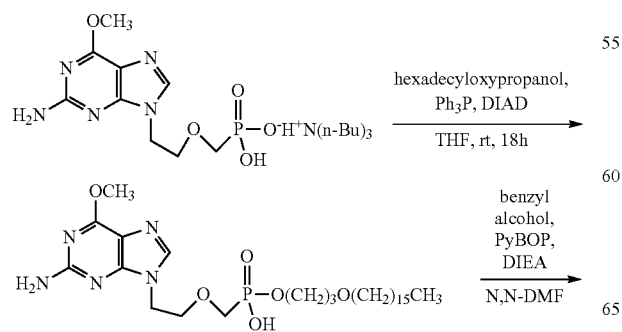

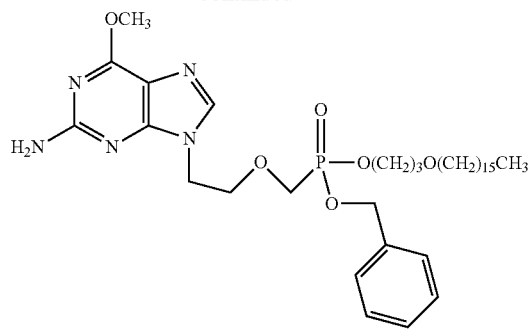

Example 37

Synthesis of a Nitrofuranylmethyl PMEG Prodrug

Benzyl PMEG is treated with 5-nitrofurfuryl alcohol, ByBOP, diisopropylethylamine, and N,N-dimethylformamide for 18 hours at room temperature as illustrated below.

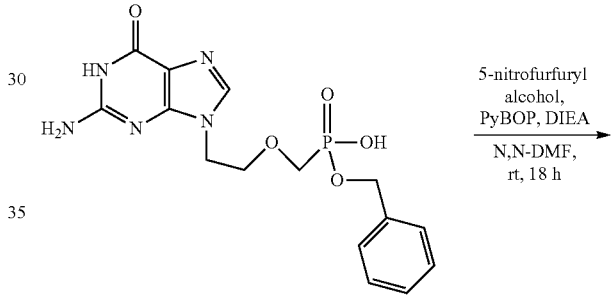

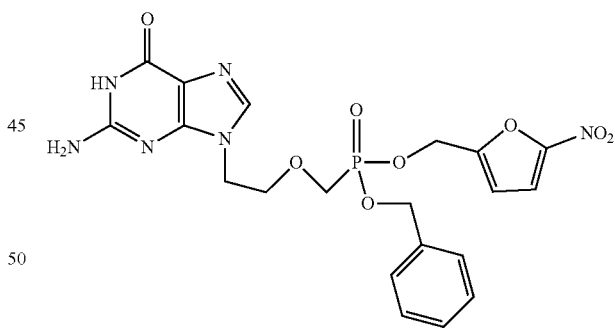

Example 38

Synthesis of a Nitrofuranylmethyl Benzyl Prodrug

The compound benzyl 9-[(2-phosphonomethoxyl)ethyl] 6-OMe-guanine is treated with 5-nitrofurfuryl alcohol, ByBOP, diisopropylethyl amine, and N,N-dimethylformamide for 18 hours at room temperature as illustrated below.

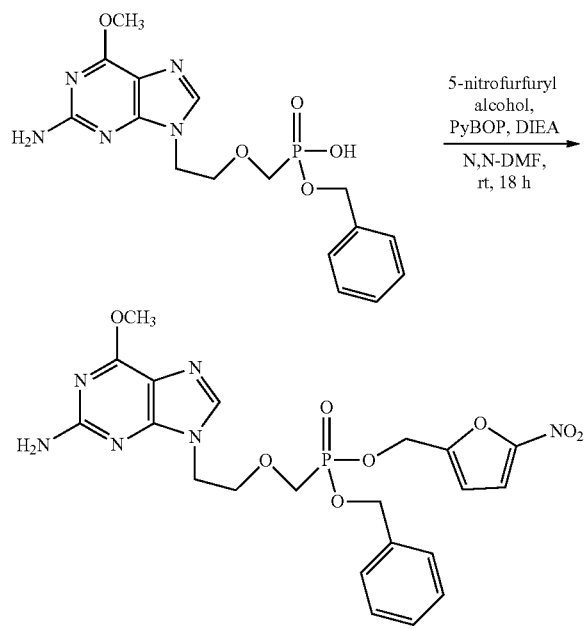

Example 39

Synthesis of 9-[2-(benzyloxy-(ethoxy-D-alanyl)-phosphonomethoxyl)ethyl]guanine

The compound 9-[2-(benzyloxy-(ethoxy-D-alanyl)-phosphonomethoxyl)ethyl]guanine is synthesized as illustrated below.

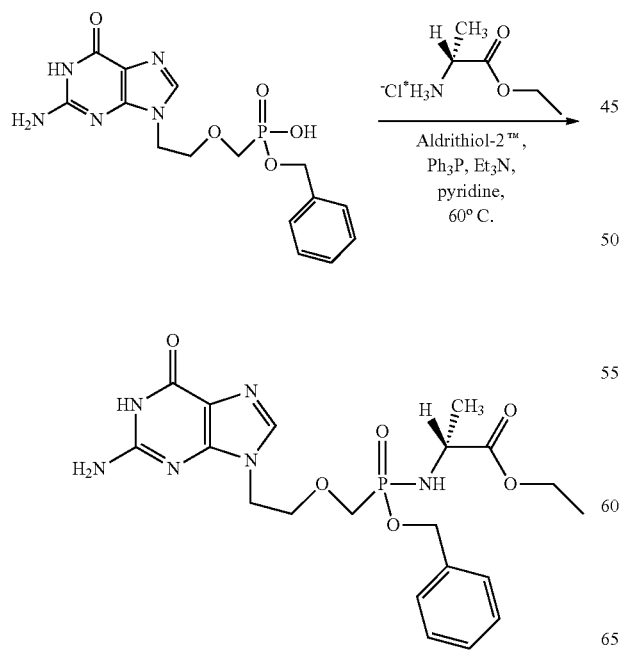

Example 40

Synthesis of 9-[2-(benzyloxy-(ethoxy-L-alanyl)-phosphonomethoxyl)ethyl]guanine

The compound 9-[2-(benzyloxy-(ethoxy-L-alanyl)-phosphonomethoxyl)ethyl]guanine is synthesized as illustrated below.

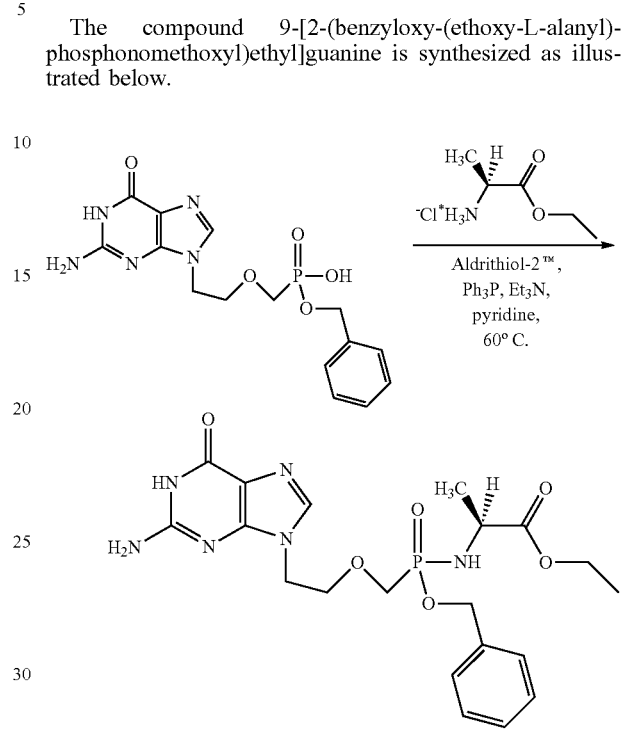

Example 41

Synthesis of 9-[2-(benzyloxy-(ethoxy-D-alanyl)-phosphonomethoxyl)ethyl]6-OMe guanine The compound 9-[2-(phenoxy-(ethoxy-D-alanyl)-phosphonomethoxyl)ethyl] 6-OMe guanine is synthesized as illustrated below.

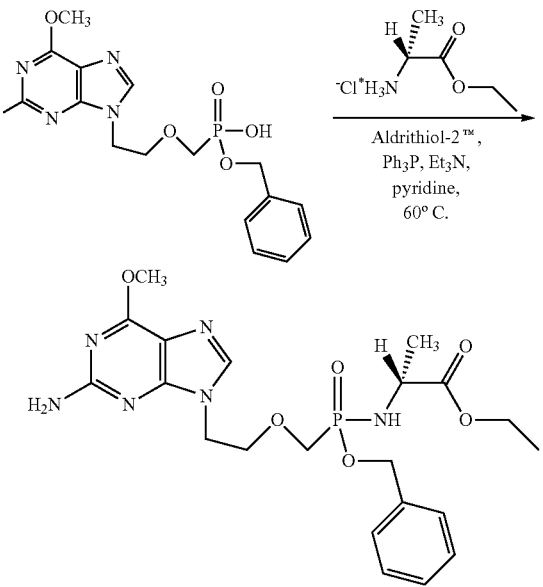

Example 42

Synthesis of 9-[2-(benzyloxy-(ethoxy-L-alanyl)-phosphonomethoxyl)ethyl]6-OMe guanine The compound 9-[2-(phenoxy-(benzyloxy-L-alanyl)-phosphonomethoxyl)ethyl] 6-OMe guanine is synthesized as illustrated below.

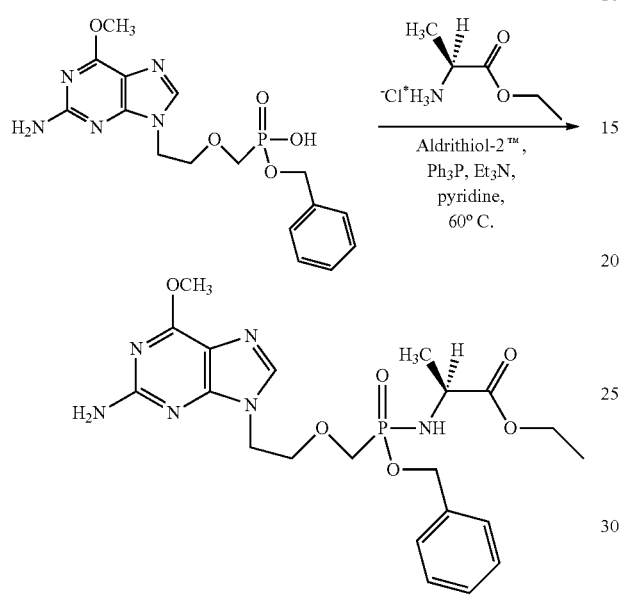

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the disclosure.

Embodiments

Embodiments disclosed herein include Embodiments P1 to P8 following.

Embodiment P1. A compound of the structure of Formula (I), or a pharmaceutically acceptable salt thereof:

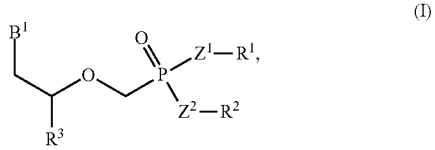

(I)

wherein: $B^1$ is a naturally occurring purine, a naturally occurring pyrimidine, a non-naturally occurring purine or a non-naturally occurring pyrimidine; $Z^1$ and $Z^2$ are independently O or $NR^Z$; $R^Z$ is hydrogen or an optionally substituted $C_{1-4}$ alkyl; $R^1$ is an optionally substituted —$C_{2-24}$ alkenyl, an optionally substituted —$C_{2-24}$ alkynyl, an optionally substituted —$(CHR^4)_a$—O—$C_{2-24}$ alkenyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl), an optionally substituted heteroaryl, an optionally substituted heteroaryl($C_1$-$C_4$ alkyl)-, an optionally substituted heterocyclyl, an optionally substituted heterocyclyl($C_1$-$C_4$ alkyl)-,

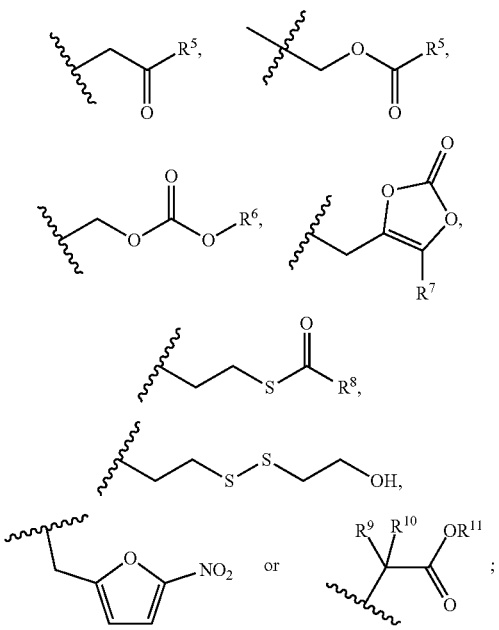

and $R^2$ is an optionally substituted —$C_{2-24}$ alkenyl, an optionally substituted —$C_{2-24}$ alkynyl, an optionally substituted —$(CHR^4)_b$—O—$C_{2-24}$ alkenyl, an optionally substituted cycloalkyl, an optionally substituted cycloalkyl($C_{1-4}$ alkyl)-, an optionally substituted cycloalkenyl, an optionally substituted cycloalkenyl($C_{1-4}$ alkyl)-, substituted aryl($C_{1-4}$ alkyl)-,

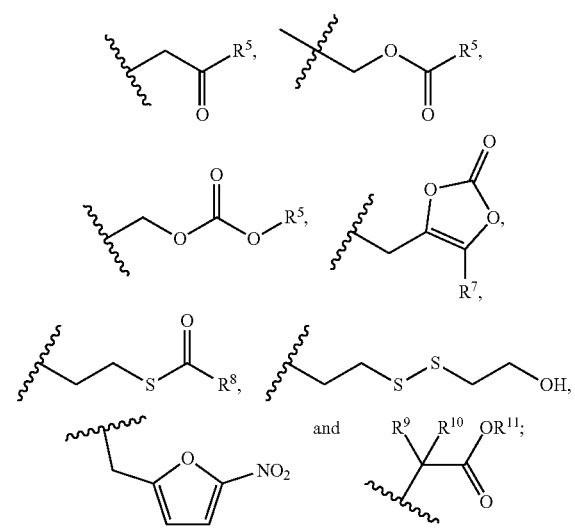

$R^1$ and $R^2$ can be taken together to form a moiety selected from an optionally substituted

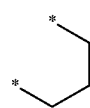 [SMILES: *CCC*]

or an optionally substituted

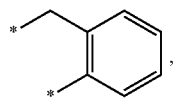, wherein $Z^1$, $Z^2$, $R^1$ and $R^2$, the phosphorus and the moiety form a six-membered to ten-membered ring system; $R^3$ is hydrogen, optionally substituted alkyl or optionally substituted heteroalkyl; each $R^4$ is independently hydrogen, —$(CH_2)_c$—S—$C_{1-24}$ alkyl or —O—$(CH_2)_d$—$R^{4A}$; each $R^{4A}$ is independently hydrogen, an optionally substituted $C_{1-24}$ alkyl or an optionally substituted aryl; each $R^5$, each $R^6$ and each $R^8$ are independently an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^7$ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^9$ and each $R^{10}$ are independently hydrogen or an optionally substituted $C_{1-6}$ alkyl; —$CH_2SH$, —$CH_2(C=O)NH_2$, —$CH_2CH_2(C=O)NH_2$, —$CH_2CH_2S$ $CH_3$, $CH_2$-an optionally substituted phenyl, —$CH_2OH$, —$CH(OH)CH_3$,

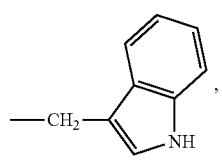, $(CH_2)_3NH(C=NH)NH_2$,

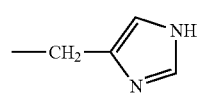

and —$(CH_2)_4NH_2$; each $R^{11}$ is independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl ($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl ($C_1$-$C_4$ alkyl)-; each a and each b are independently 1, 2, 3 or 4; and each c and each d are independently 0, 1, 2 or 3.

Embodiment P2. The compound of embodiment P1, wherein $B^1$ is:

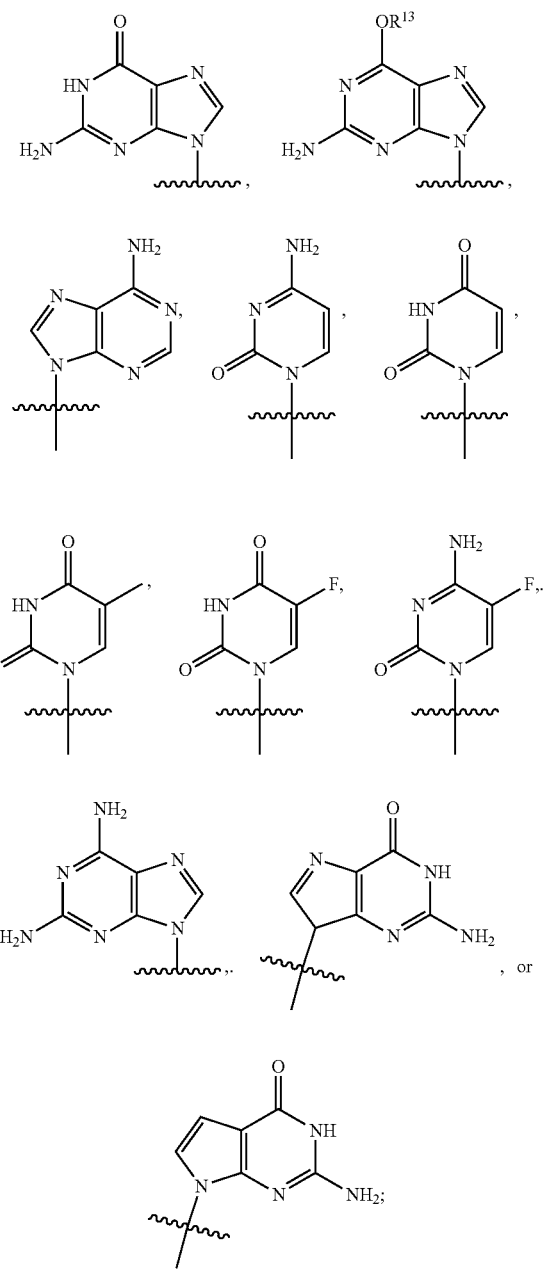

wherein: $R^{13}$ is unsubstituted $C_{1-6}$ alkyl or an unsubstituted $C_{3-6}$ cycloalkyl.

Embodiment P3. A compound of the formula:

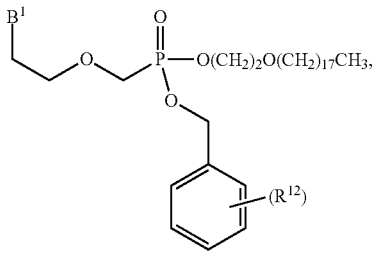

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

Embodiment P4. A compound of the formula:

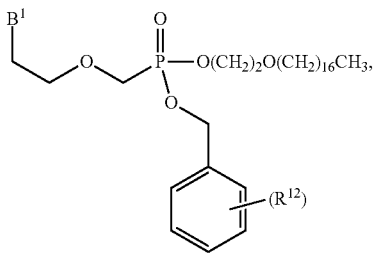

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

Embodiment P5. A compound of the formula:

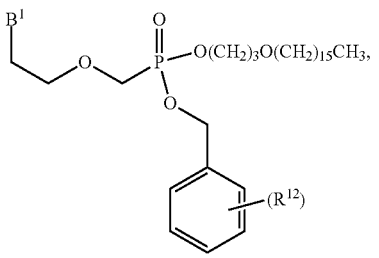

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

Embodiment P6. A compound of the formula:

wherein $B^1$ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

Embodiment P7. A compound of the formula:

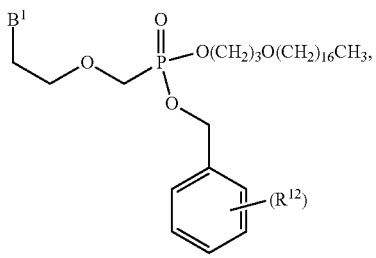

wherein B¹ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

Embodiment P8. A compound of the formula:

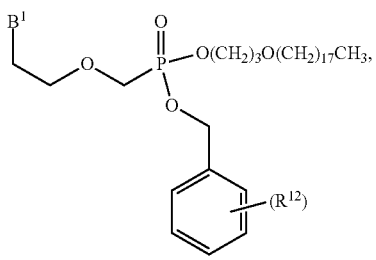

wherein B¹ is adenine, hypoxanthine, xanthine, theobromine, caffeine, uric acid, isoguanine, 2,6-diaminopurine, cytosine, thymine or uracil, 5-fluorouracil, 5-fluorocytosine, 7-deazaguanine or 9-deazaguanine; and $R^{12}$ is alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino group or a di-substituted amino group, and wherein the phenyl ring can be substituted by $R^{12}$ 1, 2 or 3 times, or its pharmaceutically acceptable salt.

Further embodiments include Embodiments 1 to 24 following.

Embodiment 1. A compound of the structure of Formula (I), or a pharmaceutically acceptable salt thereof:

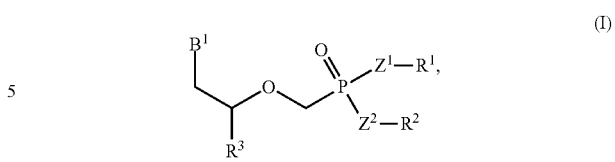

wherein: B¹ is selected from adenine, hypoxanthine, xanthine, theobromine, caffeine, uric acid, isoguanine, 2,6-diaminopurine, cytosine, thymine or uracil, guanine-7-yl, adenine-9-yl, cytosine-1-yl, thymin-1-yl, uracil-1-yl, 2,6-diaminopurin-9-yl, 5-fluorouracil, 5-fluorocytosine, 7-deazaguanine or 9-deazaguanine; $Z^1$ and $Z^2$ are independently O or $NR^Z$; $R^Z$ is hydrogen or an optionally substituted $C_{1-4}$ alkyl; $R^1$ is an optionally substituted $-C_{2-24}$ alkenyl, an optionally substituted $-C_{2-24}$ alkynyl, an optionally substituted $-(CHR^4)_a-O-C_{2-24}$ alkenyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl), an optionally substituted heteroaryl, an optionally substituted heteroaryl($C_1$-$C_4$ alkyl)-, an optionally substituted heterocyclyl, an optionally substituted heterocyclyl($C_1$-$C_4$ alkyl)-,

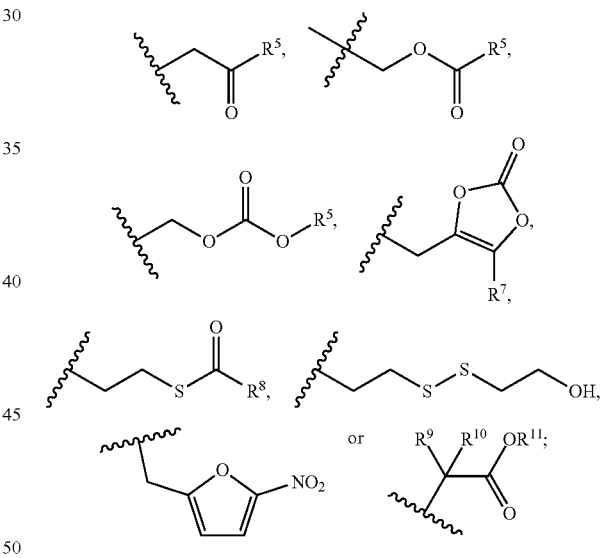

and $R^2$ is an optionally substituted $-C_{2-24}$ alkenyl, an optionally substituted $-C_{2-24}$ alkynyl, an optionally substituted $-(CHR^4)_b-O-C_{2-24}$ alkenyl, an optionally substituted cycloalkyl, an optionally substituted cycloalkyl($C_{1-4}$ alkyl)-, an optionally substituted cycloalkenyl, an optionally substituted cycloalkenyl($C_{1-4}$ alkyl)-, substituted aryl($C_{1-4}$ alkyl)-,

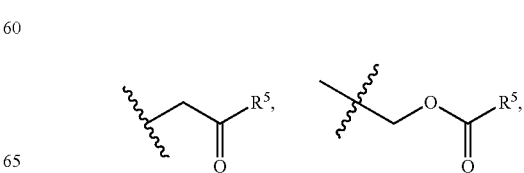

109
-continued

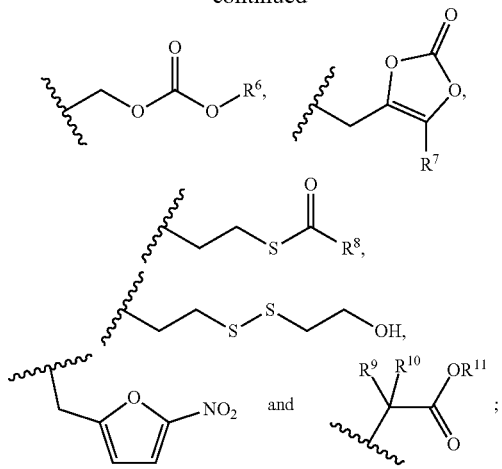

R¹ and R² can be taken together to form a moiety selected from an optionally substituted

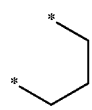 [SMILES: *CCC*]

or an optionally substituted

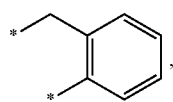

wherein $Z^1$, $Z^2$, $R^1$ and $R^2$, the phosphorus and the moiety form a six-membered to ten-membered ring system; $R^3$ is hydrogen, optionally substituted alkyl or optionally substituted heteroalkyl; each $R^4$ is independently hydrogen, —$(CH_2)_c$—S—$C_{1-24}$ alkyl or —O—$(CH_2)_d$—$R^{4A}$; each $R^{4A}$ is independently hydrogen, an optionally substituted $C_{1-24}$ alkyl or an optionally substituted aryl; each $R^5$, each $R^6$ and each $R^8$ are independently an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^7$ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^9$ and each $R^{10}$ are independently hydrogen or an optionally substituted $C_{1-6}$ alkyl; —$CH_2SH$, —$CH_2(C=O)$

110

$NH_2$, —$CH_2CH_2(C=O)NH_2$, —$CH_2CH_2S$ $CH_3$, $CH_2$-an optionally substituted phenyl, —$CH_2OH$, —$CH(OH)CH_3$,

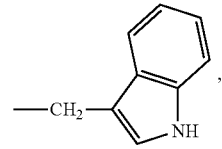

—$CH_2(C=O)OH$, —$CH_2CH_2(C=O)OH$, —$(CH_2)_3NH(C=NH)NH_2$,

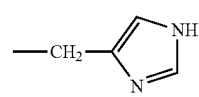

and —$(CH_2)_4NH_2$; each $R^{11}$ is independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each a and each b are independently 1, 2, 3 or 4; and each c and each d are independently 0, 1, 2 or 3.

Embodiment 2. A compound of the structure of Formula (I), or a pharmaceutically acceptable salt thereof:

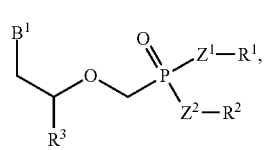

(I)

wherein: $B^1$ is guanine; $Z^1$ and $Z^2$ are independently O or $NR^Z$; $R^Z$ is hydrogen or an optionally substituted $C_{1-4}$ alkyl; $R^1$ is an optionally substituted —$C_{2-24}$ alkenyl, an optionally substituted —$C_{2-24}$ alkynyl, an optionally substituted —$(CHR^4)_a$—O—$C_{2-24}$ alkenyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl), an optionally substituted heteroaryl, an optionally substituted heteroaryl($C_1$-$C_4$ alkyl)-, an optionally substituted heterocyclyl, an optionally substituted heterocyclyl($C_1$-$C_4$ alkyl)-,

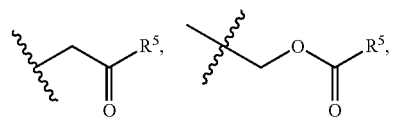

-continued

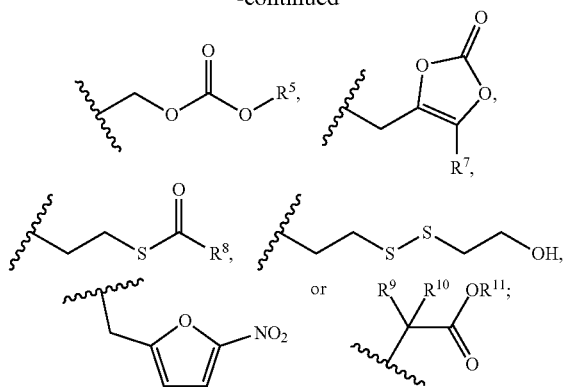

and $R^2$ is an optionally substituted —$C_{2-24}$ alkenyl, an optionally substituted —$C_{2-24}$ alkynyl, an optionally substituted —$(CHR^4)_b$—O—$C_{2-24}$ alkenyl, an optionally substituted cycloalkyl, an optionally substituted cycloalkyl($C_{1-4}$ alkyl)-, an optionally substituted cycloalkenyl, an optionally substituted cycloalkenyl($C_{1-4}$ alkyl)-, substituted aryl($C_{1-4}$ alkyl)-,

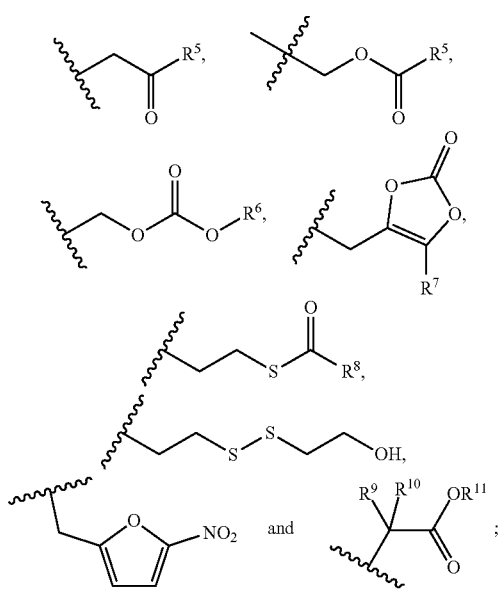

$R^1$ and $R^2$ can be taken together to form a moiety selected from an optionally substituted

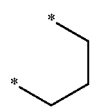 [SMILES: *CCC*]

or an optionally substituted

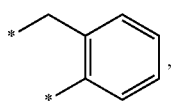

wherein $Z^1$, $Z^2$, $R^1$ and $R^2$, the phosphorus and the moiety form a six-membered to ten-membered ring system; $R^3$ is optionally substituted alkyl or optionally substituted heteroalkyl; each $R^4$ is independently hydrogen, —$(CH_2)_c$—S—$C_{1-24}$ alkyl or —O—$(CH_2)_d$—$R^{4A}$; each $R^{4A}$ is independently hydrogen, an optionally substituted $C_{1-24}$ alkyl or an optionally substituted aryl; each $R^5$, each $R^6$ and each $R^8$ are independently an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl ($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^7$ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^9$ and each $R^{10}$ are independently hydrogen or an optionally substituted $C_{1-6}$ alkyl; —$CH_2SH$, —$CH_2(C=O)NH_2$, —$CH_2CH_2(C=O)NH_2$, —$CH_2CH_2S$ $CH_3$, $CH_2$-an optionally substituted phenyl, —$CH_2OH$, —$CH(OH)CH_3$,

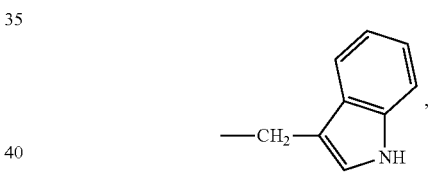

—$CH_2(C=O)OH$, —$CH_2CH_2(C=O)OH$, —$(CH_2)_3NH(C=NH)NH_2$,

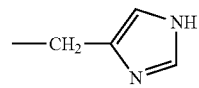

and —$(CH_2)_4NH_2$; each $R^{11}$ is independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl ($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl ($C_1$-$C_4$ alkyl)-; each a and each b are independently 1, 2, 3 or 4; and each c and each d are independently 0, 1, 2 or 3.

Embodiment 3. A compound of the structure of Formula (I), or a pharmaceutically acceptable salt thereof:

wherein: B¹ is

[structure: guanine-like purine with OR¹³ and H₂N, attached via N]

Z¹ and Z² are independently O or NR$^Z$; R$^Z$ is hydrogen or an optionally substituted $C_{1-4}$ alkyl; R¹ is an optionally substituted —$C_{2-24}$ alkenyl, an optionally substituted —$C_{2-24}$ alkynyl, an optionally substituted —(CHR⁴)$_a$—O—$C_{2-24}$ alkenyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl), an optionally substituted heteroaryl, an optionally substituted heteroaryl($C_1$-$C_4$ alkyl)-, an optionally substituted heterocyclyl, an optionally substituted heterocyclyl($C_1$-$C_4$ alkyl)-,

[structures showing various R groups]

and R² is an optionally substituted —$C_{2-24}$ alkenyl, an optionally substituted —$C_{2-24}$ alkynyl, an optionally substituted —(CHR⁴)$_b$—O—$C_{2-24}$ alkenyl, an optionally substituted cycloalkyl, an optionally substituted cycloalkyl($C_{1-4}$ alkyl)-, an optionally substituted cycloalkenyl, an optionally substituted cycloalkenyl($C_{1-4}$ alkyl)-, substituted aryl($C_{1-4}$ alkyl)-,

[structures showing various R groups]

R¹ and R² can be taken together to form a moiety selected from an optionally substituted

[structure]

or an optionally substituted

[structure]

wherein Z¹, Z², R¹ and R², the phosphorus and the moiety form a six-membered to ten-membered ring system; R³ is optionally substituted alkyl or optionally substituted heteroalkyl; each R⁴ is independently hydrogen, —(CH₂)$_c$—S—$C_{1-24}$ alkyl or —O—(CH₂)$_d$—R$^{4A}$; each R$^{4A}$ is independently hydrogen, an optionally substituted $C_{1-24}$ alkyl or an optionally substituted aryl; each R⁵, each R⁶ and each R⁸ are independently an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl ($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each R⁷ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; each $R^9$ and each $R^{10}$ are independently hydrogen or an optionally substituted $C_{1-6}$ alkyl; —$CH_2SH$, —$CH_2(C=O)NH_2$, —$CH_2CH_2(C=O)NH_2$, —$CH_2CH_2S$ $CH_3$, $CH_2$—an optionally substituted phenyl, —$CH_2OH$, —$CH(OH)CH_3$,

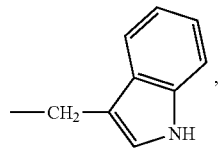,

—$CH_2(C=O)OH$, —$CH_2CH_2(C=O)OH$, —$(CH_2)_3NH(C=NH)NH_2$,

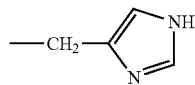

and —$(CH_2)_4NH_2$; each $R^{11}$ is independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl ($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl ($C_1$-$C_4$ alkyl)-; $R^{13}$ is unsubstituted $C_{1-6}$ alkyl or an unsubstituted $C_{3-6}$ cycloalkyl; each a and each b are independently 1, 2, 3 or 4; and each c and each d are independently 0, 1, 2 or 3.

Embodiment 4. The compound of embodiment 1, wherein $B^1$ is:

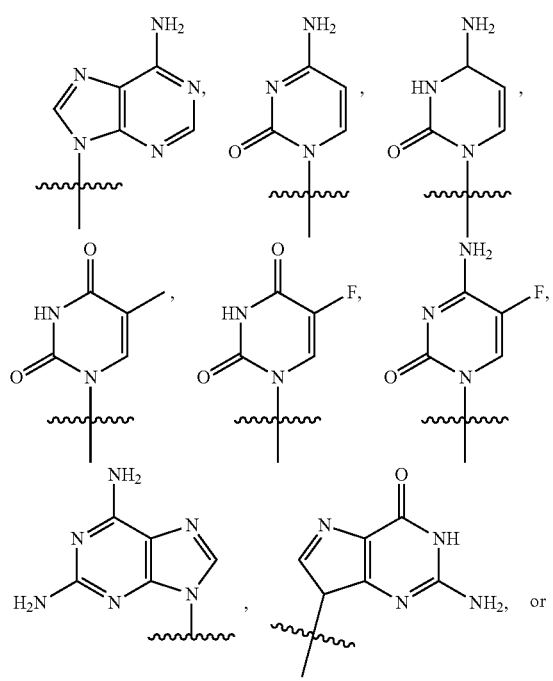

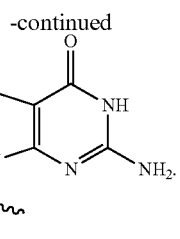

Embodiment 5. A compound of the formula:

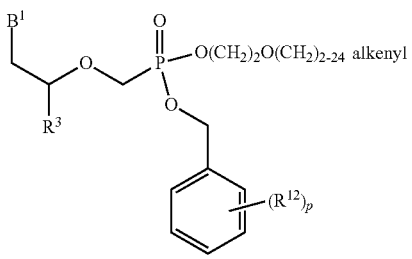

wherein: $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; p=1, 2, 3, 4 or 5; and $B^1$ and $R^3$ are as defined in embodiment 1; or its pharmaceutically acceptable salt.

Embodiment 6. A compound of the formula:

(Ib)

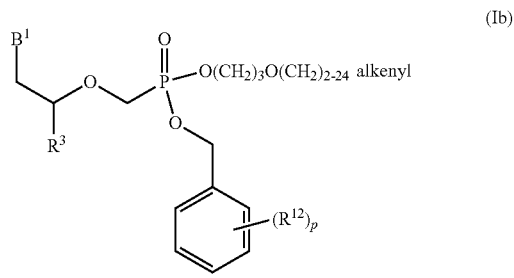

wherein: p=1, 2, 3, 4 or 5; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 7. A compound of the formula:

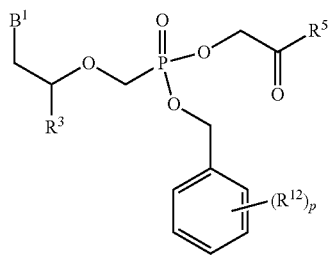

wherein: p=1, 2, 3, 4 or 5; $R^5$ is an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 8. A compound of the formula:

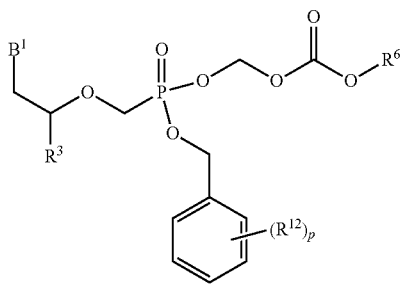

wherein: p=1, 2, 3, 4 or 5; $R^6$ is an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 9. A compound of the formula:

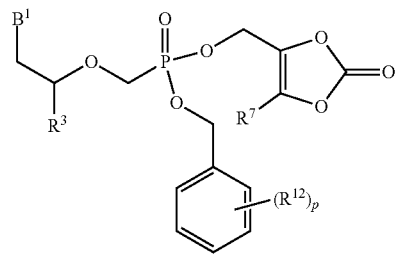

wherein: p=1, 2, 3, 4 or 5; $R^7$ is independently hydrogen, an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 10. A compound of the formula:

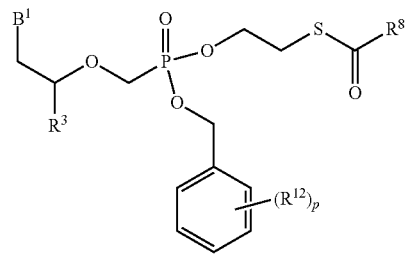

wherein: p=1, 2, 3, 4 or 5; $R^8$ is an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-;

$R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 11. A compound of the formula:

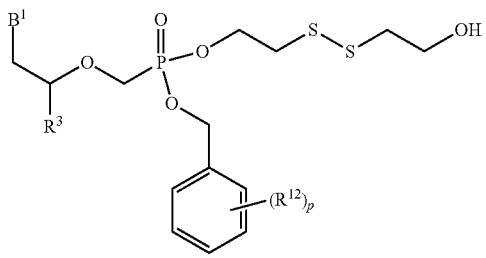

wherein: p=1, 2, 3, 4 or 5; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl (alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 12. A compound of the formula:

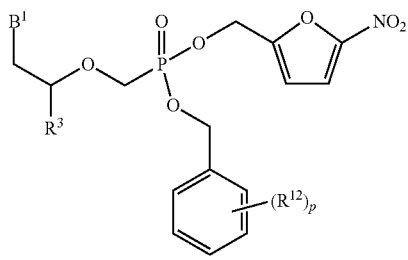

wherein: p=1, 2, 3, 4 or 5; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl (alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 13. A compound of the formula:

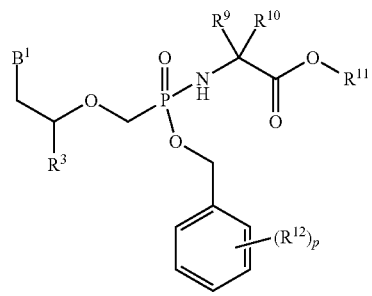

wherein: p=1, 2, 3, 4 or 5; each $R^9$ and each $R^{10}$ are independently hydrogen or an optionally substituted $C_{1-6}$ alkyl; —CH$_2$SH, —CH$_2$(C=O)NH$_2$, —CH$_2$CH$_2$(C=O) NH$_2$, —CH$_2$CH$_2$S CH$_3$, CH$_2$-an optionally substituted phenyl, —CH$_2$OH, —CH(OH)CH$_3$,

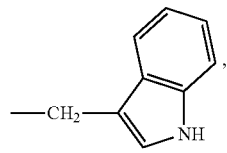

—CH$_2$(C=O)OH, —CH$_2$CH$_2$(C=O)OH, —(CH$_2$)$_3$NH (C=NH)NH$_2$,

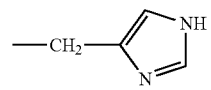

and —(CH$_2$)$_4$NH$_2$; $R^{11}$ is independently hydrogen, an optionally substituted $C_{1-8}$ alkyl, an optionally substituted $C_{2-8}$ alkenyl, an optionally substituted alkynyl, an optionally substituted cycloalkyl, an optionally substituted cycloalkyl ($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl ($C_1$-$C_4$ alkyl)-; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 14. A compound of the formula:

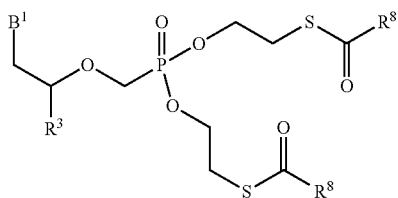

wherein: p=1, 2, 3, 4 or 5; $R^8$ is an optionally substituted $C_{1-8}$ alkyl, an optionally substituted $C_{2-8}$ alkenyl, an optionally substituted $C_{2-8}$ alkynyl, an optionally substituted cycloalkyl, an optionally substituted cycloalkyl($C_1$-$C_4$ alkyl)-, an optionally substituted cycloalkenyl, an optionally substituted cycloalkenyl($C_1$-$C_4$ alkyl)-, an optionally substituted aryl, an optionally substituted aryl($C_{1-4}$ alkyl)-, an optionally substituted heteroaryl, an optionally substituted heteroaryl($C_1$-$C_4$ alkyl)-, an optionally substituted heterocyclyl, or an optionally substituted heterocyclyl($C_1$-$C_4$ alkyl)-; and $B^1$ and $R^3$ are as defined in embodiment 1; or its pharmaceutically acceptable salt.

Embodiment 15. A compound of the formula:

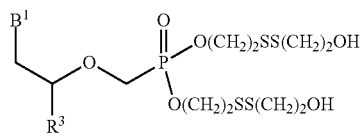

wherein: $B^1$ and $R^3$ are as defined in embodiment 1; or its pharmaceutically acceptable salt.

Embodiment 16. A compound of the formula:

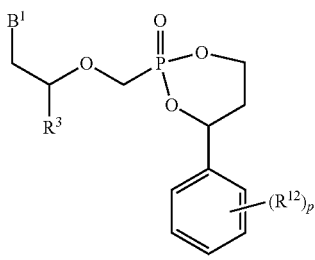

wherein: p=1, 2, 3, 4 or 5; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 17. A compound of the formula:

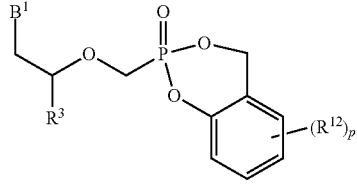

wherein: p=1, 2, 3, 4 or 5; $R^{12}$ is alkyl, alkenyl, alkynyl, cycloalkyl, cycloalkyl(alkyl), cycloalkenyl, cycloalkenyl(alkyl), aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, a mono-substituted amino group or a di-substituted amino group; and $B^1$ and $R^3$ are as defined in embodiment 1; or its pharmaceutically acceptable salt.

Embodiment 18. A pharmaceutical composition comprising an effective amount of a compound of any one of embodiments 1-17, or a pharmaceutically acceptable salt thereof, and a pharmaceutically acceptable excipient.

Embodiment 19. The pharmaceutical composition of embodiment 18, wherein the pharmaceutical composition is in the form of a cream, a gel or an ointment.

Embodiment 20. The pharmaceutical composition of embodiment 18 or 19, wherein the pharmaceutical composition is a topical formulation.

Embodiment 21. Use of a compound of any one of embodiments 1-17, or a pharmaceutically acceptable salt thereof, in the preparation of a medicament for treating a viral disease in a subject in need thereof, wherein the viral disease is human papilloma virus.

Embodiment 22. The use of embodiment 21, said compound, or a pharmaceutically acceptable salt thereof, for use in treating a plurality of types of human papilloma virus.

Embodiment 23. The use of embodiment 21, wherein the human papilloma virus is selected from the group consisting human papilloma virus HPV-16, HPV-18, HPV-31, HPV-33, HPV-35, HPV-39, HPV-45, HPV-51, HPV-52, HPV-56, HPV-58, HPV-59, HPV-68, HPV-73 and HPV-82.

Embodiment 24. Use of a compound of any one of embodiments 1-17, or a pharmaceutically acceptable salt thereof, in the preparation of a medicament for treating cancer of the cervix in a subject in need thereof.

What is claimed is:
1. A compound of the structure of Formula (I), or a pharmaceutically acceptable salt thereof:

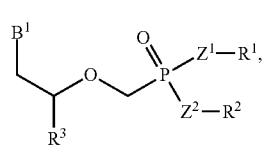

(I)

wherein:

B¹ is

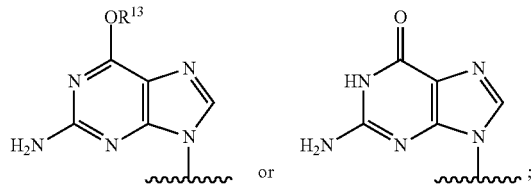

$Z^1$ is O;
$Z^2$ is $NR^Z$;
$R^Z$ is hydrogen or $C_{1-4}$ alkyl;
$R^1$ is aryl, or aryl($C_{1-4}$ alkyl);
$R^2$ is

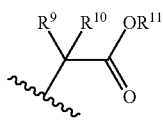

$R^3$ is $CHF_2$, $CF_3$, or $OCH_3$;
each $R^9$ and each $R^{10}$ are independently hydrogen, $C_{1-6}$alkyl, —$CH_2SH$, —$CH_2(C$=$O)NH_2$, —$CH_2CH_2(C$=$O)NH_2$, —$CH_2CH_2SCH_3$, $CH_2$—phenyl, —$CH_2OH$, —$CH(OH)CH_3$,

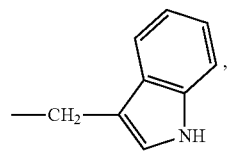

—$CH_2(C$=$O)OH$, —$CH_2CH_2(C$=$O)OH$, —$(CH_2)_3NH(C$=$NH)NH_2$,

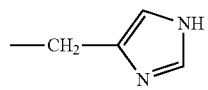

or —$(CH_2)_4NH_2$;
each $R^{11}$ is independently hydrogen, $C_{1-8}$ alkyl, $C_{2-8}$ alkenyl, alkynyl, cycloalkyl, cycloalkyl($C_1$-$C_4$ alkyl)-, cycloalkenyl, cycloalkenyl($C_1$-$C_4$ alkyl)-, aryl, aryl($C_{1-4}$ alkyl)-, heteroaryl, heteroaryl($C_1$-$C_4$ alkyl)-, heterocyclyl, or heterocyclyl($C_1$-$C_4$ alkyl)-; and
$R^{13}$ is unsubstituted $C_{1-6}$ alkyl or an unsubstituted $C_{3-6}$ cycloalkyl.

2. A pharmaceutical composition comprising an effective amount of a compound of claim 1, or a pharmaceutically acceptable salt thereof, and a pharmaceutically acceptable excipient.

3. The pharmaceutical composition of claim 2, wherein the pharmaceutical composition is in the form of a cream, a gel or an ointment.

4. The pharmaceutical composition of claim 2, wherein the pharmaceutical composition is a topical formulation.

5. A method for treating human papilloma virus comprising administering a compound of claim 1, or pharmaceutically acceptable salt thereof, to a subject in need thereof.

6. The method of claim 5, wherein the human papilloma virus is selected from the group consisting of human papilloma virus HPV-16, HPV-18, HPV-31, HPV-33, HPV-35, HPV-39, HPV-45, HPV-51, HPV-52, HPV-56, HPV-58, HPV-59, HPV-68, HPV-73 and HPV-82.

7. A method for treating cancer of the cervix comprising administering a compound of claim 1, or pharmaceutically acceptable salt thereof, to a subject in need thereof.

8. The method of claim 6, wherein the human papilloma virus is HPV-16 or HPV-18.

9. The method of claim 6, wherein the human papilloma virus is HPV-52 or HPV-58.

10. A method for treating cervical intraepithelial neoplasia, anal intraepithelial neoplasia, or vaginal intraepithelial neoplasia comprising administering a compound of claim 1, or pharmaceutically acceptable salt thereof, to a subject in need thereof.

11. The compound of claim 1, wherein B¹ is

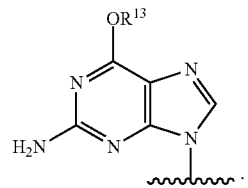

12. The compound of claim 11, wherein $R^{13}$ is methyl.

13. The compound of claim 1, wherein B¹ is

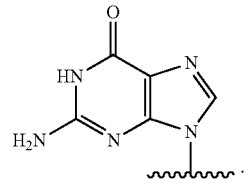

14. The compound of claim 1, wherein $R^3$ is $CF_3$.
15. The compound of claim 1, wherein $R^3$ is $CHF_2$.
16. The compound of claim 1, wherein $R^3$ is $OCH_3$.
17. The compound of claim 1, wherein $R^Z$ is hydrogen.
18. The compound of claim 17, wherein $R^9$ and $R^{10}$ are independently selected from the group consisting of hydrogen and $C_{1-6}$ alkyl.
19. The compound of claim 18, wherein $R^9$ is hydrogen and $R^{10}$ is methyl.
20. The compound of claim 18, wherein $R^{11}$ is $C_{1-8}$ alkyl.
21. The compound of claim 20, wherein $R^{11}$ is ethyl.
22. The compound of claim 1, wherein $R^1$ is aryl.
23. The compound of claim 22, wherein $R^1$ is phenyl.
24. The compound of claim 1, wherein $R^1$ is aryl($C_{1-4}$ alkyl).
25. The compound of claim 24, wherein $R^1$ is benzyl.

* * * * *